United States Patent
Kastelein et al.

(10) Patent No.: US 11,859,001 B2
(45) Date of Patent: Jan. 2, 2024

(54) IL12RB1-BINDING MOLECULES AND METHODS OF USE

(71) Applicants: SYNTHEKINE, INC., Menlo Park, CA (US); Sandro Vivona, Menlo Park, CA (US)

(72) Inventors: Robert Kastelein, Menlo Park, CA (US); Deepti Rokkam, Menlo Park, CA (US); Patrick J. Lupardus, Menlo Park, CA (US); Sandro Vivona, Menlo Park, CA (US)

(73) Assignee: Synthekine, Inc., Menlo Park, CA (US)

( * ) Notice: Subject to any disclaimer, the term of this patent is extended or adjusted under 35 U.S.C. 154(b) by 0 days.

(21) Appl. No.: 18/017,282

(22) PCT Filed: Aug. 5, 2021

(86) PCT No.: PCT/US2021/044674
§ 371 (c)(1),
(2) Date: Jan. 20, 2023

(87) PCT Pub. No.: WO2022/031929
PCT Pub. Date: Feb. 10, 2022

(65) Prior Publication Data
US 2023/0272093 A1    Aug. 31, 2023

Related U.S. Application Data

(60) Provisional application No. 63/135,884, filed on Jan. 11, 2021, provisional application No. 63/078,745, filed on Sep. 15, 2020, provisional application No. 63/061,562, filed on Aug. 5, 2020.

(51) Int. Cl.
*C07K 16/24* (2006.01)
*C07K 16/28* (2006.01)
*C07K 14/715* (2006.01)
*C12N 15/63* (2006.01)

(52) U.S. Cl.
CPC ...... *C07K 16/2866* (2013.01); *C07K 14/7155* (2013.01); *C12N 15/63* (2013.01); *C07K 2317/24* (2013.01); *C07K 2317/565* (2013.01); *C07K 2317/569* (2013.01)

(58) Field of Classification Search
CPC ............ C07K 16/2866; C07K 14/7155; C07K 2317/565; C07K 2317/569
See application file for complete search history.

(56) References Cited

U.S. PATENT DOCUMENTS

| | | |
|---|---|---|
| 8,258,268 B2 | 9/2012 | Wu et al. |
| 8,921,528 B2 | 12/2014 | Holt et al. |
| 8,975,382 B2 | 3/2015 | Revets et al. |
| 10,927,186 B2 | 2/2021 | Roobrouck et al. |
| 2006/0024295 A1 | 2/2006 | Brunetta |
| 2010/0297127 A1 | 11/2010 | Ghilardi et al. |
| 2011/0028695 A1 | 2/2011 | Revets et al. |
| 2011/0053865 A1 | 3/2011 | Saunders et al. |
| 2011/0142831 A1 | 6/2011 | Cua et al. |
| 2012/0082681 A1* | 4/2012 | Carballido Herrera ...... C07K 16/2866 435/69.6 |
| 2012/0201746 A1 | 8/2012 | Liu et al. |
| 2012/0316324 A1 | 12/2012 | Adams et al. |
| 2014/0065142 A1 | 3/2014 | Roschke et al. |
| 2014/0099708 A1 | 4/2014 | Carballido Herrera et al. |
| 2015/0079088 A1 | 3/2015 | Lowman et al. |
| 2016/0046730 A1 | 2/2016 | Ghayur et al. |
| 2016/0251440 A1* | 9/2016 | Roobrouck ........ C07K 16/3007 424/138.1 |
| 2017/0106051 A1 | 4/2017 | Oh et al. |
| 2017/0298149 A1 | 10/2017 | Baeuerle et al. |
| 2018/0362655 A1 | 12/2018 | Wang et al. |
| 2020/0157237 A1 | 5/2020 | Regev et al. |

FOREIGN PATENT DOCUMENTS

| | | |
|---|---|---|
| CN | 103396482 A | 11/2013 |
| CN | 111018985 A | 6/2019 |
| WO | 2008/011081 A2 | 1/2008 |
| WO | 2009/068631 A1 | 6/2009 |
| WO | 2013/006544 A1 | 1/2013 |
| WO | 2013/059299 A1 | 4/2013 |
| WO | 2016/097313 A1 | 6/2016 |
| WO | 2017/198212 A1 | 11/2017 |
| WO | 2019/129221 A1 | 7/2019 |
| WO | 2020/144164 A1 | 7/2020 |
| WO | 2020/187711 A1 | 9/2020 |

OTHER PUBLICATIONS

International Search Report in PCT/US2021/044674, dated Jan. 19, 2022, 12 pages.
Pingwara et al. IFN-λ Modulates the Migratory Capacity of Canine Mammary Tumor Cells via Regulation of the Expression of Matrix Metalloproteinases and Their Inhibitors. Cells. Apr. 23, 2021;10(5):999.

\* cited by examiner

*Primary Examiner* — Dong Jiang
(74) *Attorney, Agent, or Firm* — Kilpatrick Townsend & Stockton LLP

(57) ABSTRACT

The present disclosure relates to biologically active molecules comprising a single domain antibody (sdAb) that specifically binds to the extracellular domain of human 1LI2RM, compositions comprising such antibodies, and methods of use thereof.

14 Claims, No Drawings

Specification includes a Sequence Listing.

IL12RB1-BINDING MOLECULES AND METHODS OF USE

CROSS-REFERENCES TO RELATED APPLICATIONS

This application is a national stage application under 35 U.S.C. 371 of PCT/US2021/044674, filed Aug. 5, 2021, which claims priority to U.S. Provisional Application No. 63/061,562, filed Aug. 5, 2020, U.S. Provisional Application No. 63/078,745, filed Sep. 15, 2020, and U.S. Provisional Application No. 63/135,884, filed Jan. 11, 2021, the disclosures of which are hereby incorporated by reference in their entirety for all purposes.

SEQUENCE LISTING

The instant application contains a Sequence Listing which has been submitted electronically in ASCII format and is hereby incorporated by reference in its entirety. Said ASCII copy, created on Jan. 18, 2023, is named 106249-1361759_SEQ_LST.txt and is 148,266 bytes in size.

FIELD OF THE INVENTION

The present disclosure relates to biologically active molecules comprising a single domain antibody that specifically binds to the extracellular domain of the IL12RB1, compositions comprising such single domain antibodies, and methods of use thereof.

BACKGROUND

IL12 is a heterodimeric cytokine comprise of the p35 and p40 subunits produced by dendritic cells, macrophages and neutrophils. The IL12 heterodimer is also referred to as p70. IL12 is typically identified as a T cell stimulating factor which can stimulate the proliferation and activity of T cells. IL12 stimulates the production of IFNgamma and TNFalpha and modulates the cytotoxic activity of NK and CD8+ cytotoxic T cells. IL12 is also involved in the immune cell differentiation in particular the differentiation of naïve T cells into Th1 (CD4+) cells. IL12 is also reported to provide anti-antiogenic activity. IL12 has been proposed for use in the treatment of a variety of neoplastic diseases, viral and bacterial infections.

IL12 binds to the IL12 receptor, a heterodimeric complex of IL12 receptor subunit beta-1 (IL12Rβ1 or IL12RB1) and IL12 receptor subunit beta-2 (IL12Rβ2 or IL12RB2). IL12Rβ1 and IL12Rβ2 are members of the class I cytokine receptor family and have homology to gp130. The expression of IL12Rβ1 and IL12Rβ2 are upregulated in response to IL2 with the majority of IL12Rβ2 is found on activated T cells.

IL12Rβ1 (also known as CD212) is a constitutively expressed type I transmembrane protein that belongs to the hemopoietin receptor superfamily. IL12Rβ1 binds with low affinity to IL12. IL12Rβ1 is required for high-affinity binding to the IL12p40 subunit and it is associated with the Janus kinase (Jak) family member Tyk-2. The binding IL12p40 and IL12p35 to IL12Rβ1 and IL12Rβ2, respectively results in the activation of the Tyk-2 and Jak-2 Janus kinases occurs. The phosphorylated intracellular signaling domain of IL12Rβ2 provides a binding site for STAT4, which are phosphorylated and translocate to the nucleus regulating IFNgamma gene transcription.

In addition to forming one of the components of the IL12 receptor, IL12Rβ1 is also a component of the IL23 receptor. The IL23 receptor is a heterodimer of IL23R and IL12Rβ1. IL23 binds IL23R with an affinity of 44 nM but binds to IL2Rβ1 with a significantly lower affinity of 2 µM. There is no apparent direct binding of IL23R to IL12Rβ1, the completion of the IL23:IL23R:IL12Rβ1 complex mediated by the initial formation of the IL23:IL23R complex which in turn binds to IL12Rβ1.

The p40 subunit of the IL23 and IL12 cytokines provides the majority of binding sites for IL12Rβ1. In addition to forming a subunit of IL12 and IL23, p40 alone has significant bioactivity. P40 is reported to exist as both a monomer and a disulfide linked homodimer and which has a chemo attractant role for macrophages mediated by IL12101 alone. Gillesssen, et al (1995) European J. Immuno 25(1):200-206. The p40 homodimer is reported as a IL12 antagonist and its binding to IL12Rb1 is postulated to sequester the IL12Rb1 on the cell surface and suppressing the internalization or endocytosis of IL12Rβ1. Kundu, et al. (2017) PNASUSA 114(43):1148211487. Neutralization of p40 has been identified as reducing acute and chronic GVHD through reducing Th1 and Th17 differentiation. This is in contrast to reports that IL12 can both exacerbate and suppress GVHD in various contexts but that targeting p40 has been p40 can be efficacious in reducing GVHD severity in experimental and clinical settings. In short, the activity of IL12 is a function of the competitive interaction of the IL12, p40 monomer and p40 homodimer with the IL12 receptor, in particular IL12Rβ1. Consequently, molecules which interfere in the association of p40 with IL12Rβ1 may be useful in the modulation of IL12 activity.

Although monoclonal antibodies are the most widely used reagents for the detection and quantification of proteins, monoclonal antibodies are large molecules of about 150 kDa and it sometimes limits their use in assays with several reagents competing for close epitopes recognition. A unique class of immunoglobulin containing a heavy chain domain and lacking a light chain domain (commonly referred to as heavy chain" antibodies (HCAbs) is present in camelids, including dromedary camels, Bactrian camels, wild Bactrian camels, llamas, alpacas, vicuñas, and guanacos as well as cartilaginous fishes such as sharks. The isolated variable domain region of HCAbs is known as a VHH (an abbreviation for "variable-heavy-heavy" reflecting their architecture) or Nanobody® (Ablynx). Single domain VHH antibodies possesses the advantage of small size (~12-14 kD), approximately one-tenth the molecular weight a conventional mammalian IgG class antibody) which facilitates the binding of these VHH molecules to antigenic determinants of the target which may be inaccessible to a conventional monoclonal IgG format (Ingram et al., 2018). Furthermore, VHH single domain antibodies are frequently characterized by high thermal stability facilitating pharmaceutical distribution to geographic areas where maintenance of the cold chain is difficult or impossible. These properties, particularly in combination with simple phage display discovery methods that do not require heavy/light chain pairing (as is the case with IgG antibodies) and simple manufacture (e.g., in bacterial expression systems) make VHH single domain antibodies useful in a variety of applications including the development of imaging and therapeutic agents that selectively bind cell surface exposed proteins.

SUMMARY OF THE INVENTION

The present disclosure provides polypeptides that specifically bind to the extracellular domain of IL12RB1.

The present disclosure provides a IL12RB1 binding molecule that specifically bind to the extracellular domain of IL12RB1 (e.g., human IL12RB1).

In some embodiments, the IL12RB1 binding molecule comprises a single domain antibody (sdAb) that specifically binds to the extracellular domain of the human IL12RB1.

In some embodiments, the IL12RB1 binding molecule is a sdAb, the sdAb comprising a set of CDRs corresponding to CDR1, CDR2, and CDR3 as shown in a row of Table 1A below.

In some embodiments, the IL12RB1 binding molecule comprises a CDR1, a CDR2, and a CDR3 as described in a row of Table 1 below, in which the CDR1, CDR2, and CDR3 can each, independently, comprise at least 90% (e.g., 91%, 92%, 93%, 94%, 95%, 96%, 97%, 98%, 99%, or 100%) sequence identity, or have 0, 1, 2, or 3 amino acid changes, optionally conservative amino acid changes, relative to the sequence described in a row of Table 1 below.

In some embodiments, the IL12RB1 binding molecule consists of, optionally consists essentially of, or optionally comprises a single domain antibody (sdAb) having at least 80%, alternatively at least 85%, alternatively at least 90%, alternatively at least 95%, alternatively at least 98%, alternatively at least 99% identity (or being identical except for 1, 2, 3, or 4 amino acids that optionally are conserved substitutions) or 100% identity to a polypeptide sequence of any one of SEQ ID NOS:2-23, as shown in Table 1 below.

TABLE 1 hIL12RB ECD Generated VHHs and CDRS

| Name | Sequence (CDRs Underlined) | CDR1 | CDR2 | CDR3 |
|---|---|---|---|---|
| hIL12Rb1_VHH1 | QVQLQESGGGSVQAGGSLR LSCVASGYGYCGYDMSWY RQAPGKEREFVALITSDRSI YEDSVKARFIISRDNAANTG YLDMTRLTPDDTAIYYCKT SAAARESSWCRSRYRVASW GQGTQVTVSS (SEQ ID NO: 2) | YGYCGYDMS (SEQ ID NO: 24) | LITSDRSISYE DSVKA (SEQ ID NO: 25) | SAAARESSWC RSRYRVAS (SEQ ID NO: 26) |
| hIL12Rb1_VHH2 | QVQLQESGGGSVQAGGSLR LSCTASGYTYSSAFMAWFR QAPGKEREGVAAIYTRDGG TVYADSVKGRFTISQDNAK NILYLQMNSLKAEDTAMYY CAAKIPQPGRASLLDSQTYD YWGQGTQVTVSS (SEQ ID NO: 3) | YTYSSAFMA (SEQ ID NO: 27) | AIYTRDGGTV YADSVKG (SEQ ID NO: 28) | KIPQPGRASLL DSQTYDY (SEQ ID NO: 29) |
| hIL12Rb1_VHH3 | QVQLQESGGGSVQAGGSLR LSCVASGYSYCGYDMMWY RQAPGKEREFVALITSDYSI RYEDSVEGRFSISRDNAKNT GYLLMSNLTPADTAIYYCK TSTAARESSWCRSRYRVAS WGQGTQVTVSS (SEQ ID NO: 4) | YSYCGYDMM (SEQ ID NO: 30) | LITSDYSIRYE DSVEG (SEQ ID NO: 31) | STAARESSWCR SRYRVAS (SEQ ID NO: 32) |
| hIL12Rb1_VHH4 | QVQLQESGGGSVQAGGSLR LSCVASGYGYCGYDMSWY RQTPGKEREFVALITSDRIAS YEDSVKGRFIISRDNAKNTG YLDMTRVTPDDTAIYYCKT SAAARENSWCRSRYRVAS WGQGTQVTVSS (SEQ ID NO: 5) | YGYCGYDMS (SEQ ID NO: 33) | LITSDRIASYE DSVKG (SEQ ID NO: 34) | SAAARENSWC RSRYRVAS (SEQ ID NO: 35) |
| hIL12Rb1_VHH5 | QVQLQESGGGSVQAGGFLR LSCVASGYGYCGYDMSWY RQVPGKEREFVALITSDRSV SYEDSVKGRFSISRDNAKNT AYLEMNRLTPDDTAVYYC KTSTAARENNWCRSRYRIA YWGQGTQVTVSS (SEQ ID NO: 6) | YGYCGYDMS (SEQ ID NO: 36) | LITSDRSVSYE DSVKG (SEQ ID NO: 37) | STAARENNWC RSRYRIAY (SEQ ID NO: 38) |
| hIL12Rb1_VHH6 | QVQLQESGGGSVQAGGSLR LSCAASRYTYTNNFMAWFR QAPGKEREGVAAIYTGDGY AYYFYSVKGRFTISQDNDE NMLYLQMNSLKPEDTAMY YCAAMERRIGTRRMTENAE YKYWGQGTQVTVSS (SEQ ID NO: 7) | YTYTNNFMA (SEQ ID NO: 39) | AIYTGDGYAY YFYSVKG (SEQ ID NO: 40) | MERRIGTRRM TENAEYKY (SEQ ID NO: 41) |

TABLE 1-continued hIL12RB ECD Generated VHHs and CDRS

| Name | Sequence (CDRs Underlined) | CDR1 | CDR2 | CDR3 |
|---|---|---|---|---|
| hIL12Rb1_VHH7 | QVQLQESGGGSVQAGGSLRLSCAVSG<u>YDYCGYDVR</u>WYRRAPGKEREFVS<u>GIDSDGSTSYADSVKG</u>RFTISQDNAENTSYLHMFSLKPEDTAMYYCK<u>TESPAGESAWCRNFRGMDY</u>WGKGTQVTVSS (SEQ ID NO: 8) | YDYCGYDVR (SEQ ID NO: 42) | GIDSDGSTSYADSVKG (SEQ ID NO: 43) | ESPAGESAWCRNFRGMDY (SEQ ID NO: 44) |
| hIL12Rb1_VHH8 | QVQLQESGGGSVQAGGSLRLSCVASG<u>YSYCGYDMM</u>WYRQAPGKEREFVA<u>LITSDYSIRYEDSVEG</u>RFSISRDNAKNTGYLLMSNLTPADTAIYYCK<u>TSTAARESSWCRSRYRVAS</u>WGQGTQVTVSS (SEQ ID NO: 9) | YSYCGYDMM (SEQ ID NO: 45) | LITSDYSIRYEDSVEG (SEQ ID NO: 46) | STAARESSWCRSRYRVAS (SEQ ID NO: 47) |
| hIL12Rb1_VHH9 | QVQLQESGGGSVQAGGSLRLSCVASG<u>YSYCGYDMM</u>WYRQAPGKEREFVA<u>LITSDYSIRYEDSVEG</u>RFSISRDNAKNTGYLLMSNLTPADTAIYYCK<u>TSTAARESGWCRSRYRVAS</u>WGQGTQVTVSS (SEQ ID NO: 10) | YSYCGYDMM (SEQ ID NO: 48) | LITSDYSIRYEDSVEG (SEQ ID NO: 49) | STAARESGWCRSRYRVAS (SEQ ID NO: 50) |
| hIL12Rb1_VHH10 | QVQLQESGGGSVQAGGSLRLSCAVSG<u>YDYCGYDVR</u>WYRQAPGKEREFVS<u>GIDSDGSTSYADSVKG</u>RFTISQDNAENTSYLHMFSLKPEDTAMYYCK<u>TESPAGESAWCRNFRGMDY</u>WGKGTQVTVSS (SEQ ID NO: 11) | YDYCGYDVR (SEQ ID NO: 51) | GIDSDGSTSYADSVKG (SEQ ID NO: 52) | ESPAGESAWCRNFRGMDY (SEQ ID NO:53) |
| hIL12Rb1_VHH11 | QVQLQESGGGSVQAGGSLRLSCAVSG<u>YDYCGYDVR</u>WYRQAPGKEREFVS<u>GIDSDGSTSYADSVKG</u>RFTISQDNAENTSYLHMFSLKPEDTAMYYCK<u>TESPAGESAWCRNFRGMDY</u>WGKGTQVTVSS (SEQ ID NO: 12) | YDYCGYDVR (SEQ ID NO: 54) | GIDSDGSTSYADSVKG (SEQ ID NO: 55) | ESPAGESAWCRNFRGMDY (SEQ ID NO: 56) |
| hIL12Rb1_VHH12 | QVQLQESGGGSVQAGGSLRLSCTASG<u>YTYSSAFMA</u>WFRQAPGKEREGVA<u>AIYTRDGGTVYADSVKG</u>RFTISQDNAKNTLYLQMNSLKPEDTAMYYCAA<u>KMPQPGRASLLDSQTYDY</u>WGQGTQVTVSS (SEQ ID NO: 13) | YTYSSAFMA (SEQ ID NO: 57) | AIYTRDGGTVYADSVKG (SEQ ID NO: 58) | KMPQPGRASLLDSQTYDY (SEQ ID NO: 59) |
| hIL12Rb1_VHH13 | QVQLQESGGGSVQAGGFLRLSCVASG<u>YGYCGYDMS</u>WYRQAPGKEREFVA<u>LITSERVISYEDSVKG</u>RFSISRDNAENTGYLEMNRLTPDDTAIYYCKT<u>SAAARESSWCRSRYRVAS</u>WGQGTQVTVSS (SEQ ID NO: 14) | YGYCGYDMS (SEQ ID NO: 60) | LITSERVISYEDSVKG (SEQ ID NO: 61) | SAAARESSWCRSRYRVAS (SEQ ID NO: 62) |
| hIL12Rb1_VHH14 | QVQLQESGGGSVQAGGSLRLSCAVSG<u>YDYCGYDVR</u>WYRRAPGKEREFVS<u>GIDSDGSTSYADSVKG</u>RFTISQDNAENTSYLHMFSLKPEDTAMYYCK<u>TESPAGESAWCRNFRGMDY</u>WGKGTQVTVSS (SEQ ID NO: 15) | YDYCGYDVR (SEQ ID NO: 63) | GIDSDGSTSYADSVKG (SEQ ID NO: 64) | ESPAGESAWCRNFRGMDY (SEQ ID NO: 65) |

TABLE 1-continued hIL12RB ECD Generated VHHs and CDRS

| Name | Sequence (CDRs Underlined) | CDR1 | CDR2 | CDR3 |
|---|---|---|---|---|
| hIL12Rb1_VHH15 | QVQLQESGGGSVQAGGSLR LSCAVSGYDYCGYDVRWY RQAPGKEREFVSGINSDGST SYADSVKGRFTISQDNAENT SYLHMFSLKPEDTAMYYCK TESPAGESAWCRNFRGMDY WGKGTQVTVSS (SEQ ID NO: 16) | YDYCGYDVR (SEQ ID NO: 66) | GINSDGSTSY ADSVKG (SEQ ID NO: 67) | ESPAGESAWC RNFRGMDY (SEQ ID NO: 68) |
| hIL12Rb1_VHH16 | QVQLQESGGGSVQAGGSLR LSCTASGYTYSSAFMAWFR QAPGKEREGVAAMYTRDG GTVYADSVKGRFTISQDNA KNTLYLQIHTLKAEDTAMY YCAAKIPQPGRASLLDSQTY DYWGQGTQVTVSS (SEQ ID NO: 17) | YTYSSAFMA (SEQ ID NO: 69) | AMYTRDGGT VYADSVKG (SEQ ID NO: 70) | KIPQPGRASLL DSQTYDY (SEQ ID NO: 71) |
| hIL12Rb1_VHH17 | QVQLQESGGGSVQAGGFLR LSCVASGYGYCGYDMSWY RQVPGKEREFVALITSDRSV SYEDSVKGRFSISRDNAKNT AYLEMNRLTPDDTAIYYCK TSTAARENNWCRSRYRIAS WGQGTQVTVSS SEQ ID NO: 18) | YGYCGYDMS (SEQ ID NO: 72) | LITSDRSVSYE DSVKG (SEQ ID NO: 73) | STAARENNWC RSRYRIAS (SEQ ID NO: 74) |
| hIL12Rb1_VHH18 | QVQLQESGGGSVQAGGSLR LSCAASRYTYTNNFMAWFRK QAPGKEREGVAAIYTGDGY AYYFDSVKGRFTISQDNDK NMLYLQMNSLKPEDTAMY YCAAMERRSGRRRMTENA EYKYWGQGTQVTVSS (SEQ ID NO: 19) | YTYTNNFMA (SEQ ID NO: 75) | AIYTGDGYAY YFDSVKG (SEQ ID NO: 76) | MERRSGRRRM TENAEYKY (SEQ ID NO: 77) |
| hIL12Rb1_VHH19 | QVQLQESGGGSVQAGGSLR LSCAVSGYDYCGYDVRWY RQAPGKEREFVSGINSDGST SYADSVKGRFTISQDNAENT SYLHMFSLKPEDTAMYYCK TEGPAGESAWCRNFRGMD YWGKGTQVTVSS (SEQ ID NO: 20) | YDYCGYDVR (SEQ ID NO: 78) | GINSDGSTSY ADSVKG (SEQ ID NO: 79) | EGPAGESAWC RNFRGMDY (SEQ ID NO: 80) |
| hIL12Rb1_VHH20 | QVQLQESGGGSVQAGGSLR LSCTASGYTYSSAFMAWFR QAPGKEREGVAAIYTRDGS PVYADSLKGRFTISQDNAK NTLHLQMNSLKPEDTAMY YCAAKIPEPGRISLLDSQTY DYWGHGTQVTVSS (SEQ ID NO: 21) | YTYSSAFMA (SEQ ID NO: 81) | AIYTRDGSPV YADSLKG (SEQ ID NO: 82) | KIPEPGRISLLD ISQTYDY (SEQ ID NO: 83) |
| hIL12Rb1_VHH21 | QVQLQESGGGSVQAGGSLR LSCTASGYTYSSAFMAWFR QAPGKEREGVAAMYTRDG GTVYADSVKGRFTISQDNA KNTLYLQMNSLKTEDTAM YYCAAKIPQPGRASLLDSQT YDYWGQGTQVTVSS (SEQ ID NO: 22) | YTYSSAFMA (SEQ ID NO: 84) | AMYTRDGGT VYADSVKG (SEQ ID NO: 85) | KIPQPGRASLL DSQTYDY (SEQ ID NO: 86) |
| hIL12Rb1_VHH22 | QVQLQESGGGSVQAGGSLR LSCTASGYTYSSAFMAWFR QAPGKEREGVAAIYTRDGG TVYADSVKGRFTISQDNAK NTLYLQMNSLKAEDTAMY YCAAKIPQPGRASLLDSQTY DYWGQGTQVTVSS SEQ ID NO: 23) | YTYSSAFMA (SEQ ID NO: 87) | AIYTRDGGTV YADSVKG (SEQ ID NO: 88) | KIPQPGRASLL DSQTYDY (SEQ ID NO: 89) |

In some embodiments, the foregoing sets of CDRs are incorporated in a humanized VHH framework to provide "humanized" sdAb IL binding molecules.

The disclosure further provides methods of chemical or recombinant processes for the preparation of the IL12Rb1 binding molecules of the present disclosure.

The disclosure further provides nucleic acids encoding the IL12Rb1 binding molecules. Table 2A below provides examples of DNA sequences encoding IL12RB1 binding molecules as described herein.

TABLE 2

Nucleic Acid Sequences Encoding VHHs of Table 1

| Name | DNA Sequence |
|---|---|
| hIL12Rb1_VHH1 | CAGGTCCAGCTCCAGGAGTCTGGCGGTGGCTCAGTACAAGCTGGGGGCTCTCTGCGTTT GTCCTGTGTGGCGAGCGGGTACGGATACTGTGGGTACGACATGAGTTGGTACAGACAGG CCCCTGGCAAGGAACGTGAATTTGTGGCCCTCATCACTTCTGATCGCTCCATTAGCTAC GAGGATTCTGTCAAAGCTCGCTTTATCATTTCCCGCGACAACGCCGCTAACACTGGTTA TCTGGACATGACTAGACTGACCCCCGATGACACGGCCATTTACTATTGCAAGACCAGTG CAGCGGCCCGCGAATCTTCCTGGTGTCGCTCTCGCTACCGCGTGGCATCATGGGGCCAG GGTACTCAGGTCACCGTGTCTAGC (SEQ ID NO: 90) |
| hIL12Rb1_VHH2 | CAAGTCCAACTCCAGGAGTCTGGTGGGGGCTCTGTTCAAGCTGGCGGGTCCCTGCGCCT TTCCTGTACCGCCAGCGGCTACACGTACTCTAGCGCCTTCATGGCTTGGTTTCGGCAGG CCCCTGGAAAAGAGAGAGAGGGAGTGGCAGCTATCTACACTCGTGACGGCGGAACCGTG TACGCTGATAGTGTCAAGGGCCGCTTCACCATTTCCCAGGATAATGCCAAGAATATCCT GTATCTCCAGATGAACTCCCTTAAAGCCGAAGACACTGCGATGTACTATTGCGCAGCCA AAATCCCGCAGCCAGGCCGGGCTTCTTTGCTGGATAGCCAAACCTACGACTATTGGGGT CAAGGCACTCAGGTTACCGTGTCTTCC (SEQ ID NO: 91) |
| hIL12Rb1_VHH3 | CAGGTCCAGCTTCAGGAGAGCGGCGGAGGCTCCGTGCAGGCTGGGGGATCTTTGAGACT CAGCTGCGTGGCCAGTGGCTACTCTTACTGTGGGTACGACATGATGTGGTATCGCCAAG CGCCGGGCAAGGAACGTGAGTTCGTGGCGCTCATCACTTCCGACTACTCAATTCGTTAC GAGGATTCCGTTGAGGGCCGCTTCAGCATTTCTCGTGACAACGCGAAGAACACAGGATA CTTGCTGATGAGTAACCTCACCCCCGCCGATACCGCTATTTATTACTGCAAGACAAGTA CAGCTGCCAGGGAGAGCAGTTGGTGTCGGTCTCGCTATCGTGTGGCCTCCTGGGGACAG GGCACCCAAGTAACCGTGTCATCA (SEQ ID NO: 92) |
| hIL12Rb1_VHH4 | CAGGTGCAGCTCCAGGAATCTGGTGGGGGCAGTGTTCAGGCTGGTGGCAGCCTGAGACT TAGCTGCGTGGCTTCTGGCTATGGTTACTGTGGGTACGACATGAGCTGGTATCGGCAGA CCCCCGGAAAGGAGCGGGAGTTCGTAGCGCTCATCACAAGTGACCGCATCGCCTCCTAT GAAGACTCCGTTAAGGGTCGCTTTATCATTAGCCGGGACAATGCCAAGAACACAGGTTA CCTCGATATGACTCGGGTCACACCTGACGATACCGCTATCTATTACTGCAAGACTTCTG CGGCTGCCCGTGAAAACAGCTGGTGCCGCTCAAGATACCGGGTGGCCTCCTGGGGACAG GGAACTCAGGTCACCGTCTCTAGC (SEQ ID NO: 93) |
| hIL12Rb1_VHH5 | CAGGTGCAGTTGCAGGAGAGCGGAGGCGGATCTGTGCAGGCCGGTGGATTTCTGCGGCT GTCTTGCGTGGCGAGCGGCTATGGCTATTGCGGATACGACATGAGCTGGTATCGCCAGG TTCCGGGTAAGGAGCGTGAGTTCGTCGCTCTGATTACCTCTGATCGCTCTGTGTCCTAT GAGGACTCCGTTAAGGGTAGATTCTCTATCTCTCGCGATAATGCTAAGAACACAGCCTA CCTGGAGATGAACAGACTGACCCCCGACGATACCGCTGTCTATTACTGTAAGACCTCCA CAGCCGCTCGCGAGAATAACTGGTGCCGCTCTCGCTATAGAATCGCCTATTGGGGTCAG GGTACACAAGTTACCGTATCCTCC (SEQ ID NO: 94) |
| hIL12Rb1_VHH6 | CAGGTGCAGTTGCAGGAGAGTGGCGGGGGCTCTGTTCAGGCTGGTGGATCATTGCGTCT GAGCTGTGCTGCCTCCCGCTACACCTACACTAATAACTTCATGGCTTGGTTTAGACAAG CTCCTGGCAAGGAACGCGAAGGCGTTGCCGCGATTTATACCGGAGACGGTTACGCATAT TACTTCTATTCCGTGAAGGGCCGCTTCACAATCTCCCAGGATAACGACGAAAATATGCT CTACTTGCAGATGAACTCCCTCAAACCTGAGGACACGGCAATGTACTATTGTGCGGCTA TGGAGCGCCGTATCGGAACTCGCCGTATGACCGAAAACGCTGAGTATAAGTATTGGGGA CAAGGAACCCAGGTGACCGTATCCTCC (SEQ ID NO: 95) |
| hIL12Rb1_VHH7 | CAGGTCCAGTTGCAGGAGTCTGGTGGCGGAAGCGTGCAGGCTGGGGGCAGCCTCAGGCT GTCCTGTGCTGTGTCCGGGTACGACTACTGCGGCTACGACGTGCGCTGGTATCGCCGTG CCCCCGGCAAGGAGAGGGAGTTCGTCTCCGGGATTGATTCCGATGGCTCTACCAGTTAC GCAGATTCCGTCAAGGGTCGTTTTACCATTAGTCAGGATAACGCTGAGAACACAAGCTA TCTGCACATGTTCTCACTGAAGCCTGAGGATACGGCCATGTACTATTGCAAGACTGAGT CCCCCGCAGGTAATCCGCCTGGTGTCGTAACTTTCGCGGCATGGACTACTGGGGAAAG GGCACCCAGGTCACTGTGTCTTCT (SEQ ID NO: 96) |

TABLE 2-continued

Nucleic Acid Sequences Encoding VHHs of Table 1

| Name | DNA Sequence |
|---|---|
| hIL12Rb1_VHH8 | CAGGTGCAGCTCCAGGAATCAGGCGGTGGGTCCGTGCAGGCAGGAGGGAGTCTGCGCCT<br>GTCCTGTGTGGCCTCCGGTTACAGCTACTGCGGCTACAGATATGATGTGGTATAGGCAAG<br>CTCCAGGGAAGGAGCGTGAGTTCGTGGCCCTTATCACATCTGACTATTCCATCCGCTAC<br>GAGGACTCCGTGGAGGGAAGATTTTCAATCTCCAGAGACAACGCAAAGAACACCGGATA<br>CCTCCTGATGTCTAACCTGACCCCAGCCGACACGGCAATCTATTACTGTAAAACCTCCA<br>CAGCAGCGAGGGAGTCCAGCTGGTGCAGGTCCAGATACCGTGTTGCCTCCTGGGGACAG<br>GGCACTCAGGTGACGGTGAGTTCT<br>(SEQ ID NO: 97) |
| hIL12Rb1_VHH9 | CAGGTGCAGCTCCAGGAGTCCGGTGGCGGGAGCGTGCAGGCTGGCGGATCTCTGCGGCT<br>CAGTTGCGTCGCCTCAGGGTATTCCTATTGTGGCTACGATATGATGTGGTATCGTCAGG<br>CCCCCGGCAAGGAGCGCGAGTTCGTCGCCCTGATTACAAGCGATTATTCAATCCGTTAT<br>GAAGATTCCGTGGAGGGGCGCTTCTCCATCAGTCGCGACAACGCCAAAAACACTGGCTA<br>CCTTCTGATGTCAAACCTGACTCCCGCTGACACCGCGATCTACTATTGTAAAACCTCAA<br>CGGCTGCCCGCGAGTCCGGCTGGTGCCGGTCTAGGTATCGTGTGGCCAGCTGGGGGCAG<br>GGCACTCAGGTCACCGTGTCATCC<br>(SEQ ID NO: 98) |
| hIL12Rb1_VHH10 | CAGGTCCAGCTGCAAGAATCCGGTGGAGGCTCTGTGCAGGCGGGTGGGTCCCTGCGCCT<br>GTCTTGCGCCGTGTCTGGCTATGATTATTGCGGATATGACGTGCGCTGGTATCGCCAGG<br>CTCCCGGCAAGGAACGCGAGTTTGTCTCTGGGATTGACTCAGACGGCAGCACTAGCTAT<br>GCCGACTCCGTGAAAGGTCGCTTCACCATTTCCCAAGACAACGCCGAGAATACCAGCTA<br>TCTGCACATGTTCAGCCTCAAACCTGAAGATACTGCCATGTATTACTGTAAGACGGAGA<br>GTCCCGCAGGCAATCCGCTTGGTGTCGGAATTTCAGGGGAATGGACTACTGGGGCAAG<br>GGTACTCAAGTGACCGTAAGCTCT<br>(SEQ ID NO: 99) |
| hIL12Rb1_VHH11 | CAGGTGCAGCTCCAGGAGAGCGGCGGAGGCTCCGTGCAGGCGGGCGGGAGCCTGCGTCT<br>GTCTTGTGCCGTATCTGGCTATGACTATTGCGGTTACGACGTTCGCTGGTACAGGCAGG<br>CTCCGGGCAAGGAGCGTGAGTTTGTCAGCGGGATTGACAGTGACGGCTCCACCTCTTAT<br>GCGGATTCCGTGAAGGGACGCTTCACAATTTCCCAGGATAACGCAGAGAACACCTCCTA<br>CCTCCACATGTTCAGCCTCAAACCCGAAGATACTGCTATGTATTACTGTAAAACAGAGA<br>GCCCAGCCGGGAGTCTGCTTGGTGTCGTAACTTTCGCGGCATGGACTACTGGGGCAAG<br>GGAACCCAGGTGACCGTCTCTTCC<br>(SEQ ID NO: 100) |
| hIL12Rb1_VHH12 | CAGGTGCAACTCCAAGAGAGCGGAGGCGGGAGTGTTCAGGCCGGGGGCTCTCTGCGGCT<br>GTCCTGCACCGCCTCTGGTTACACCTACTCCAGCGCCTTCATGGCCTGGTTCCGGCAGG<br>CACCTGGCAAGGAACGCGAAGGCGTAGCCGCTATCTATACGCGCGATGGGGGTACAGTT<br>TATGCTGATAGCGTTAAAGGACGCTTCACTATCTCCCAGGACAACGCCAAAAACACCCT<br>GTACTTGCAGATGAACTCCCTCAAACCTGAAGATACGGCGATGTACTATTGTGCGGCAA<br>AGATGCCTCAGCCCGGACGCGCAAGTCTGCTTGACTCTCAAACTTATGATTACTGGGGC<br>CAAGGGACTCAGGTGACCGTTAGCTCC<br>(SEQ ID NO: 101) |
| hIL12Rb1_VHH13 | CAGGTGCAGTTGCAGGAAAGCGGCGGTGGCTCAGTCCAGGCCGGGGGCTTCTTGCGCTT<br>GAGTTGCGTGGCGAGCGGATATGGCTACTGTGGCTACGATATGAGCTGGTATCGTCAGG<br>CTCCGGGCAAGGAACGTGAGTTCGTCGCGCTCATCACTAGCGAAAGAGTCATCTCCTAC<br>GAAGACTCCGTTAAGGGCCGCTTTTCCATTTCTCGCGACAACGCCGAGAACACGGGCTA<br>CCTTGAAATGAATAGACTGACTCCCGACGATACTGCCATCTACTATTGCAAGACAAGCG<br>CCGCTGCACGCGAGTCCTCTTGGTGCAGGTCTCGCTACCGCGTGGCTTCTTGGGGGCAG<br>GGACCCAGGTGACCGTATCATCC<br>(SEQ ID NO: 102) |
| hIL12Rb1_VHH14 | CAGGTTCAACTCCAGGAGTCCGGGGCGGTTCCGTGCAGGCTGGGGGCTCCCTTAGACT<br>TAGCTGTGCCGTGTCTGGATACGATTACTGTGGGTATGACGTGCGGTGGTACAGACGCG<br>CTCCGGGAAGGAACGCGAGTTCGTGAGCGGAATTGATTCCGATGGCAGCACCTCCTAT<br>GCGGATTCTGTGAAGGGCCGCTTCACTATCTCTCAAGACAACGCCGAGAACACTAGCTA<br>CCTGCACATGTTCAGTCTGAAACCGGAGGATACCGCGATGTATTACTGTAAGACCGAGT<br>CTCCTGCTGGAGAGAGCGCGTGGTGCAGAAACTTCCGTGGAATGGACTATTGGGGTAAA<br>GGAACTCAGGTGACTGTGTCCAGT<br>(SEQ ID NO: 103) |
| hIL12Rb1_VHH15 | CAAGTGCAGCTCCAGGAATCTGGAGGCGGAAGCGTACAGGCCGGTGGCTCACTCCGGCT<br>TTCTTGCGCTGTGTCAGGTTACGACTATTGTGGATATGATGTCCGGTGGTATAGGCAAG<br>CGCCGGGAAGGAGCGCGAGTTCGTGAGCGGTATCAACTCTGACGGCTCCACCTCCTAC<br>GCCGACTCTGTCAAGGGCCGCTTTACAATTTCTCAGGACAACGCAGAGAACACCTCTTA<br>CCTGCACATGTTCAGCTTGAAGCCGGAGGACACCGCGATGTACTATTGTAAGACTGAGT<br>CCCCCGCTGGAGAGTCTGCATGGTGCCGTAATTTTCGCGGCATGGACTATTGGGGGAAA<br>GGTACTCAGGTTACCGTAAGCTCA<br>(SEQ ID NO: 104) |

TABLE 2-continued

Nucleic Acid Sequences Encoding VHHs of Table 1

Name | DNA Sequence
---|--- hIL12Rb1_VHH16
CAGGTACAGCTCCAGGAGAGTGGAGGCGGGTCAGTGCAGGCCGGGGGCTCACTGCGCTT
GAGCTGCACCGCGAGCGGTTACACCTACAGCTCCGCATTCATGGCTTGGTTCAGGCAAG
CCCCAGGCAAGGAGCGCGAGGGCGTGGCTGCCATGTATACCCGCGACGGGGGCACCGTG
TATGCCGATTCCGTGAAGGGCCGTTTCACCATCTCCCAGGATAACGCTAAGAACACCCT
CTACCTCCAGATCCACACTCTCAAAGCCGAAGACACGGCTATGTACTATTGCGCCGCGA
AGATCCCTCAACCTGGCAGGGCAAGCCTTCTGGACTCCCAGACGTATGACTATTGGGGC
CAGGGGACTCAGGTTACAGTGTCCAGC
(SEQ ID NO: 105)

hIL12Rb1_VHH17
CAGGTGCAGCTCCAGGAATCCGGCGGTGGGTCTGTGCAGGCAGGGGTTTTCTCCGCTT
GAGCTGTGTGGCTAGTGGATACGGTTATTGTGGATACGACATGAGCTGGTATCGCCAAG
TACCGGGCAAGGAGCGTGAGTTTGTGGCCCTCATCACCTCTGATCGCTCCGTGTCTTAT
GAGGACAGCGTGAAGGGCCGCTTCAGCATCAGTCGCGACAACGCCAAGAACACCGCTTA
TCTGGAAATGAACAGACTCACCCCGGATGACACAGCTATCTACTATTGCAAGACCTCCA
CAGCGGCCAGAGAGAATAACTGGTGCCGGTCCCGCTACCGCATCGCGTCCTGGGGCCAG
GGCACCCAGGTGACTGTCTCCTCT
(SEQ ID NO: 106)

hIL12Rb1_VHH18
CAGGTGCAGTTGCAGGAGTCTGGAGGGGGCAGCGTGCAGGCCGGAGGCTCCCTCCGCCT
CAGCTGCGCGGCCTCCCGGTACACCTACACCAATAACTTCATGGCATGGTTCAGGCAGG
CCCCAGGAAAGGAGCGTGAGGGGGTCGCCGCAATCTATACCGGAGACGGCTACGCCTAT
TACTTTGACTCCGTTAAAGGGCGTTTCACCATCAGTCAAGCAACGACAAAAACATGCT
CTACCTCCAGATGAATAGCTTGAAGCGGAGGATACCGCAATGTACTATTGTGCCGCGA
TGGAGAGACGCTCCGGTCGGCGTCGCATGACTGAAAATGCCGAGTACAAGTACTGGGGG
CAGGGGACTCAGGTGACCGTGAGCAGC
(SEQ ID NO : 107)

hIL12Rb1_VHH19
CAAGTTCAGCTCCAGGAGAGTGGAGGCGGTTCCGTACAGGCTGGCGGAAGTCTGCGCCT
CTCCTGCGCCGTCTCCGGTTACGACTATTGTGGGTACGACGTGCGCTGGTATAGACAGG
CTCCTGGAAAGGAGCGTGAGTTTGTGAGTGGCATCAACTCCGACGGTAGCACCTCCTAT
GCTGATTCTGTGAAGGGTCGCTTTACAATCTCACAGGACAACGCCGAAAACACTTCCTA
TCTGCACATGTTCAGCCTCAAGCCCGAAGACACCGCAATGTACTATTGTAAGACTGAAG
GTCCAGCTGGCGAGAGTGCATGGTGCAGGAATTTTAGGGGCATGGACTACTGGGGCAAG
GGCACCCAGGTCACCGTGTCTTCA
(SEQ ID NO: 108)

hIL12Rb1_VHH20
CAGGTGCAGTTGCAGGAATCAGGAGGCGGTTCTGTGCAGGCCGGAGGCAGCCTGCGTCT
GAGCTGCACCGCTTCTGGGTACACCTACTCAAGTGCCTTCATGGCCTGGTTTCGGCAAG
CGCCCGGCAAGGAACGCGAGGGAGTTGCGGCCATCTACACCAGGGACGGCAGTCCCGTG
TACGCTGACTCCCTGAAGGGCCGTTTCACCATCAGCCAGGATAACGCAAAGAACACCCT
GCACCTCCAGATGAACAGCCTGAAACCTGAGGACACAGCTATGTATTACTGCGCGGCCA
AAATCCCTGAGCCTGGAAGAATCAGCCTCCTTGACTCCCAGACCTACGACTACTGGGGT
CACGGCACTCAGGTGACTGTGTCTTCT
(SEQ ID NO: 109)

hIL12Rb1_VHH21
CAGGTTCAACTCCAAGAGTCTGGAGGCGGGTTCCGTGCAGGCTGGGGGCTCCCTCAGACT
GTCCTGTACTGCGTCAGGGTACACCTACAGCTCCGCTTTCATGGCTTGGTTCCGGCAAG
CTCCGGGCAAGGAGCGCGAGGGCGTGGCCGCGATGTATACCCGCGACGGTGGCACCGTG
TACGCCGACTCTGTTAAAGGCCGCTTCACCATCTCCCAGGATAACGCCAAGAACACCCT
GTACCTCCAGATGAACTCTTTGAAGACCGAGGATACCGCTATGTACTATTGCGCCGCAA
AAATTCCCCAGCCGGGCCGTGCTTCCCTTCTGGACAGCCAAACCTATGATTACTGGGGC
CAGGGCACACAGGTGACCGTGTCCTCC
(SEQ ID NO: 110)

hIL12Rb1_VHH22
CAGGTGCAACTTCAGGAATCTGGCGGTGGCAGCGTGCAGGCTGGTGGCTCCCTGCGCCT
GAGCTGTACTGCTTCCGGCTACACATACTCTAGTGCGTTCATGGCCTGGTTCAGGCAAG
CTCCGGGAAAGGAGCGCGAGGGTGTGGCGCCATTTATACACGCGACGGAGGCACCGTG
TACGCTGACTCTGTCAAGGGCCGCTTCACCATCTCACAGGACAATGCAAAAATACCCT
CTACCTTCAGATGAACAGCCTGAAGGCAGAGGACACAGCAATGTATTACTGTGCAGCCA
AGATCCCACAACCCGGACGCGCGTCCTCCTGGATTCACAGACCTACGACTACTGGGGC
CAGGGCACGCAGGTTACTGTATCAAGC
(SEQ ID NO: 111)

In some embodiments, the IL12RB1 binding molecule comprises a single domain antibody (sdAb) that specifically binds to the extracellular domain of murine IL12RB1 (mIL12RB1).

In some embodiments, the IL12RB1 binding molecule consists of, optionally consists essentially of, or optionally comprises a single domain antibody (sdAb) having at least 80%, alternatively at least 85%, alternatively at least 90%, alternatively at least 95%, alternatively at least 98%, alternatively at least 99% identity (or being identical except for 1, 2, 3, or 4 amino acids that optionally are conserved substitutions) or 100% identity to a polypeptide sequence of any one of SEQ ID NOS:112-134, as shown in Table 3 below.

TABLE 3 mIL12RB ECD Generated VHHs

| Name | VHH Amino Acid Sequence (CDRs underlined) | SEQ ID NO |
|---|---|---|
| mIL12Rb1_VHH1 | QVQLQESGGGSVQAGGSLRLSCTASGYTYSSAFMAWFRQAPGKE REGVAAIYTRDGGTVYADSVKGRFTISQDNAKNTLYLQMNSLKA EDTAMYYCAAKIPQPGRASLLDSQTYDYWGQGTQVTVSS | 112 |
| mIL12Rb1_VHH2 | QVQLQESGGGSVQAGGSLRLSCAVSGYDYCGYDVRWYRQAPGK EREFVSGIDSDGSTSYADSVKGRFTISQDNAENTSYLHMFSLK PEDTAMYYCKTESPAGESAWCRNFRGMDYWGKGTQVTVSS | 113 |
| mIL12Rb1_VHH3 | QVQLQESGGGSVQAGGSLRLSCVASGYSYCGYDMMWYRQAPG KEREFVALITSDYSIRYEDSVEGRFSISRDNAKNTGYLLMSN LTPADTAIYYCKTSTAARESSWCRSRYRVASWGQGTQVTVSS | 114 |
| mIL12Rb1_VHH4 | QVQLQESGGGSVQAGGSLRLSCAASRYTYTNNFMAWFRQAPGK EREGVAAIYTGDGYAYYFDSVKGRFTISQDNDKNMLYLQMNSL KPEDTAMYYCAAMERRSGRRRMTENAEYKYWGQGTQVTVSS | 115 |
| mIL12Rb1_VHH5 | QVQLQESGGGSVQAGETLRLSCTVSGFTIDDSEMGWYRQAPGHE CELVASGSSDDDTYYVDSVKGRFTISLDNAKNMVYLQMNSLKPE DTAVYYCATGPTYPPKDGDCAHWGQGTQVTVSS | 116 |
| mIL12Rb1_VHH6 | QVQLQESGGGSVQAGGSLRLSCTASGYTYSSAFMAWFRQAPGKE REGVAAIYTRDGSPVYADSLKGRFTISQDNAKNTLHLQMNSLKP EDTAMYYCAAKIPEPGRISLLDSQTYDYWGHGTQVTVSS | 117 |
| mIL12Rb1_VHH7 | QVQLQESGGGSVQAGGSLRLSCAVSGYDYCGYDVRWYRRAPGK EREFVSGIDSDGSTSYADSVKGRFTISQDNAENTSYLHMFSLK PEDTAMYYCKTESPAGESAWCRNFRGMDYWGKGTQVTVSS | 118 |
| mIL12Rb1_VHH8 | QVQLQESGGGSVQAGGFLRLSCVASGYGYCGYDMSWYRQAPGK EREFVALITSERVISYEDSVKGRFSISRDNAENTGYLEMNRLT PDDTAIYYCKTSAAARESSWCRSRYRVASWGQGTQVTVSS | 119 |
| mIL12Rb1_VHH9 | QVQLQESGGGSVQAGGSLRLSCVASGYGYCGYDMSWYRQAPGK EREFVALITSDRSISYEDSVKARFIISRDNAANTGYLDMTRLT PDDTAIYYCKTSAAARESSWCRSRYRVASWGQGTQVTVSS | 120 |
| mIL12Rb1_VHH10 | QVQLQESGGGSVQAGGSLRLSCVASGYDYCGYDVRWYRQAPGK EREFVSGIDSDGSTSYADSVKGRFTISQDNAENTSYLHMFSLK PEDTAMYYCKTESPAGESAWCRNFRGMDYWGKGTQVTVSS | 121 |
| mIL12Rb1_VHH11 | QVQLQESGGGSVQAGGSLRLSCVASGYSYCGYDMMWYRQAPG KEREFVALITSDYSIRYEDSVEGRFSISRDNAKNTGYLLMSN LTPADTAIYYCKTSTAARESSWCRSRYRVASWGQGTQVTVSS | 122 |
| mIL12Rb1_VHH12 | QVQLQESGGGSVQAGGSLRLSCAASRYTYTNNFMAWFRQAPGK EREGVAAIYTGDGYAYYFYSVKGRFTISQDNDENMLYLQMNSL KPEDTAMYYCAAMERRIGTRRMTENAEYKYWGQGTQVTVSS | 123 |
| mIL12Rb1_VHH13 | QVQLQESGGGSVQAGGSLRLSCVASGYSYCGYDMMWYRQAPG KEREFVALITSDYSIRYEDSVEGRFSISRDNAKNTGYLLMSN LTPADTAIYYCKTSTAARESGWCRSRYRVASWGQGTQVTVSS | 124 |
| mIL12Rb1_VHH14 | QVQLQESGGGSVQAGGSLRLSCVASGYDYCGYDVRWYRQAPGK EREFVSGINSDGSTSYADSVKGRFTISQDNAENTSYLHMFSLK PEDTAMYYCKTESPAGESAWCRNFRGMDYWGKGTQVTVSS | 125 |
| mIL12Rb1_VHH15 | QVQLQESGGGSVQAGGFLRLSCVASGYGYCGYDMSWYRQVPGK EREFVALITSDRSVSYEDSVKGRFSISRDNAKNTAYLEMNRLT PDDTAVYYCKTSTAARENNWCRSRYRIAYWGQGTQVTVSS | 126 |
| mIL12Rb1_VHH16 | QVQLQESGGGSVQAGGSLRLSCVASGYDYCGYDVRWYRQAPGK EREFVSGINSDGSTSYADSVKGRFTISQDNAENTSYLHMFSLK PEDTAMYYCKTEGPAGESAWCRNFRGMDYWGKGTQVTVSS | 127 |
| mIL12Rb1_VHH17 | QVQLQESGGGSVQAGGSLRLSCTASGYTYSSAFMAWFRQAPGKE REGVAAMYTRDGGTVYADSVKGRFTISQDNAKNTLYLQIHTLKA EDTAMYYCAAKIPQPGRASLLDSQTYDYWGQGTQVTVSS | 128 |
| mIL12Rb1_VHH18 | QVQLQESGGGSVQAGGSLRLSCTASGYTYSSAFMAWFRQAPGKE REGVAAMYTRDGGTVYADSVKGRFTISQDNAKNTLYLQMNSLK TEDTAMYYCAAKIPQPGRASLLDSQTYDYWGQGTQVTVSS | 129 |
| mIL12Rb1_VHH19 | QVQLQESGGGSVQAGGFLRLSCVASGYGYCGYDMSWYRQVPGK EREFVALITSDRSVSYEDSVKGRFSISRDNAKNTAYLEMNRLT PDDTAIYYCKTSTAARENNWCRSRYRIASWGQGTQVTVSS | 130 |

TABLE 3-continued mIL12RB ECD Generated VHHs

| Name | VHH Amino Acid Sequence (CDRs underlined) | SEQ ID NO |
|---|---|---|
| mIL12Rb1_VHH20 | QVQLQESGGGSVQAGGSLRLSCVASGYGYCGYDMSWYRQTPGK EREFVALITSDRIASYEDSVKGRFIISRDNAKNTGYLDMTRVT PDDTAIYYCKTSAAARENSWCRSRYRVASWGQGTQVTVSS | 131 |
| mIL12Rb1_VHH21 | QVQLQESGGGSVQAGGSLRLSCAVSGYDYCGYDVRWYRRAPGK EREFVSGIDSDGSTSYADSVKGRFTISQDNAENTSYLHMFSLK PEDTAMYYCKTESPAGESAWCRNFRGMDYWGKGTQVTVSS | 132 |
| mIL12Rb1_VHH22 | QVQLQESGGGSVQAGGSLRLSCTASGYTYSSAFMAWFRQAPGKE REGVAAIYTRDGGTVYADSVKGRFTISQDNAKNILYLQMNSLKA EDTAMYYCAAKIPQPGRASLLDSQTYDYWGQGTQVTVSS | 133 |
| mIL12Rb1_VHH23 | QVQLQESGGGSVQAGGSLRLSCTASGYTYSSAFMAWFRQAPGKE REGVAAIYTRDGGTVYADSVKGRFTISQDNAKNTLYLQMNSLKP EDTAMYYCAAKMPQPGRASLLDSQTYDYWGQGTQVTVSS | 134 |

In some embodiments, the IL12RB1 binding molecule is a sdAb, the sdAb comprising a set of CDRs corresponding to CDR1, CDR2, and CDR3 as shown in a row of Table 4 below.

In some embodiments, the IL12RB1 binding molecule comprises a CDR1, a CDR2, and a CDR3 as described in a row of Table 1 below, in which the CDR1, CDR2, and CDR3 can each, independently, comprise at least 90% (e.g., 91%, 92%, 93%, 94%, 95%, 96%, 97%, 98%, 99%, or 100%) sequence identity, or have 0, 1, 2, or 3 amino acid changes, optionally conservative amino acid changes, relative to the sequence described in a row of Table 5 below.

TABLE 5 mIL12RB1 VHH CDRs

| CDR1 (AA Seq) | SEQ ID NO | CDR2 (AA Seq) | SEQ ID NO | CDR3 (AA Seq) | SEQ ID NO |
|---|---|---|---|---|---|
| YTYSSAFMA | 135 | AIYTRDGGTVYADSVKG | 136 | KIPQPGRASLLDSQTYDY | 137 |
| YDYCGYDVR | 138 | GIDSDGSTSYADSVKG | 139 | ESPAGESAWCRNFRGMDY | 140 |
| YSYCGYDMM | 141 | LITSDYSIRYEDSVEG | 142 | STAARESSWCRSRYRVAS | 143 |
| YTYTNNFMA | 144 | AIYTGDGYAYYFDSVKG | 145 | MERRSGRRRMTENAEYKY | 146 |
| FTIDDSEMG | 147 | SGSSDDDTYVVDSVKG | 148 | GPTYPPKDGDCAH | 149 |
| YTYSSAFMA | 150 | AIYTRDGSPVYADSLKG | 151 | KIPEPGRISLLDSQTYDY | 152 |
| YDYCGYDVR | 153 | GIDSDGSTSYADSVKG | 154 | ESPAGESAWCRNFRGMDY | 155 |
| YGYCGYDMS | 156 | LITSERVISYEDSVKG | 157 | SAAARESSWCRSRYRVAS | 158 |
| YGYCGYDMS | 159 | LITSDRSISYEDSVKA | 160 | SAAARESSWCRSRYRVAS | 161 |
| YDYCGYDVR | 162 | GIDSDGSTSYADSVKG | 163 | ESPAGESAWCRNFRGMDY | 164 |
| YSYCGYDMM | 165 | LITSDYSIRYEDSVEG | 166 | STAARESSWCRSRYRVAS | 167 |
| YTYTNNFMA | 168 | AIYTGDGYAYYFYSVKG | 169 | MERRIGTRRMTENAEYKY | 170 |
| YSYCGYDMM | 171 | LITSDYSIRYEDSVEG | 172 | STAARESGWCRSRYRVAS | 173 |
| YDYCGYDVR | 174 | GINSDGSTSYADSVKG | 175 | ESPAGESAWCRNFRGMDY | 176 |
| YGYCGYDMS | 177 | LITSDRSVSYEDSVKG | 178 | STAARENNWCRSRYRIAY | 179 |
| YDYCGYDVR | 180 | GINSDGSTSYADSVKG | 181 | EGPAGESAWCRNFRGMDY | 182 |
| YTYSSAFMA | 183 | AMYTRDGGTVYADSVKG | 184 | KIPQPGRASLLDSQTYDY | 185 |
| YTYSSAFMA | 186 | AMYTRDGGTVYADSVKG | 187 | KIPQPGRASLLDSQTYDY | 188 |
| YGYCGYDMS | 189 | LITSDRSVSYEDSVKG | 190 | STAARENNWCRSRYRIAS | 191 |
| YGYCGYDMS | 192 | LITSDRIASYEDSVKG | 193 | SAAARENSWCRSRYRVAS | 194 |
| YDYCGYDVR | 195 | GIDSDGSTSYADSVKG | 196 | ESPAGESAWCRNFRGMDY | 197 |

TABLE 5-continued mIL12RB1 VHH CDRs

| CDR1 (AA Seq) | SEQ ID NO | CDR2 (AA Seq) | SEQ ID NO | CDR3 (AA Seq) | SEQ ID NO |
|---|---|---|---|---|---|
| YTYSSAFMA | 198 | AIYTRDGGTVYADSVKG | 199 | KIPQPGRASLLDSQTYDY | 200 |
| YTYSSAFMA | 201 | AIYTRDGGTVYADSVKG | 202 | KMPQPGRASLLDSQTYDY | 203 |

In some embodiments, the foregoing sets of CDRs are incorporated in a humanized VHH framework to provide "humanized" sdAb IL binding molecules.

The disclosure further provides methods of chemical or recombinant processes for the preparation of the IL binding molecules of the present disclosure.

The disclosure further provides nucleic acids encoding the IL12RB1 binding molecules. Table 5 below provides examples of DNA sequences encoding IL12RB1 binding molecules as described herein.

TABLE 5

Nucleic Acid sequences Encoding VHHs of Table 3

| Name | DNA Sequence | SEQ ID NO |
|---|---|---|
| mIL12Rb1_VHH1 | CAGGTGCAGCTCCAGGAAAGCGGGGGAGGTTCCGTCCAGGCC GGTGGCTCCCTCCGCCTGTCATGCACAGCGAGCGGTTACACGT ATAGCTCCGCCTTTATGGCCTGGTTTAGACAGGCCCCAGGGAA AGAACGTGAGGGAGTGGCTGCAATTTACACCCGCGATGGCGG GACTGTTTACGCCGATAGCGTCAAGGGTCGCTTTACCATCAGC CAGGACAACGCTAAAAACACCCTCTATCTCCAGATGAATAGC CTGAAGGCCGAGGACACTGCGATGTATTACTGCGCCGCTAAG ATCCCTCAACCTGGCCGCGCCAGCTTGCTGGATAGCCAGACAT ACGATTACTGGGGTCAGGGAACACAAGTGACGGTCAGCAGC | 204 |
| mIL12Rb1_VHH2 | CAGGTGCAGCTCCAGGAGAGCGGCGGGGGCTCCGTACAGGCC GGTGGATCACTCCGCCTGAGCTGTGCTGTGAGCGGGTACGAC TATTGCGGATACGACGTGCGCTGGTATCGCCAAGCTCCAGGG AAGGAAAGGGAGTTCGTGAGCGGAATTGATTCCGATGGCTCC ACCAGTTATGCCGACTCCGTTAAAGGAAGGTTTACCATCTCCC AAGATAACGCCGAGAACACCTCCTATCTGCATATGTTTTCCCT GAAACCCGAGGATACCGCTATGTATTACTGTAAGACAGAGAG CCCTGCCGGAGAGTCCGCCTGGTGCCGCAACTTTCGGGGCAT GGACTACTGGGGAAAGGGCACCCAGGTGACAGTGTCTAGC | 205 |
| mIL12Rb1_VHH3 | CAGGTGCAGCTGCAAGAATCAGGAGGTGGATCTGTGCAAGCT GGGGGCTCTTTGCGCCTGTCCTGTGTCGCCTCCGGCTATAGCT ATTGCGGCTATGACATGATGTGGTACAGGCAAGCCCCAGGTA AGGAGAGGGAGTTTGTGGCTCTCATCACCTCCGACTACAGCA TTCGCTATGAAGATAGTGTCGAGGGACGCTTCTCCATTTCTCG CGACAACGCGAAGAACACTGGCTATTTGCTGATGAGTAACCT CACCCCCGCCGACACCGCGATCTACTATTGCAAAACATCTACC GCCGCTCGGGAAAGTAGCTGGTGTAGGTCACGTTATAGGGTC GCTTCCTGGGGTCAGGGCACGCAGGTGACCGTCTCATCC | 206 |
| mIL12Rb1_VHH4 | CAGGTGCAGTTGCAGGAGAGCGGAGGCGGATCTGTGCAGGCA GGCGGAAGCCTCCGCCTGTCTTGCGCCGCTTCCCGGTACACCT ACACAAATAACTTTATGGCATGGTTCCGCCAAGCGCCCGGCA AGGAGCGCGAGGGTGTCGCGGCCATTTACACAGGTGATGGCT ACGCCTATTACTTCGACTCCGTGAAAGGCAGGTTCACGATCTC CCAGGATAACGACAAGAATATGTTGTATCTTCAGATGAACTCT CTGAAACCTGAGGACACCGCTATGTACTATTGTGCAGCTATGG AACGCAGGTCAGGCAGGCGCAGGATGACCGAGAACGCCGAG TACAAGTACTGGGGCCAGGGCACCCAGGTGACCGTGTCTTCA | 207 |

TABLE 5-continued

Nucleic Acid sequences Encoding VHHs of Table 3

| Name | DNA Sequence | SEQ ID NO |
|---|---|---|
| mIL12Rb1_VHH5 | CAGGTGCAGCTCCAGGAGTCTGGAGGCGGTTCCGTCCAGGCCGGGGAAACGCTCCGGCTTAGCTGCACCGTCTCCGGTTTCACCATTGATGACTCCGAAATGGGTTGGTATCGCCAAGCGCCCGGCCATGAGTGCGAACTGGTGGCCAGCGGAAGTTCCGACGATGACACCTATTACGTGGACTCAGTGAAGGGTCGCTTTACGATCTCTCTGGATAACGCCAAAAACATGGTGTACCTCCAGATGAACTCACTCAAGCCAGAGGATACAGCAGTTTATTACTGTGCCACTGGACCTACATACCCTCCCAAGGATGGTGACTGCGCACACTGGGGTCAAGGCACCCAGGTCACTGTCTCCTCC | 208 |
| mIL12Rb1_VHH6 | CAAGTCCAGCTCCAGGAGTCTGGGGGAGGCTCAGTGCAAGCTGGTGGATCTCTTCGCCTGTCTTGCACCGCTTCTGGGTACACCTATAGCTCTGCCTTCATGGCCTGGTTTAGGCAAGCGCCTGGCAAGGAGCGGGAGGGCGTCGCCGCTATCTACACCCGCGACGGCAGTCCGGTTTATGCCGACTCCCTGAAGGGTAGATTTACTATCTCTCAGGATAATGCAAAGAATACGCTGCACTTGCAGATGAACTCCCTCAAACCCGAGGACACGGCCATGTATTACTGTGCTGCAAAAATCCCAGAGCCTGGTCGGATCTCCTCCTGGATTCACAGACCTACGACTACTGGGGCCACGGCACCCAGGTGACAGTCTCTTCC | 209 |
| mIL12Rb1_VHH7 | CAGGTGCAGCTCCAGGAGTCCGGTGGCGGAAGCGTGCAGGCCGGTGGCTCCCTGCGGTTGAGTTGCGCGGTCTCAGGTTACGATTATTGTGGCTACGACGTGCGCTGGTATAGACGCGCTCCTGGCAAGGAGCGTGAGTTCGTGTCTGGCATCGACTCCGATGGCTCTACTTCATACGCTGATTCCGTCAAAGGCCGTTTCACCATCTCTCAGGATAACGCCGAGAACACCTCCTACCTTCACATGTTCTCTCTGAAGCCCGAGGATACTGCAATGTATTACTGTAAGACTGAGTCTCCTGCCGGAGAATCCGCCTGGTGTCGTAACTTTCGTGGCATGGACTACTGGGGTAAGGGAACCCAGGTGACTGTATCTTCC | 210 |
| mIL12Rb1_VHH8 | CAGGTCCAGTTGCAGGAGTCTGGTGGAGGCTCCGTCCAAGCTGGGGGCTTTCTTAGGCTGTCATGTGTGGCATCCGGCTATGGGTATTGTGGCTATGATATGTCCTGGTATAGACAAGCGCCCGGCAAGGAGCGCGAGTTCGTGGCGCTGATTACCAGCGAGCGCGTTATCAGCTACGAGGACTCCGTCAAAGGCAGATTCTCCATCTCACGCGACAACGCCGAGAACACAGGCTATCTGGAAATGAATCGTTTGACACCTGATGACACCGCTATCTACTATTGCAAGACCTCTGCGGCTGCGCGTGAGTCTAGCTGGTGCCGTTCCCGCTATAGAGTGGCTTCTTGGGGTCAGGGAACCCAGGTGACAGTCTCCAGC | 211 |
| mIL12Rb1_VHH9 | CAGGTACAGCTCCAGGAGTCTGGAGGCGGGAGCGTGCAGGCAGGCGGTTCCCTGCGTCTGTCCTGCGTCGCCTCTGGGTATGGGTACTGCGGCTACGATATGTCCTGGTATCGTCAGGCTCCCGGCAAAGAAAGAGAGTTCGTAGCCCTCATCACATCTGACCGGAGCATTTCCTACGAAGACTCCGTCAAGGCCCGCTTCATTATCTCACGGGATAACGCAGCCAACACCGGATACCTGGACATGACTCGCCTGACCCCCGATGACACTGCTATCTATTACTGCAAGACGAGCGCGGCAGCTCGCGAGAGTTCTTGGTGCCGGTCCCGGTACAGGGTGGCGTCCTGGGGCCAGGGGACTCAGGTCACCGTCTCCTCC | 212 |
| mIL12Rb1_VHH10 | CAGGTGCAACTCCAGGAGAGTGGAGGTGGCTCAGTACAGGCCGGGGGAAGCCTCCGTCTGAGCTGTGCCGTGTCCGGCTACGATTACTGTGGTTACGACGTGCGGTGGTATCGCCAGGCCCCTGGTAAGGAAAGAGAGTTCGTGTCCGGCATCGACAGCGATGGTAGCACATCTTACGCCGACTCCGTGAAGGGCCGCTTCACAATCTCCCAGGACAACGCCGAAAACACGTCTTACCTCCATATGTTTTCCCTGAAACCTGAAGACACCGCTATGTATTACTGCAAGACCGAGTCTCCCGCTGGCGAGTCAGCATGGTGTAGGAACTTTCGCGGCATGGACTATTGGGGTAAGGGCACCCAGGTGACGGTGAGTTCT | 213 |
| mIL12Rb1_VHH11 | CAGGTGCAGCTCCAGGAAAGCGGCGGGGAAGCGTGCAGGCAGGAGGCTCCCTTCGGTTGAGCTGCGTGGCCAGCGGCTACAGCTACTGCGGCTACGACATGATGTGGTATCGCCAAGCTCCGGGGAAGGAGCGCGAGTTCGTCGCCCTCATCACCAGTGATTATTCTATCCGCTACGAAGACTCTGTGGAAGGTAGGTTCTCCATTAGCAGAGACAACGCAAAGAACACTGGATACCTGCTTATGAGCAACCTCACACCCGCCGACACTGCCATCTACTATTGTAAGACCTCTACCGCCGCTCGCGAAAGCTCCTGGTGCAGGTCCCGCTATCGCGTGGCCAGTTGGGGTCAGGGAACCCAGGTGACGGTATCTAGC | 214 |

TABLE 5-continued

Nucleic Acid sequences Encoding VHHs of Table 3

| Name | DNA Sequence | SEQ ID NO |
|---|---|---|
| mIL12Rb1_VHH12 | CAGGTTCAGTTGCAGGAGTCTGGAGGTGGCAGTGTGCAAGCT GGAGGCTCCCTCCGCCTGAGTTGCGCTGCCAGCAGATATACCT ATACGAATAACTTTATGGCTTGGTTTAGACAGGCCCCCGGTAA AGAGCGGGAAGGTGTGGCCGCGATTTACACCGGCGATGGCTA CGCCTATTACTTTTACAGCGTGAAGGGACGTTTCACCATTTCT CAGGATAACGATGAAAACATGCTGTATCTCCAAATGAACTCT CTGAAGCCTGAAGACACCGCTATGTATTACTGCGCGGCTATG GAGCGCAGGATCGGAACAAGACGCATGACTGAGAACGCTGA GTATAAATATTGGGGACAAGGCACACAGGTGACAGTTAGCTC C | 215 |
| mIL12Rb1_VHH13 | CAGGTCCAACTCCAGGAGTCCGGGGGAGGGTCTGTGCAGGCG GGTGGCTCCCTGCGCCTGAGCTGTGTCGCGTCTGGTTACTCCT ACTGTGGATATGATATGATGTGGTATAGACAGGCCCCAGGTA AGGAGCGCGAGTTTGTGGCCCTGATTACCAGCGACTACAGTA TCCGCTATGAGGATTCCGTGGAGGGCCGCTTCTCTATCTCACG CGACAACGCCAAGAATACAGGCTACCTCCTGATGAGCAACCT GACCCCTGCCGACACAGCCATTTATTACTGCAAGACCTCCACC GCCGCGCGTGAATCCGCTGGTGCAGGTCACGCTATCGTGTC GCCAGCTGGGTCAGGGGACACAGGTGACGGTGTCATCT | 216 |
| mIL12Rb1_VHH14 | CAAGTGCAGTTGCAAGAATCAGGAGGCGGGTCCGTGCAGGCG GGCGGATCTCTGCGTCTGTCTTGTGCTGTCTCCGGTTATGACT ACTGTGGTTACGACGTGCGCTGGTATCGCCAGGCCCCTGGTAA GGAACGTGAGTTCGTGAGCGGGATCAATAGCGACGGCTCCAC CTCTTATGCCGACAGTGTGAAGGGTAGGTTTACCATCAGTCAA GACAACGCCGAGAACACATCCTACCTTCATATGTTCTCTCTCA AGCCTGAGGATACCGCAATGTACTATTGCAAGACGGAGTCCC CAGCAGGTGAGTCCGCTTGGTGCAGAAACTTTCGCGGCATGG ATTATTGGGGAAGGGAACCCAGGTCACCGTGTCTTCC | 217 |
| mIL12Rb1_VHH15 | CAGGTGCAACTTCAGGAATCCGGTGGCGGATCTGTTCAGGCT GGCGGATTCCTGCGCCTGTCTTGCGTGGCCAGTGGCTACGGCT ACTGCGGCTATGATATGTCATGGTATCGCCAAGTGCCCGGCA AGGAGCGCGAGTTTGTAGCCCTCATCACATCTGATCGTTCTGT CAGCTACGAAGACAGTGTCAAGGGCCGCTTTTCCATCAGCCG CGATAATGCGAAGAACACGGCCTACTTGGAGATGAACAGACT GACACCGGATGACACCGCTGTATATTACTGTAAGACCTCAAC GGCTGCCAGAGAGAATAATTGGTGCCGTTCTCGCTACCGCATC GCTTATTGGGGCCAGGGAACACAGGTCACAGTCTCCTCC | 218 |
| mIL12Rb1_VHH16 | CAGGTGCAACTCCAGGAGAGCGGGGGAGGTTCCGTTCAGGCC GGGGGTTCCCTCAGATTGTCTTGTGCCGTCTCCGGGTACGATT ACTGTGGCTATGACGTGCGCTGGTATCGGCAGGCTCCTGGGA AGGAGCGGGAGTTCGTGAGTGGCATTAACTCAGACGGGTCTA CCTCCTATGCCGACAGCGTTAAGGGCAGGTTTACTATCAGTCA GGACAATGCGGAGAATACCAGTTACCTGCACATGTTCAGCCT CAAGCCCGAGGATACCGCCATGTATTACTGCAAGACAGAGGG TCCAGCTGGCGAGTCCGCATGGTGCCGCAACTTCAGGGGTAT GGACTACTGGGGCAAGGGTACTCAGGTGACTGTGTCCTCT | 219 |
| mIL12Rb1_VHH17 | CAGGTGCAGTTGCAGGAGTCAGGCGGGGGCTCTGTCCAGGCT GGGGGCTCTCTGAGACTGTCTTGTACTGCGTCTGGTTACACGT ACAGTTCTGCCTTTATGGCCTGGTTTCGGCAAGCGCCCGGAAA GGAGCGCGAGGGTGTTGCTGCCATGTATACCCGTGATGGCGG AACCGTCTACGCAGATTCTGTTAAGGGTCGTTTCACAATCTCC CAGGACAATGCGAAAAATACCCTCTATCTCCAGATCCACACC TTGAAGGCTGAGGACACCGCGATGTATTACTGTGCTGCCAAG ATCCCGCAGCCTGGCCGCGCTTCCCTGCTCGACAGCCAGACAT ACGACTACTGGGGTCAGGGCACACAGGTTACCGTGAGTAGT | 220 |
| mIL12Rb1_VHH18 | CAAGTCCAACTCCAGGAAAGCGGAGGTGGCAGCGTCCAGGCC GGGGGCTCTCTGAGACTGTCTTGTACCGCTTCCGGCTATACAT ATTCCTCTGCCTTTATGGCATGGTTCCGCCAAGCGCCAGGCAA GGAGCGCGAGGGCGTCGCCGCTATGTATACCAGAGACGGAGG CACCGTCTACGCTGACAGCGTCAAGGGACGCTTCACAATCTCC CAGGACAACGCCAAGAATACTTTGTATCTCCAGATGAATAGC CTCAAGCGGAGGACACCGCAATGTATTACTGCGCTGCAAAA ATCCCTCAGCCAGGTCGCGCCTCCCTCCTGGACAGTCAGACCT ATGATTATTGGGGCCAGGGGACCCAGGTGACTGTCTCCTCC | 221 |

TABLE 5-continued

Nucleic Acid sequences Encoding VHHs of Table 3

| Name | DNA Sequence | SEQ ID NO |
|---|---|---|
| mIL12Rb1_VHH19 | CAGGTACAGTTGCAGGAGTCCGGCGGAGGCAGCGTTCAGGCC GGTGGCTTCCTGAGGCTGTCCTGCGTCGCCAGCGGCTATGGAT ATTGCGGCTACGATATGTCCTGGTACAGACAGGTCCCTGGGA AAGAACGCGAGTTCGTGGCTCTTATCACATCCGACAGGTCCGT GTCCTATGAGGACTCTGTCAAGGGCCGTTTCAGCATCAGCCGT GACAACGCAAAAAACACGGCTTACTTGGAGATGAACCGGCTT ACCCCCGACGATACCGCGATTTATTACTGCAAGACCAGCACA GCAGCCAGGGAAATAATTGGTGTCGGAGCCGTTATCGTATC GCCTCTTGGGGACAGGGAACCCAGGTGACTGTCTCCTCA | 222 |
| mIL12Rb1_VHH20 | CAGGTGCAGCTCCAGGAGTCCGGCGGAGGCTCAGTACAAGCT GGCGGTTCACTCAGGTTGAGTTGTGTCGCCAGTGGCTACGGCT ATTGTGGCTATGATATGTCTTGGTATCGCCAGACCCCCGGCAA GGAGCGTGAGTTCGTGGCACTCATCACGTCCGACCGGATCGC CTCTTACGAAGACTCTGTCAAGGGCCGTTTTATTATCAGCCGC GACAACGCAAAAAACACTGGTTATCTCGACATGACTCGGGTG ACCCCCGATGACACTGCCATCTACTATTGCAAAACCTCTGCTG CGGCCCGCGAGAACTCCTGGTGCCGTAGTCGCTACCGCGTCG CCTCCTGGGGACAGGGTACACAGGTGACCGTTAGCTCC | 223 |
| mIL12Rb1_VHH21 | CAGGTCCAACTGCAAGAGTCTGGCGGTGGCTCCGTGCAGGCT GGCGGTAGTCTGCGCCTGTCTTGTGCAGTCAGCGGGTACGACT ACTGCGGTTATGATGTCAGATGGTATCGCCGTGCTCCCGGCAA GGAACGCGAGTTCGTCTCTGGCATTGACTCCGACGGCTCTACC TCCTATGCCGATAGCGTAAAGGGAAGGTTCACCATCAGCCAG GACAACGCTGAGAACACCAGCTACTTGCACATGTTCTCCCTTA AACCTGAGGACACAGCTATGTATTACTGTAAAACTGAGAGCC CGGCTGGCGAGAGCGCCTGGTGTCGCAACTTTCGTGGCATGG ACTACTGGGGTAAGGGCACCCAGGTTACTGTCTCTAGT | 224 |
| mIL12Rb1_VHH22 | CAGGTGCAACTTCAGGAGAGCGGTGGCGGTTCAGTGCAGGCT GGGGGAAGCCTGCGCCTGTCTTGCACCGCTTCCGGCTACACCT ATTCCAGTGCCTTCATGGCCTGGTTCCGCCAGGCCCCTGGAAA GGAACGCGAAGGCGTGGCTGCCATTTATACACGGGATGGGGG AACCGTCTACGCGGACTCCGTCAAGGGAAGATTCACCATTAG CCAGGATAATGCTAAGAACATCCTGTACCTCCAGATGAACTC CCTCAAAGCCGAGGATACTGCTATGTACTATTGTGCCGCTAAG ATTCCGCAGCCAGGCCGGGCATCCCTCCTGGACAGCCAGACC TATGACTACTGGGGACAGGGGACCCAGGTGACCGTGTCTTCC | 225 |
| mIL12Rb1_VHH23 | CAGGTGCAGCTCCAGGAGTCCGGCGGTGGCAGTGTCCAGGCA GGAGGCAGTCTGCGTCTGTCTTGCACTGCCTCAGGCTACACAT ACTCAAGCGCATTCATGGCCTGGTTCAGGCAGGCCCCTGGGA AGGAGCGCGAGGGTGTGGCAGCTATCTACACCCGCGATGGCG GTACTGTGTACGCCGATAGTGTCAAGGGGCGCTTTACCATTTC TCAGGACAACGCGAAGAACACCCTGTACTTGCAGATGAACAG CCTGAAGCCGGAGGATACTGCTATGTATTACTGCGCCGCAAA AATGCCCCAGCCGGGCCGCGCGTCTTTGCTGGATTCCCAGACA TACGACTACTGGGGGCAGGGCACCCAGGTTACGGTTAGCTCC | 226 |

The disclosure further provides recombinant viral and non-viral vectors comprising a nucleic acid encoding the IL12Rb1 binding molecules of the present disclosure or the CDRs of the IL12Rb1 binding molecules of the present disclosure.

The disclosure further provides host cells comprising recombinant viral and non-viral vectors comprising a nucleic acid the IL12Rb1 binding molecules of the present disclosure or the CDRs of the IL12Rb1 binding molecules of the present disclosure.

The disclosure further provides host cells comprising recombinant viral and non-viral vectors comprising a nucleic acid the IL12Rb1 binding molecules of the present disclosure or the CDRs of the IL12Rb1 binding molecules of the present disclosure.

The disclosure further kits comprising the IL12Rb1 binding molecules of the present disclosure.

In another aspect, the present disclosure provides constructs for the targeted delivery of therapeutic agents to a cell expressing the IL receptor, wherein the IL12Rb1 binding molecule is conjugated to one or more therapeutic agents, optionally through a chemical or polypeptide linker.

In another aspect, the present disclosure provides constructs for the identification of cells expressing the IL12RB1 receptor wherein the IL12RB1 binding molecule is conjugated to one or more imaging agents, optionally through a chemical or polypeptide linker. The disclosure further provides methods of use of the foregoing in the identification of cells expressing the IL12RB1 receptor in a subject, the method comprising the administration of a effective amount of the IL binding molecule conjugated to the imaging agent to a subject in need to treatment and evaluating the subject for the presence of the imaging agent that is conjugated to the IL12RB1 binding molecule.

In another aspect, the present disclosure provides IL binding molecules which have been modified for extended duration of action in vivo wherein the IL binding molecule is conjugated to one or more carrier molecules.

The present disclosure provides IL12RB1 binding molecules comprising a polypeptide sequence that specifically binds to the extracellular domain of the IL12RB1 and methods of use thereof in the isolation, depletion or enrichment of cells expressing the IL12RB1 cells a biological sample.

DETAILED DESCRIPTION OF THE INVENTION

Introduction

In order for the present disclosure to be more readily understood, certain terms and phrases are defined below as well as throughout the specification. The definitions provided herein are non-limiting and should be read in view of the knowledge of one of skill in the art would know.

Before the present methods and compositions are described, it is to be understood that this disclosure is not limited to particular method or composition described, as such may, of course, vary.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, some potential and preferred methods and materials are now described. All publications mentioned herein are incorporated herein by reference to disclose and describe the methods and/or materials in connection with which the publications are cited.

It should be noted that as used herein and in the appended claims, the singular forms "a", "an", and "the" include plural referents unless the context clearly dictates otherwise. Thus, for example, reference to "a cell" includes a plurality of such cells and reference to "the peptide" includes reference to one or more peptides and equivalents thereof, e.g., polypeptides, known to those skilled in the art, and so forth.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

It will be appreciated that throughout this disclosure reference is made to amino acids according to the single letter or three letter codes. For the reader's convenience, the single and three letter amino acid codes are provided in Table 6 below:

TABLE 6

| Amino Acid Abbreviations | | |
|---|---|---|
| Single Letter Abbreviation | Name | 3-letter abbreviation |
| G | Glycine | Gly |
| P | Proline | Pro |
| A | Alanine | Ala |
| V | Valine | Val |
| L | Leucine | Leu |
| I | Isoleucine | Ile |
| M | Methionine | Met |
| C | Cysteine | Cys |
| F | Phenylalanine | Phe |
| Y | Tyrosine | Tyr |
| W | Tryptophan | Trp |
| H | Histidine | His |
| K | Lysine | Lys |
| R | Arginine | Arg |
| Q | Glutamine | Gln |
| N | Asparagine | Asn |
| E | Glutamic Acid | Glu |
| D | Aspartic Acid | Asp |
| S | Serine | Ser |
| T | Threonine | Thr |

Standard methods in molecular biology are described in the scientific literature (see, e.g., Sambrook and Russell (2001) Molecular Cloning, 3rd ed., Cold Spring Harbor Laboratory Press, Cold Spring Harbor, N.Y.; and Ausubel, et al. (2001) Current Protocols in Molecular Biology, Vols. 1-4, John Wiley and Sons, Inc. New York, N.Y., which describes cloning in bacterial cells and DNA mutagenesis (Vol. 1), cloning in mammalian cells and yeast (Vol. 2), glycoconjugates and protein expression (Vol. 3), and bioinformatics (Vol. 4)). The scientific literature describes methods for protein purification, including immunoprecipitation, chromatography, electrophoresis, centrifugation, and crystallization, as well as chemical analysis, chemical modification, post-translational modification, production of fusion proteins, and glycosylation of proteins (see, e.g., Coligan, et al. (2000) Current Protocols in Protein Science, Vols. 1-2, John Wiley and Sons, Inc., NY).

Definitions

Unless otherwise indicated, the following terms are intended to have the meaning set forth below. Other terms are defined elsewhere throughout the specification.

Activate: As used herein the term "activate" is used in reference to a receptor or receptor complex to reflect a biological effect, directly and/or by participation in a multicomponent signaling cascade, arising from the binding of an agonist ligand to a receptor responsive to the binding of the ligand.

Activity: As used herein, the term "activity" is used with respect to a molecule to describe a property of the molecule with respect to a test system (e.g., an assay) or biological or chemical property (e.g., the degree of binding of the molecule to another molecule) or of a physical property of a material or cell (e.g., modification of cell membrane potential). Examples of such biological functions include but are not limited to catalytic activity of a biological agent, the ability to stimulate intracellular signaling, gene expression, cell proliferation, the ability to modulate immunological activity such as inflammatory response. "Activity" is typically expressed as a level of a biological activity per unit of agent tested such as [catalytic activity]/[mg protein], [immunological activity]/[mg protein], international units (IU) of activity, [STAT5 phosphorylation]/[mg protein], [proliferation]/[mg protein], plaque forming units (pfu), etc. As used herein, the term proliferative activity refers to an activity that promotes cell proliferation and replication, including dysregulated cell division such as that observed in neoplastic diseases, inflammatory diseases, fibrosis, dysplasia, cell transformation, metastasis, and angiogenesis.

Affinity: As used herein the term "affinity" refers to the degree of specific binding of a first molecule (e.g., a ligand) to a second molecule (e.g., a receptor) and is measured by the equilibrium dissociation constant ($K_D$), a ratio of the dissociation rate constant between the molecule and its target ($K_{off}$) and the association rate constant between the molecule and its target ($K_{on}$).

Agonist: As used herein, the term "agonist" refers a first agent that specifically binds a second agent ("target") and interacts with the target to cause or promote an increase in the activation of the target. In some instances, agonists are activators of receptor proteins that modulate cell activation, enhance activation, sensitize cells to activation by a second agent, or up-regulate the expression of one or more genes, proteins, ligands, receptors, biological pathways, that may result in cell proliferation or pathways that result in cell cycle arrest or cell death such as by apoptosis. In some embodiments, an agonist is an agent that binds to a receptor and alters the receptor state resulting in a biological response that mimics the effect of the endogenous ligand of the receptor. The term "agonist" includes partial agonists, full agonists and superagonists. An agonist may be described as a "full agonist" when such agonist which leads to a substantially full biological response (i.e. the response associated with the naturally occurring ligand/receptor binding interaction) induced by receptor under study, or a partial agonist. A "superagonist" is a type of agonist that can produce a maximal response greater than the endogenous agonist for the target receptor, and thus has an activity of more than 100% of the native ligand. A super agonist is typically a synthetic molecule that exhibits greater than 110%, alternatively greater than 120%, alternatively greater than 130%, alternatively greater than 140%, alternatively greater than 150%, alternatively greater than 160%, or alternatively greater than 170% of the response in an evaluable quantitative or qualitative parameter of the naturally occurring form of the molecule when evaluated at similar concentrations in a comparable assay. It should be noted that the biological effects associated with the full agonist may differ in degree and/or in kind from those biological effects of partial or superagonists. In contrast to agonists, antagonists may specifically bind to a receptor but do not result the signal cascade typically initiated by the receptor and may to modify the actions of an agonist at that receptor. Inverse agonists are agents that produce a pharmacological response that is opposite in direction to that of an agonist.

Antagonist: As used herein, the term "antagonist" or "inhibitor" refers a molecule that opposes the action(s) of an agonist. An antagonist prevents, reduces, inhibits, or neutralizes the activity of an agonist, and an antagonist can also prevent, inhibit, or reduce constitutive activity of a target, e.g., a target receptor, even where there is no identified agonist. Inhibitors are molecules that decrease, block, prevent, delay activation, inactivate, desensitize, or down-regulate, e.g., a gene, protein, ligand, receptor, biological pathway including an immune checkpoint pathway, or cell.

Antibody: As used herein, the term "antibody" refers collectively to: (a) a glycosylated or non-glycosylated immunoglobulin that specifically binds to target molecule, and (b) immunoglobulin derivatives thereof, including but not limited to antibody fragments such as single domain antibodies. In some embodiments the immunoglobulin derivative competes with the immunoglobulin from which it was derived for binding to the target molecule. The term antibody is not restricted to immunoglobulins derived from any particular species and includes murine, human, equine, camelids, antibodies of cartilaginous fishes including, but not limited to, sharks. The term "antibody" encompasses antibodies isolatable from natural sources or from animals following immunization with an antigen and as well as engineered antibodies including monoclonal antibodies, bispecific antibodies, tri-specific, chimeric antibodies, humanized antibodies, human antibodies, CDR-grafted, veneered, or deimmunized (e.g., to remove T-cell epitopes) antibodies, camelized (in the case of VHHs), or molecules comprising binding domains of antibodies (e.g., CDRs) in non-immunoglobulin scaffolds. The term "antibody" should not be construed as limited to any particular means of synthesis and includes naturally occurring antibodies isolatable from natural sources and as well as engineered antibodies molecules that are prepared by "recombinant" means including antibodies isolated from transgenic animals that are transgenic for human immunoglobulin genes or a hybridoma prepared therefrom, antibodies isolated from a host cell transformed with a nucleic acid construct that results in expression of an antibody, antibodies isolated from a combinatorial antibody library including phage display libraries. In one embodiment, an "antibody" is a mammalian immunoglobulin of the IgG1, IgG2, IgG3 or IgG4 class. In some embodiments, the antibody is a "full length antibody" comprising variable and constant domains providing binding and effector functions. The term "single domain antibody" (sdAb) as used herein refers an antibody fragment consisting of a monomeric variable antibody domain that is able to bind specifically to an antigen and compete for binding with the parent antibody from which it is derived. The term "single domain antibody" includes scFv and VHH molecules. As used herein, the term "VHH" refers to a single domain antibody derived from camelid antibody typically obtained from immunization of camelids (including camels, llamas and alpacas (see, e.g., Hamers-Casterman, et al. (1993) Nature 363:446-448). VHHs are also referred to as heavy chain antibodies or Nanobodies® as Single domain antibodies may also be derived from non-mammalian sources such as VHHs obtained from IgNAR antibodies immunization of cartilaginous fishes including, but not limited to, sharks.

Biological Sample: As used herein, the term "biological sample" or "sample" refers to a sample obtained (or derived) from a subject. By way of example, a biological sample comprises a material selected from the group consisting of body fluids, blood, whole blood, plasma, serum, mucus secretions, saliva, cerebrospinal fluid (CSF), bronchoalveolar lavage fluid (BALF), fluids of the eye (e.g., vitreous fluid, aqueous humor), lymph fluid, lymph node tissue, spleen tissue, bone marrow, tumor tissue, including immunoglobulin enriched or cell-type specific enriched fractions derived from one or more of such tissues.

IL cell: The terms "IL12RB1 cell", "IL12RB1-expressing cell", "IL12RB1-positive cell" and "IL12RB1+" cell are used interchangeably herein to refer to a cell which expresses and displays the IL12RB1 antigen on the extracellular surface of the cell membrane. Similarly, the terms "IL12RB1-negative cell", "IL12RB1– cells" as are used interchangeably herein to describe cells which do not express or display IL12RB1 antigen on the cell surface.

CDR: As used herein, the term "CDR" or "complementarity determining region" is intended to mean the noncontiguous antigen combining sites found within the variable region of both heavy and light chain immunoglobulin polypeptides. CDRs have been described by Kabat et al., J. Biol. Chem. 252:6609-6616 (1977); Kabat, et al., U.S. Dept. of Health and Human Services publication entitled "Sequences of proteins of immunological interest" (1991) (also referred to herein as "Kabat 1991" or "Kabat"); by Chothia, et al. (1987) J. Mol. Biol. 196:901-917 (also referred to herein as "Chothia"); and MacCallum, et al. (1996) J. Mol. Biol. 262:732-745, where the definitions include overlapping or subsets of amino acid residues when compared against each other. Nevertheless, application of either definition to refer to a CDR of an antibody or grafted antibodies or variants thereof is intended to be within the scope of the term as defined and used herein. The term "Chothia Numbering" as used herein is recognized in the arts and refers to a system of numbering amino acid residues based on the location of the structural loop regions (Chothia et al. 1986, Science 233:755-758; Chothia & Lesk 1987, JMB 196:901-917; Chothia et al. 1992, JMB 227:799-817). For purposes of the present disclosure, unless otherwise specifically identified, the positioning of CDRs2 and 3 in the variable region of an antibody follows Kabat numbering or simply, "Kabat." The positioning of CDR1 in the variable region of an antibody follows a hybrid of Kabat and Chothia numbering schemes.

Comparable: As used herein, the term "comparable" is used to describe the degree of difference in two measurements of an evaluable quantitative or qualitative parameter. For example, where a first measurement of an evaluable quantitative parameter and a second measurement of the evaluable parameter do not deviate beyond a range that the skilled artisan would recognize as not producing a statistically significant difference in effect between the two results in the circumstances, the two measurements would be considered "comparable." In some instances, measurements may be considered "comparable" if one measurement deviates from another by less than 35%, alternatively by less than 30%, alternatively by less than 25%, alternatively by less than 20%, alternatively by less than 15%, alternatively by less than 10%, alternatively by less than 7%, alternatively by less than 5%, alternatively by less than 4%, alternatively by less than 3%, alternatively by less than 2%, or by less than 1%. In particular embodiments, one measurement is comparable to a reference standard if it deviates by less than 15%, alternatively by less than 10%, or alternatively by less than 5% from the reference standard.

Clonotype: As used herein, a clonotype refers to a collection of binding molecules that originate from the same B-cell progenitor cell. The term "clonotype" is used to refer to a collection of antigen binding molecules that belong to the same germline family, have the same CDR3 lengths, and have 70% or greater homology in CDR3 sequence.

Conservative Amino Acid Substitution: As used herein, the term "conservative amino acid substitution" refers to an amino acid replacement that changes a given amino acid to a different amino acid with similar biochemical properties (e.g., charge, hydrophobicity, and size). For example, the amino acids in each of the following groups can be considered as conservative amino acids of each other: (1) hydrophobic amino acids: alanine, isoleucine, leucine, tryptophan, phenylalanine, valine, proline, and glycine; (2) polar amino acids: glutamine, asparagine, histidine, serine, threonine, tyrosine, methionine, and cysteine; (3) basic amino acids: lysine and arginine; and (4) acidic amino acids: aspartic acid and glutamic acid.

Derived From: As used herein in the term "derived from", in the context of an amino acid sequence is meant to indicate that the polypeptide or nucleic acid has a sequence that is based on that of a reference polypeptide or nucleic acid and is not meant to be limiting as to the source or method in which the protein or nucleic acid is made. By way of example, the term "derived from" includes homologs or variants of reference amino acid or DNA sequences.

Effective Concentration (EC): As used herein, the terms "effective concentration" or its abbreviation "EC" are used interchangeably to refer to the concentration of an agent in an amount sufficient to effect a change in a given parameter in a test system. The abbreviation "E" refers to the magnitude of a given biological effect observed in a test system when that test system is exposed to a test agent. When the magnitude of the response is expressed as a factor of the concentration ("C") of the test agent, the abbreviation "EC" is used. In the context of biological systems, the term Emax refers to the maximal magnitude of a given biological effect observed in response to a saturating concentration of an activating test agent. When the abbreviation EC is provided with a subscript (e.g., $EC_{40}$, $EC_{50}$, etc.) the subscript refers to the percentage of the Emax of the biological response observed at that concentration. For example, the concentration of a test agent sufficient to result in the induction of a measurable biological parameter in a test system that is 30% of the maximal level of such measurable biological parameter in response to such test agent, this is referred to as the "$EC_{30}$" of the test agent with respect to such biological parameter. Similarly, the term "$EC_{100}$" is used to denote the effective concentration of an agent that results the maximal (100%) response of a measurable parameter in response to such agent. Similarly, the term $EC_{50}$ (which is commonly used in the field of pharmacodynamics) refers to the concentration of an agent sufficient to results in the half-maximal (about 50%) change in the measurable parameter. The term "saturating concentration" refers to the maximum possible quantity of a test agent that can dissolve in a standard volume of a specific solvent (e.g., water) under standard conditions of temperature and pressure. In pharmacodynamics, a saturating concentration of a drug is typically used to denote the concentration sufficient of the drug such that all available receptors are occupied by the drug, and $EC_{50}$ is the drug concentration to give the half-maximal effect.

Enriched: As used herein in the term "enriched" refers to a sample that is non-naturally manipulated so that a species (e.g., a molecule or cell) of interest is present in: (a) a greater concentration (e.g., at least 3-fold greater, alternatively at least 5-fold greater, alternatively at least 10-fold greater, alternatively at least 50-fold greater, alternatively at least 100-fold greater, or alternatively at least 1000-fold greater) than the concentration of the species in the starting sample, such as a biological sample (e.g., a sample in which the molecule naturally occurs or in which it is present after administration); or (b) a concentration greater than the environment in which the molecule was made (e.g., a recombinantly modified bacterial or mammalian cell).

Extracellular Domain: As used herein the term "extracellular domain" or its abbreviation "ECD" refers to the portion of a cell surface protein (e.g., a cell surface receptor) which is external to of the plasma membrane of a cell. The cell surface protein may be transmembrane protein, a cell surface or membrane associated protein.

Identity: The term "identity," as used herein in reference to polypeptide or DNA sequences, refers to the subunit sequence identity between two molecules. When a subunit position in both of the molecules is occupied by the same monomeric subunit (i.e., the same amino acid residue or nucleotide), then the molecules are identical at that position. The similarity between two amino acid or two nucleotide sequences is a direct function of the number of identical positions. In general, the sequences are aligned so that the highest order match is obtained. If necessary, identity can be calculated using published techniques and widely available computer programs, such as BLAST 2.0 algorithms, which are described in Altschul et al. (1990) J Mol. Biol. 215: 403-410 and Altschul, et al. (1977) Nucleic Acids Res. 25: 3389-3402. Software for performing BLAST analyses is publicly available through the National Center for Biotechnology Information (NCBI) web site. The algorithm involves first identifying high scoring sequence pairs (HSPs) by identifying short words of length W of the query sequence, which either match or satisfy some positive-valued threshold score "T" when aligned with a word of the same length in a database sequence. T is referred to as the neighborhood word score threshold (Altschul, et al., supra). These initial neighborhood word hits act as seeds for initiating searches to find longer HSPs containing them. The word hits are then extended in both directions along each sequence for as far as the cumulative alignment score can be increased. Cumulative scores are calculated using, for nucleotide sequences, the parameters "M" (the reward score for a pair of matching residues; always >0) and "N" (the penalty score for mismatching residues; always <0). For amino acid sequences, a scoring matrix is used to calculate the cumulative score. Extension of the word hits in each direction are halted when: (a) the cumulative alignment score falls off by the quantity X from its maximum achieved value; the cumulative score goes to zero or below, due to the accumulation of one or more negative-scoring residue alignments; or (b) the end of either sequence is reached. The BLAST algorithm parameters "W", "T", and "X" determine the sensitivity and speed of the alignment. The BLASTN program (for nucleotide sequences) functions similarly but uses as defaults a word size ("W") of 28, an expectation ("E") of 10, M=1, N=−2, and a comparison of both strands. For amino acid sequences, the BLASTP program uses as defaults a word size (W) of 3, an expectation (E) of 10, and the BLOSUM62 scoring matrix (see Henikoff & Henikoff, (1989) PNAS (USA) 89:10915-10919).

In An Amount Sufficient Amount to Cause a Response: As used herein the phrase "in an amount sufficient to cause a response" is used in reference to the amount of a test agent sufficient to provide a detectable change in the level of an indicator measured before (e.g., a baseline level) and after the application of a test agent to a test system. In some embodiments, the test system is a cell, tissue or organism. In some embodiments, the test system is an in vitro test system such as a fluorescent assay. In some embodiments, the test system is an in vivo system which involves the measurement of a change in the level a parameter of a cell, tissue, or organism reflective of a biological function before and after the application of the test agent to the cell, tissue, or organism. In some embodiments, the indicator is reflective of biological function or state of development of a cell evaluated in an assay in response to the administration of a quantity of the test agent. In some embodiments, the test system involves the measurement of a change in the level an indicator of a cell, tissue, or organism reflective of a biological condition before and after the application of one or more test agents to the cell, tissue, or organism. The term "in an amount sufficient to effect a response" may be sufficient to be a therapeutically effective amount but may also be more or less than a therapeutically effective amount.

Inhibitor: As used herein the term "inhibitor" refers to a molecule that decreases, blocks, prevents, delays activation of, inactivates, desensitizes, or down-regulates, e.g., a gene, protein, ligand, receptor, or cell. An inhibitor can also be defined as a molecule that reduces, blocks, or inactivates a constitutive activity of a cell or organism.

Intracellular Domain: As used herein the term "intracellular domain" or its abbreviation "ICD" refers to the portion of a cell surface protein (e.g., a cell surface receptor) which is inside of the plasma membrane of a cell. The ICD may include the entire cytoplasmic portion of a transmembrane protein or membrane associated protein, or intracellular protein.

Isolated: As used herein the term "isolated" is used in reference to a polypeptide of interest that, if naturally occurring, is in an environment different from that in which it can naturally occur. "Isolated" is meant to include polypeptides that are within samples that are substantially enriched for the polypeptide of interest and/or in which the polypeptide of interest is partially or substantially purified. Where the polypeptide is not naturally occurring, "isolated" indicates that the polypeptide has been separated from an environment in which it was synthesized, for example isolated from a recombinant cell culture comprising cells engineered to express the polypeptide or by a solution resulting from solid phase synthetic means.

Kabat Numbering: The term "Kabat numbering" as used herein is recognized in the art and refers to a system of numbering amino acid residues which are more variable than other amino acid residues (e.g., hypervariable) in the heavy and light chain regions of immunoglobulins (Kabat, et al., (1971) *Ann. NY Acad. Sci.* 190:382-93; Kabat, et al., (1991) *Sequences of Proteins of Immunological Interest*, Fifth Edition, U.S. Department of Health and Human Services, NIH Publication No. 91-3242). The term "Chothia Numbering" as used herein is recognized in the arts and refers to a system of numbering amino acid residues based on the location of the structural loop regions (Chothia et al. 1986, Science 233:755-758; Chothia & Lesk 1987, JMB 196:901-917; Chothia et al. 1992, JMB 227:799-817). For purposes of the present disclosure, unless otherwise specifically identified, the positioning of CDRs 2 and 3 in the variable region of an antibody follows Kabat numbering or simply, "Kabat." The positioning of CDR1 in the variable region of an antibody follows a hybrid of Kabat and Chothia numbering schemes.

Ligand: As used herein, the term "ligand" refers to a molecule that specifically binds a receptor and causes a change in the receptor so as to effect a change in the activity of the receptor or a response in cell that expresses that receptor. In one embodiment, the term "ligand" refers to a molecule or complex thereof that can act as an agonist or antagonist of a receptor. As used herein, the term "ligand" encompasses natural and synthetic ligands. "Ligand" also encompasses small molecules, peptide mimetics of cytokines and antibodies. The complex of a ligand and receptor is termed a "ligand-receptor complex." A ligand may comprise one domain of a polyprotein or fusion protein (e.g., either domain of an antibody/ligand fusion protein).

Modulate: As used herein, the terms "modulate", "modulation" and the like refer to the ability of a test agent to cause a response, either positive or negative or directly or indirectly, in a system, including a biological system, or biochemical pathway. The term modulator includes both agonists (including partial agonists, full agonists and superagonists) and antagonists.

Nucleic Acid: The terms "nucleic acid", "nucleic acid molecule", "polynucleotide" and the like are used interchangeably herein to refer to a polymeric form of nucleotides of any length, either deoxyribonucleotides or ribonucleotides, or analogs thereof. Non-limiting examples of polynucleotides include linear and circular nucleic acids, messenger RNA (mRNA), complementary DNA (cDNA), recombinant polynucleotides, vectors, probes, primers and the like.

Operably Linked: The term "operably linked" is used herein to refer to the relationship between molecules, typically polypeptides or nucleic acids, which are arranged in a construct such that each of the functions of the component molecules is retained although the operable linkage may result in the modulation of the activity, either positively or negatively, of the individual components of the construct. For example, the operable linkage of a polyethylene glycol (PEG) molecule to a wild-type protein may result in a construct where the biological activity of the protein is diminished relative to the to the wild-type molecule, however the two are nevertheless considered operably linked. When the term "operably linked" is applied to the relationship of multiple nucleic acid sequences encoding differing functions, the multiple nucleic acid sequences when combined into a single nucleic acid molecule that, for example, when introduced into a cell using recombinant technology, provides a nucleic acid which is capable of effecting the transcription and/or translation of a particular nucleic acid sequence in a cell. For example, the nucleic acid sequence encoding a signal sequence may be considered operably linked to DNA encoding a polypeptide if it results in the expression of a preprotein whereby the signal sequence facilitates the secretion of the polypeptide; a promoter or enhancer is considered operably linked to a coding sequence if it affects the transcription of the sequence; or a ribosome binding site is considered operably linked to a coding sequence if it is positioned so as to facilitate translation. Generally, in the context of nucleic acid molecules, the term "operably linked" means that the nucleic acid sequences being linked are contiguous, and, in the case of a secretory leader or associated subdomains of a molecule, contiguous and in reading phase. However, certain genetic elements such as enhancers may function at a distance and need not be contiguous with respect to the sequence to which they provide their effect but nevertheless may be considered operably linked.

Parent Polypeptide: As used herein, the terms "parent polypeptide" or "parent protein" are used interchangeably to designate the source of a second polypeptide (e.g., a derivative, mutein or variant) which is modified with respect to a first "parent" polypeptide. In some instances, the parent polypeptide is a wild-type or naturally occurring form of a protein. In some instance, the parent polypeptide may be a modified form a naturally occurring protein that is further modified. The term "parent polypeptide" may refer to the polypeptide itself or compositions that comprise the parent polypeptide (e.g., glycosylated or PEGylated forms and/or fusion proteins comprising the parent polypeptide).

Partial Agonist: As used herein, the term "partial agonist" refers to a molecule that specifically binds that bind to and activate a given receptor but possess only partial activation the receptor relative to a full agonist. Partial agonists may display both agonistic and antagonistic effects. For example, when both a full agonist and partial agonist are present, the partial agonist acts as a competitive antagonist by competing with the full agonist for the receptor binding resulting in net decrease in receptor activation relative to the contact of the receptor with the full agonist in the absence of the partial agonist. Partial agonists can be used to activate receptors to give a desired submaximal response in a subject when inadequate amounts of the endogenous ligand are present, or they can reduce the overstimulation of receptors when excess amounts of the endogenous ligand are present. The maximum response ($E_{max}$) produced by a partial agonist is called its intrinsic activity and may be expressed on a percentage scale where a full agonist produced a 100% response. An partial agonist may have greater than 10% but less than 100%, alternatively greater than 20% but less than 100%, alternatively greater than 30% but less than 100%, alternatively greater than 40% but less than 100%, alternatively greater than 50% but less than 100%, alternatively greater than 60% but less than 100%, alternatively greater than 70% but less than 100%, alternatively greater than 80% but less than 100%, or alternatively greater than 90% but less than 100%, of the activity of the reference polypeptide when evaluated at similar concentrations in a given assay system.

Polypeptide: As used herein the terms "polypeptide," "peptide," and "protein", used interchangeably herein, refer to a polymeric form of amino acids of any length, which can include genetically coded and non-genetically coded amino acids, chemically or biochemically modified or derivatized amino acids, and polypeptides having modified polypeptide backbones. The term polypeptide include fusion proteins, including, but not limited to, fusion proteins with a heterologous amino acid sequence; fusion proteins with heterologous and homologous leader sequences; fusion proteins with or without N-terminal methionine residues; fusion proteins with amino acid sequences that facilitate purification such as chelating peptides; fusion proteins with immunologically tagged proteins; fusion proteins comprising a peptide with immunologically active polypeptide fragment (e.g., antigenic diphtheria or tetanus toxin or toxoid fragments) and the like.

Prevent: As used herein the terms "prevent", "preventing", "prevention" and the like refer to a course of action initiated with respect to a subject prior to the onset of a disease, disorder, condition or symptom thereof so as to prevent, suppress, inhibit or reduce, either temporarily or permanently, a subject's risk of developing a disease, disorder, condition or the like (as determined by, for example, the absence of clinical symptoms) or delaying the onset thereof. A course of action to prevent a disease, disorder or condition in a subject is typically applied in the context of a subject who is predisposed to developing a disease, disorder or condition due to genetic, experiential or environmental factors of developing a particular disease, disorder or condition. In certain instances, the terms "prevent", "preventing", "prevention" are also used to refer to the slowing of the progression of a disease, disorder or condition from an existing state to a more deleterious state.

Receptor: As used herein, the term "receptor" refers to a polypeptide having a domain that specifically binds a ligand that binding of the ligand results in a change to at least one biological property of the polypeptide. In some embodiments, the receptor is a cell membrane associated protein that comprises and extracellular domain (ECD) and a membrane associated domain which serves to anchor the ECD to the cell surface. In some embodiments of cell surface receptors, the receptor is a membrane spanning polypeptide comprising an intracellular domain (ICD) and extracellular domain (ECD) linked by a membrane spanning domain typically referred to as a transmembrane domain (TM). The binding of a cognate ligand to the receptor results in a conformational change in the receptor resulting in a measurable biological effect. In some instances, where the receptor is a membrane spanning polypeptide comprising an ECD, TM and ICD, the binding of the ligand to the ECD results in a measurable intracellular biological effect mediated by one or more domains of the ICD in response to the binding of the ligand to the ECD. In some embodiments, a receptor is a component of a multi-component complex to facilitate intracellular signaling. For example, the ligand may bind a cell surface receptor that is not associated with any intracellular signaling alone but upon ligand binding facilitates the formation of a heteromultimeric (including heterodimeric, heterotrimeric, etc.) or homomultimeric (including homodimeric, homotrimeric, homotetrameric, etc.) complex that results in a measurable biological effect in the cell such as activation of an intracellular signaling cascade (e.g., the Jak/STAT pathway). In some embodiments, a receptor is a membrane spanning single chain polypeptide comprising ECD, TM and ICD domains wherein the ECD, TM and ICD domains are derived from the same or differing naturally occurring receptor variants or synthetic functional equivalents thereof.

Recombinant: As used herein, the term "recombinant" is used as an adjective to refer to the method by which a polypeptide, nucleic acid, or cell was modified using recombinant DNA technology. A "recombinant protein" is a protein produced using recombinant DNA technology and is frequently abbreviated with a lower case "r" preceding the protein name to denote the method by which the protein was produced (e.g., recombinantly produced human growth hormone is commonly abbreviated "rhGH"). Similarly a cell is referred to as a "recombinant cell" if the cell has been modified by the incorporation (e.g., transfection, transduction, infection) of exogenous nucleic acids (e.g., ssDNA, dsDNA, ssRNA, dsRNA, mRNA, viral or non-viral vectors, plasmids, cosmids and the like) using recombinant DNA technology. The techniques and protocols for recombinant DNA technology are well known in the art such as those can be found in Sambrook, et al. (1989) Molecular Cloning: A Laboratory Manual (2d ed., Cold Spring Harbor Laboratory Press, Plainview, N.Y.) and other standard molecular biology laboratory manuals.

Response: The term "response," for example, of a cell, tissue, organ, or organism, encompasses a quantitative or qualitative change in a evaluable biochemical or physiological parameter, (e.g., concentration, density, adhesion, proliferation, activation, phosphorylation, migration, enzymatic activity, level of gene expression, rate of gene expression, rate of energy consumption, level of or state of differentiation) where the change is correlated with the activation, stimulation, or treatment, with or contact with exogenous agents or internal mechanisms such as genetic programming. In certain contexts, the terms "activation", "stimulation", and the like refer to cell activation as regulated by internal mechanisms, as well as by external or environmental factors; whereas the terms "inhibition", "down-regulation" and the like refer to the opposite effects. A "response" may be evaluated in vitro such as through the use of assay systems, surface plasmon resonance, enzymatic activity, mass spectroscopy, amino acid or protein sequencing technologies. A "response" may be evaluated in vivo quantitatively by evaluation of objective physiological parameters such as body temperature, bodyweight, tumor volume, blood pressure, results of X-ray or other imaging technology or qualitatively through changes in reported subjective feelings of well-being, depression, agitation, or pain. In some embodiments, the level of proliferation of CD3 activated primary human T-cells may be evaluated in a bioluminescent assay that generates a luminescent signal that is proportional to the amount of ATP present which is directly proportional to the number of viable cells present in culture as described in Crouch, et al. (1993) J. Immunol. Methods 160: 81-8 or using commercially available assays such as the CellTiter-Glo® 2.0 Cell Viability Assay or CellTiter-Glo® 3D Cell Viability kits commercially available from Promega Corporation, Madison WI 53711 as catalog numbers G9241 and G9681 in substantial accordance with the instructions provided by the manufacturer. In some embodiments, the level of activation of T cells in response to the administration of a test agent may be determined by flow cytometric methods as described as determined by the level of STAT (e.g., STAT1, STAT3, STAT5) phosphorylation in accordance with methods well known in the art.

Significantly Reduced Binding: As used herein, the term "exhibits significantly reduced binding" is used with respect a variant of a first molecule (e.g., a ligand or antibody) which exhibits a significant reduction in the affinity for a second molecule (e.g., receptor or antigen) relative the parent form of the first molecule. With respect to antibody variants, an antibody variant "exhibits significantly reduced binding" if the affinity of the variant antibody for an antigen if the variant binds to the native form of the receptor with and affinity of less than 20%, alternatively less than about 10%, alternatively less than about 8%, alternatively less than about 6%, alternatively less than about 4%, alternatively less than about 2%, alternatively less than about 1%, or alternatively less than about 0.5% of the parent antibody from which the variant was derived. Similarly, with respect to variant ligands, a variant ligand "exhibits significantly reduced binding" if the affinity of the variant ligand binds to a receptor with an affinity of less than 20%, alternatively less than about 10%, alternatively less than about 8%, alternatively less than about 6%, alternatively less than about 4%, alternatively less than about 2%, alternatively less than about 1%, or alternatively less than about 0.5% of the parent ligand from which the variant ligand was derived. Similarly, with respect to variant receptors, a variant ligand "exhibits significantly reduced binding" if the affinity of the variant receptors binds to a with an affinity of less than 20%, alternatively less than about 10%, alternatively less than about 8%, alternatively less than about 6%, alternatively less than about 4%, alternatively less than about 2%, alternatively less than about 1%, or alternatively less than about 0.5% of the parent receptor from which the variant receptor was derived.

Small Molecule(s): The term "small molecules" refers to chemical compounds (typically pharmaceutically active compounds) having a molecular weight that is less than about 10 kDa, less than about 2 kDa, or less than about lkDa. Small molecules include, but are not limited to, inorganic molecules, organic molecules, organic molecules containing an inorganic component, molecules comprising a radioactive atom, and synthetic molecules. The term "small molecule" is a term well understood to those of ordinary skill in the pharmaceutical arts and is typically used to distinguish organic chemical compounds from biologics.

Specifically Binds: As used herein the term "specifically binds" refers to the degree of affinity for which a first molecule exhibits with respect to a second molecule. In the context of binding pairs (e.g., ligand/receptor, antibody/antigen) a first molecule of a binding pair is said to specifically bind to a second molecule of a binding pair when the first molecule of the binding pair does not bind in a significant amount to other components present in the sample. A first molecule of a binding pair is said to specifically bind to a second molecule of a binding pair when the first molecule of the binding pair when the affinity of the first molecule for the second molecule is at least two-fold greater, alternatively at least five times greater, alternatively at least ten times greater, alternatively at least 20-times greater, or alternatively at least 100-times greater than the affinity of the first molecule for other components present in the sample. In a particular embodiment, where the first molecule of the binding pair is an antibody, the antibody specifically binds to the antigen (or antigenic determinant (epitope) of a protein, antigen, ligand, or receptor) if the equilibrium dissociation constant ($K_D$) between antibody and the antigen is lesser than about $10^{-6}$ M, alternatively lesser than about $10^{-8}$ M, alternatively lesser than about $10^{-10}$ M, alternatively lesser than about 1011M, lesser than about $10^{-12}$ M as determined by, e.g., Scatchard analysis (Munsen, et al. (1980) Analyt. Biochem. 107:220-239). In one embodiment where the ligand is an ILR binding sdAb and the receptor comprises an ILR, the ILR binding sdAb specifically binds if the equilibrium dissociation constant ($K_D$) of the ILR binding sdAb/ILR ECD is lesser than about $10^{-5}$M, alternatively lesser than about $10^{-6}$ M, alternatively lesser than about $10^{-7}$M, alternatively lesser than about $10^{-8}$M, alternatively lesser than about $10^{-9}$ M, alternatively lesser than about 1010 M, or alternatively lesser than about $10^{-11}$ M. Specific binding may be assessed using techniques known in the art including but not limited to competition ELISA assays, radioactive ligand binding assays (e.g., saturation binding, Scatchard plot, nonlinear curve fitting programs and competition binding assays); non-radioactive ligand binding assays (e.g., fluorescence polarization (FP), fluorescence resonance energy transfer (FRET); liquid phase ligand binding assays (e.g., real-time polymerase chain reaction (RT-qPCR), and immunoprecipitation); and solid phase ligand binding assays (e.g., multiwell plate assays, on-bead ligand binding assays, on-column ligand binding assays, and filter assays)) and surface plasmon resonance assays (see, e.g., Drescher et al., (2009) Methods Mol Biol 493:323-343 with commercially available instrumentation such as the Biacore 8+, Biacore S200, Biacore T200 (GE Healthcare Bio-Sciences, 100 Results Way, Marlborough MA 01752). In some embodiments, the present disclosure provides molecules (e.g., ILR binding sdAbs) that specifically bind to the hILR. As used herein, the binding affinity of an ILR binding molecule for the ILR, the binding affinity may be determined and/or quantified by surface plasmon resonance ("SPR"). In evaluating binding affinity of an ILR binding molecule for the ILR, either member of the binding pair may be immobilized, and the other element of the binding pair be provided in the mobile phase. In some embodiments, the sensor chip on which the protein of interest is to be immobilized is conjugated with a substance to facilitate binding of the protein of interest such as nitrilotriacetic acid (NTA) derivatized surface plasmon resonance sensor chips (e.g., Sensor Chip NTA available from Cytiva Global Life Science Solutions USA LLC, Marlborough MA as catalog number BR100407), as anti-His tag antibodies (e.g. anti-histidine CM5 chips commercially available from Cytiva, Marlborough MA), protein A or biotin. Consequently, to evaluate binding, it is frequently necessary to modify the protein to provide for binding to the substance conjugated to the surface of the chip. For example, the one member of the binding pair to be evaluated by incorporation of a chelating peptide comprising poly-histidine sequence (e.g., 6×His (SEQ ID NO: 230) or 8×His (SEQ ID NO: 231)) for retention on a chip conjugated with NTA. In some embodiments, the ILR binding molecule may be immobilized on the chip and ILR (or ECD fragment thereof) be provided in the mobile phase. Alternatively, the ILR (or ECD fragment thereof) may be immobilized on the chip and the ILR binding molecule be provided in the mobile phase. In either circumstance, it should be noted that modifications of some proteins for immobilization on a coated SPR chip may interfere with the binding properties of one or both components of the binding pair to be evaluated by SPR. In such cases, it may be necessary to switch the mobile and bound elements of the binding pair or use a chip with a binding agent that facilitates non-interfering conjugation of the protein to be evaluated. Alternatively, when evaluating the binding affinity of ILR binding molecule for ILR using SPR, the ILR binding molecule may be derivatized by the C-terminal addition of a poly-His sequence (e.g., 6×His (SEQ ID NO: 230) or 8×His (SEQ ID NO: 231)) and immobilized on the NTA derivatized sensor chip and the ILR receptor subunit for which the ILR VHH's binding affinity is being evaluated is provided in the mobile phase. The means for incorporation of a poly-His sequence into the C-terminus of the ILR binding molecule produced by recombinant DNA technology is well known to those of skill in the relevant art of biotechnology. In some embodiments, the binding affinity of ILR binding molecule for an ILR comprises using SPR substantially in accordance with the teaching of the Examples.

Substantially Pure: As used herein, the term "substantially pure" indicates that a component of a composition makes up greater than about 50%, alternatively greater than about 60%, alternatively greater than about 70%, alternatively greater than about 80%, alternatively greater than about 90%, alternatively greater than about 95% of the total content of the composition. A protein that is "substantially pure" comprises greater than about 50%, alternatively greater than about 60%, alternatively greater than about 70%, alternatively greater than about 80%, alternatively greater than about 90%, alternatively greater than about 95% of the total content of the composition.

T-cell: As used herein the term "T-cell" or "T cell" is used in its conventional sense to refer to a lymphocytes that differentiates in the thymus, possess specific cell-surface antigen receptors, and include some that control the initiation or suppression of cell-mediated and humoral immunity and others that lyse antigen-bearing cells. In some embodiments the T cell includes without limitation naïve CD8⁺ T cells, cytotoxic CD8⁺ T cells, naïve CD4⁺ T cells, helper T cells, e.g., $T_H1$, $T_H2$, $T_H9$, $T_H11$, $T_H22$, $T_{FH}$; regulatory T cells, e.g., $T_R1$, Tregs, inducible Tregs; memory T cells, e.g., central memory T cells, effector memory T cells, NKT cells, tumor infiltrating lymphocytes (TILs) and engineered variants of such T-cells including but not limited to CAR-T cells, recombinantly modified TILs and TCR-engineered cells. In some embodiments the T cell is a T cell expressing the IL12RB1 isoform referred to interchangeably as IL cell, IL12RB1+ cell, IL T cell, or IL12RB1+ T cell).

Terminus/Terminal: As used herein in the context of the structure of a polypeptide, "N-terminus" (or "amino terminus") and "C-terminus" (or "carboxyl terminus") refer to the extreme amino and carboxyl ends of the polypeptide, respectively, while the terms "N-terminal" and "C-terminal" refer to relative positions in the amino acid sequence of the polypeptide toward the N-terminus and the C-terminus, respectively, and can include the residues at the N-terminus and C-terminus, respectively. "Immediately N-terminal"

refers to the position of a first amino acid residue relative to a second amino acid residue in a contiguous polypeptide sequence, the first amino acid being closer to the N-terminus of the polypeptide. "Immediately C-terminal" refers to the position of a first amino acid residue relative to a second amino acid residue in a contiguous polypeptide sequence, the first amino acid being closer to the C-terminus of the polypeptide.

Transmembrane Domain: The term "transmembrane domain" or "TM" refers to a polypeptide domain of a membrane spanning polypeptide (e.g., a transmembrane receptor) which, when the membrane spanning polypeptide is associated with a cell membrane, is which is embedded in the cell membrane and is in peptidyl linkage with the extracellular domain (ECD) and the intracellular domain (ICD) of a membrane spanning polypeptide. A transmembrane domain may be homologous (naturally associated with) or heterologous (not naturally associated with) with either or both of the extracellular and/or intracellular domains. In some embodiments, where the receptor is a chimeric receptor comprising the intracellular domain derived from a first parental receptor and a second extracellular domains are derived from a second different parental receptor, the transmembrane domain of the chimeric receptor is the transmembrane domain normally associated with either the ICD or the ECD of the parent receptor from which the chimeric receptor is derived.

Treg Cell or Regulatory T Cell. The terms "regulatory T cell", "Treg cell", or "Treg" are interchangeably herein to refers to a type of CD4$^+$ T cell that can suppress the responses of other T cells including but not limited to effector T cells (Teff). Treg cells are typically characterized by expression of CD4 (CD4+), the CD25 subunit of the IL2 receptor (CD25+), and the transcription factor forkhead box P3 (FOXP3+) (Sakaguchi, Annu Rev Immunol 22, 531-62 (2004). In some instances, the term "conventional CD4$^+$ T cells" is used to distinguish non-Treg CD4$^+$ T cells from CD4$^+$ Tregs.

Variant: The terms "variant", "protein variant" or "variant protein" or "variant polypeptide" are used interchangeably herein to refer to a polypeptide that differs from a parent polypeptide by virtue of at least one amino acid modification, substitution, or deletion. The parent polypeptide may be a naturally occurring or wild-type (WT) polypeptide or may be a modified version of a WT polypeptide. The term variant polypeptide may refer to the polypeptide itself, a composition comprising the polypeptide, or the nucleic acid sequence that encodes it. In some embodiments, the variant polypeptide comprises from about one to about ten, alternatively about one to about eight, alternatively about one to about seven, alternatively about one to about five, alternatively about one to about four, alternatively from about one to about three alternatively from one to two amino acid modifications, substitutions, or deletions, or alternatively a single amino acid amino acid modification, substitution, or deletion compared to the parent polypeptide. A variant may be at least about 99% identical, alternatively at least about 98% identical, alternatively at least about 97% identical, alternatively at least about 95% identical, or alternatively at least about 90% identical to the parent polypeptide from which the variant is derived.

VHH: As used herein, the term "VHH" is a type of sdAb that has a single monomeric heavy chain variable antibody domain. Such antibodies can be found in or produced from Camelid mammals (e.g., camels, llamas) which are naturally devoid of light chainsVHHs can be obtained from immunization of camelids (including camels, llamas, and alpacas (see, e.g., Hamers-Casterman, et al. (1993) Nature 363:446-448) or by screening libraries (e.g., phage libraries) constructed in VHH frameworks. Antibodies having a given specificity may also be derived from non-mammalian sources such as V$_H$Hs obtained from immunization of cartilaginous fishes including, but not limited to, sharks. In a particular embodiment, a VHH in a bispecific V$_H$H$^2$ binding molecule described herein binds to a receptor (e.g., the first receptor or the second receptor of the natural or non-natural receptor pairs) if the equilibrium dissociation constant (K$_D$) between the VHH and the receptor is lesser than about $10^{-6}$ M, alternatively lesser than about $10^{-8}$ M, alternatively lesser than about 1010 M, alternatively lesser than about $10^{-11}$ M, alternatively lesser than about 1010 M, lesser than about 1012 M as determined by, e.g., Scatchard analysis (Munsen, et al. 1980 Analyt. Biochem. 107:220-239). Standardized protocols for the generation of single domain antibodies from camelids are well known in the scientific literature. See, e.g., Vincke, et al (2012) Chapter 8 in *Methods in Molecular Biology*, Walker, J. editor (Humana Press, Totowa NJ). Specific binding may be assessed using techniques known in the art including but not limited to competition ELISA, BIACORE® assays and/or KINEXA® assays. In some embodiments, a VHH described herein can be humanized to contain human framework regions. Examples of human germlines that could be used to create humanized V$_H$Hs include, but are not limited to, VH3-23 (e.g., UniProt ID: P01764), VH3-74 (e.g., UniProt ID: A0A0B4J1X5), VH3-66 (e.g., UniProt ID: A0A0C4DH42), VH3-30 (e.g., UniProt ID: P01768), VH3-11 (e.g., UniProt ID: P01762), and VH3-9 (e.g., UniProt ID: P01782).

Wild Type: By "wild type" or "WT" or "native" herein is meant an amino acid sequence or a nucleotide sequence that is found in nature, including allelic variations. A wild-type protein, polypeptide, antibody, immunoglobulin, IgG, etc. has an amino acid sequence or a nucleotide sequence that has not been modified by the hand of man.

IL12RB1

The IL12RB1 binding molecules of the present disclosure specifically bind to the extracellular domain of the IL12RB1.

Human IL12RB1

In one embodiment, specifically bind to the extracellular domain of the human IL receptor subunit (hIL12RB1). hIL12RB1 is expressed as a 662 amino acid precursor comprising a 23 amino acid N-terminal signal sequence which is post-translationally cleaved to provide an 639 amino acid mature protein. The canonical full-length acid hIL12RB1 precursor (including the signal peptide) is a 662 amino acid polypeptide having the amino acid sequence:

```
                                          (SEQ ID NO: 1)
MEPLVTWVVPLLFLFLLSRQGAACRTSECCFQDPP

YPDADSGSASGPRDLRCYRISSDRYECSWQYEGPT

AGVSHFLRCCLSSGRCCYFAAGSATRLQFSDQAGV

SVLYTVTLWVESWARNQTEKSPEVTLQLYNSVKYE

PPLGDIKVSKLAGQLRMEWETPDNQVGAEVQFRHR

TPSSPWKLGDCGPQDDDTESCLCPLEMNVAQEFQL

RRRQLGSQGSSWSKWSSPVCVPPENPPQPQVRFSV

EQLGQDGRRRLTLKEQPTQLELPEGCQGLAPGTEV
```

```
TYRLQLHMLSCPCKAKATRTLHLGKMPYLSGAAYN

VAVISSNQFGPGLNQTWHIPADTHTEPVALNISVG

TNGTTMYWPARAQSMTYCIEWQPVGQDGGLATCSL

TAPQDPDPAGMATYSWSRESGAMGQEKCYYITIFA

SAHPEKLTLWSTVLSTYHFGGNASAAGTPHHVSVK

NHSLDSVSVDWAPSLLSTCPGVLKEYVVRCRDEDS

KQVSEHPVQPTETQVTLSGLRAGVAYTVQVRADTA

WLRGVWSQPQRFSIEVQVSDWLIFFASLGSFLSIL

LVGVLGYLGLNRAARHLCPPLPTPCASSAIEFPGG

KETWQWINPVDFQEEASLQEALVVEMSWDKGERTE

PLEKTELPEGAPELALDTELSLEDGDRCKAKM.
```

For purposes of the present disclosure, the numbering of amino acid residues of the human IL12RB1 polypeptides as described herein is made in accordance with the numbering of this canonical sequence (UniProt Reference No P42701, SEQ ID NO:1). Amino acids 1-23 of SEQ ID NO:1 are identified as the signal peptide of hIL12RB1, amino acids 24-545 of SEQ ID NO:1 are identified as the extracellular domain, amino acids 546-570 of SEQ ID NO:1 are identified as the transmembrane domain, and amino acids 571-662 of SEQ ID NO:1 are identified as the intracellular domain.

For the purposes of generating antibodies that bind to the ECD of IL12RB1, immunization may be performed with the extracellular domain of the hIL12RB1. The extracellular domain of hIL12RB1 is a 522 amino acid polypeptide of the sequence:

```
                                    (SEQ ID NO: 227)
CRTSECCFQDPPYPDADSGSASGPRDLRCYRISSD

RYECSWQYEGPTAGVSHFLRCCLSSGRCCYFAAGS

ATRLQFSDQAGVSVLYTVTLWVESWARNQTEKSPE

VTLQLYNSVKYEPPLGDIKVSKLAGQLRMEWETPD

NQVGAEVQFRHRTPSSPWKLGDCGPQDDDTESCLC

PLEMNVAQEFQLRRRQLGSQGSSWSKWSSPVCVPP

ENPPQPQVRFSVEQLGQDGRRRLTLKEQPTQLELP

EGCQGLAPGTEVTYRLQLHMLSCPCKAKATRTLHL

GKMPYLSGAAYNVAVISSNQFGPGLNQTWHIPADT

HTEPVALNISVGTNGTTMYWPARAQSMTYCIEWQP

VGQDGGLATCSYHFGGNASAAGTPHHVSVKNHSLD

SVSVDWAPSLLSTCPGVLKEYVVRCRDEDSKQVSE

HPVQPTETQVTLSGLRAGVAYTVQVRADTAWLRGV

WSQPQRFSIEVQVSD.
```

Mouse IL12RB1

In one embodiment, specifically bind to the extracellular domain of the mouse or murine IL12RB1 receptor subunit (mIL12RB1). mIL12RB1 is expressed as a 738 amino acid precursor comprising a 19 amino acid N-terminal signal sequence which is post-translationally cleaved to provide a 719 amino acid mature protein. The canonical full-length acid mIL12RB1 precursor (including the 24 amino acid signal peptide) is a 738 amino acid polypeptide having the amino acid sequence:

```
                                    (SEQ ID NO: 228)
MDMMGLAGTSKHITFLLLCQLGASGPGDGCCVEKT

SFPEGASGSPLGPRNLSCYRVSKTDYECSWQYDGP

EDNVSHVLWCCFVPPNHTHTGQERCRYFSSGPDRT

VQFWEQDGIPVLSKVNFWVESRLGNRTMKSQKISQ

YLYNWTKTTPPLGHIKVSQSHRQLRMDWNVSEEAG

AEVQFRRRMPTTNWTLGDCGPQVNSGSGVLGDIRG

SMSESCLCPSENMAQEIQIRRRRRLSSGAPGGPWS

DWSMPVCVPPEVLPQAKIKFLVEPLNQGGRRRLTM

QGQSPQLAVPEGCRGRPGAQVKKHLVLVRMLSCRC

QAQTSKTVPLGKKLNLSGATYDLNVLAKTRFGRST

IQKWHLPAQELTETRALNVSVGGNMTSMQWAAQAP

GTTYCLEWQPWFQHRNHTHCTLIVPEEEDPAKMVT

HSWSSKPTLEQEECYRITVFASKNPKNPMLWATVL

SSYYFGGNASRAGTPRHVSVRNQTGDSVSVEWTAS

QLSTCPGVLTQYVVRCEAEDGAWESEWLVPPTKTQ

VTLDGLRSRVMYKVQVRADTARLPGAWSHPQRFSF

EVQISRLSIIFASLGSFASVLLVGSLGYIGLNRAA

WHLCPPLPTPCGSTAVEFPGSQGKQAWQWCNPEDF

PEVLYPRDALVVEMPGDRGDGTESPQAAPECALDT

RRPLETQRQRQVQALSEARRLGLAREDCPRGDLAH

VTLPLLLGGVTQGASVLDDLWRTHKTAEPGPPTLG

QEA
```

For purposes of the present disclosure, the numbering of amino acid residues of the mIL12RB1 polypeptides as described herein is made in accordance with the numbering of this canonical sequence (UniProt Reference No. Q60837, SEQ ID NO:228). Amino acids 1-19 of SEQ ID NO:228 are identified as the signal peptide of mIL12RB1, amino acids 20-565 of SEQ ID NO:228 are identified as the extracellular domain, amino acids 566-591 of SEQ ID NO:228 are identified as the transmembrane domain, and amino acids 592-738 of SEQ ID NO:228 are identified as the intracellular domain.

For the purposes of generating antibodies that bind to the ECD of IL12RB1, immunization may be performed with the extracellular domain of the mIL12RB1. The extracellular domain of the mIL12RB1 receptor is a 546 amino acid polypeptide of the sequence:

```
                                    (SEQ ID NO: 229)
QLGASGPGDGCCVEKTSFPEGASGSPLGPRNLSCY

RVSKTDYECSWQYDGPEDNVSHVLWCCFVPPNHTH

TGQERCRYFSSGPDRTVQFWEQDGIPVLSKVNFWV

ESRLGNRTMKSQKISQYLYNWTKTTPPLGHIKVSQ
```

```
         -continued
SHRQLRMDWNVSEEAGAEVQFRRRMPTTNWTLGDC

GPQVNSGSGVLGDIRGSMSESCLCPSENMAQEIQI

RRRRRLSSGAPGGPWSDWSMPVCVPPEVLPQAKIK

FLVEPLNQGGRRRLTMQGQSPQLAVPEGCRGRPGA

QVKKHLVLVRMLSCRCQAQTSKTVPLGKKLNLSGA

TYDLNVLAKTRFGRSTIQKWHLPAQELTETRALNV

SVGGNMTSMQWAAQAPGTTYCLEWQPWFQHRNHTH

CTLIVPEEEDPAKMVTHSWSSKPTLEQEECYRITV

FASKNPKNPMLWATVLSSYYFGGNASRAGTPRHVS

VRNQTGDSVSVEWTASQLSTCPGVLTQYVVRCEAE

DGAWESEWLVPPTKTQVTLDGLRSRVMYKVQVRAD

TARLPGAWSHPQRFSFEVQIS.
```

IL12Rb1 Binding Molecules and Single Domain Antibodies

In some embodiments, a IL12Rb1 binding molecule of the present disclosure is a single domain antibody (sdAb). The present disclosure relates to IL12Rb1 binding molecules comprising single domain antibodies (sdAbs) that specifically bind to the extracellular domain of the human IL12Rb1 isoform (hIL12Rb1) which are found on all IL12Rb1-expressing cells.

A single-domain antibody (sdAb) is an antibody containing a single monomeric variable antibody domain. Like a full-length antibody, sdAbs are able to bind specifically to an antigenic determinant. hIL12RB1 binding VHH single-domain antibodies can be engineered from heavy chain antibodies isolated from Camelidae mammals (e.g., camels, llamas, dromedary, alpaca, and guanaco) immunized with the extracellular domain of hIL12RB1 or an immunologically active fragment thereof. Descriptions of sdAbs and VHHs can be found in, e.g., De Greve et al., (2019) Curr Opin Biotechnol. 61:96-101; Ciccarese, et al., (2019) Front Genet. 10:997: Chanier and Chames (2019) *Antibodies* (Basel) 8(1); and De Vlieger, et al. (2018) *Antibodies* (Basel) 8(1). Alternatively, hIL12RB1 single domain antibodies may be engineered from heavy chain antibodies isolated from the IgNAR heavy chain antibodies isolated from cartilaginous fishes immunized with the extracellular domain of hIL12RB1 or an immunologically active fragment thereof. hIL12RB1 binding sdAbs may also be obtained by splitting the dimeric variable domains from immunoglobulin G (IgG) isotypes from other mammalian species including humans, rats, rabbits immunized with the extracellular domain of hIL12RB1 or an immunologically active fragment thereof. Although most research into sdAbs is currently based on heavy chain variable domains, sdAbs derived from light chains have also been shown to bind specifically to the target proteins comprising the antigenic immunization sequence. Moller et al., *J Biol Chem.* 285(49): 38348-38361, 2010.

In some embodiments, the sdAb is a VHH. A VHH is a type of sdAb that has a single monomeric heavy chain variable antibody domain. Similar to a traditional antibody, a VHH is able to bind specifically to a specific antigen. An exemplary VHH has a molecular weight of approximately 12-15 kDa which is much smaller than traditional mammalian antibodies (150-160 kDa) composed of two heavy chains and two light chains. VHHs can be found in or produced from Camelidae mammals (e.g., camels, llamas, dromedary, alpaca, and guanaco) which are naturally devoid of light chains.

The present disclosure provides IL12RB1 binding molecules comprising a polypeptide having at least 75%, alternatively 80%, alternatively 90%, alternatively 95%, alternatively 98%, or alternatively 99% or 100% identity to a polypeptide of any one of SEQ ID NOS:2-22.

The present disclosure provides IL12RB1 binding molecules comprising a CDR1, a CDR2, and a CDR3 as described in a row of Table 1A provided herein. In some embodiments, the CDR1, CDR2, and CDR3 can each, independently, comprise at least 90% (e.g., 91%, 92%, 93%, 94%, 95%, 96%, 97%, 98%, 99%, or 100%) sequence identity, or have 0, 1, 2, or 3 amino acid changes, optionally conservative amino acid changes, relative to the sequence described in a row of Table 1 or 4 provided herein.

EXPERIMENTAL

The single domain antibodies of the present disclosure were obtained from camels by immunization with an extracellular domain of a IL12Rb1 receptor. IL12Rb1 VHH molecules of the present disclosure of the present disclosure were generated in substantial accordance with the teaching of the Examples. Briefly, a camel was sequentially immunized with the ECD of the human IL12Rb1 and mouse IL12Rb1 over a period several weeks of by the subcutaneous an adjuvanted composition containing a recombinantly produced fusion proteins comprising the extracellular domain of the IL12Rb1, the human IgG1 hinge domain and the human IgG1 heavy chain Fc. Following immunization, RNAs extracted from a blood sample of appropriate size VHH-hinge-CH2-CH3 species were transcribed to generate DNA sequences, digested to identify the approximately 400 bp fragment comprising the nucleic acid sequence encoding the VHH domain was isolated. The isolated sequence was digested with restriction endonucleases to facilitate insertion into a phagemid vector for in frame with a sequence encoding a his-tag and transformed into *E. coli* to generate a phage library. Multiple rounds of biopanning of the phage library were conducted to identify VHHs that bound to the ECD of IL12Rb1 (human or mouse as appropriate). Individual phage clones were isolated for periplasmic extract ELISA (PE-ELISA) in a 96-well plate format and selective binding confirmed by colorimetric determination. The IL12Rb1 binding molecules that demonstrated specific binding to the IL12Rb1 antigen were isolated and sequenced and sequences analyzed to identify VHH sequences, CDRs and identify unique VHH clonotypes. As used herein, the term "clonotypes" refers a collection of binding molecules that originate from the same B-cell progenitor cell, in particular collection of antigen binding molecules that belong to the same germline family, have the same CDR3 lengths, and have 70% or greater homology in CDR3 sequence. The VHH molecules demonstrating specific binding to the hIL12Rb1 ECD antigen (anti-human IL12Rb1 VHHs) and the CDRs isolated from such VHHs are provided in Table 1. The VHH molecules demonstrating specific binding to the mIL12Rb1 ECD antigen (anti-mouse IL12Rb1 VHHs) are provided in Table 4 and the CDRs isolated from such VHHs are provided in Table 3. Nucleic acid sequences encoding the VHHs of Table 1 and 4 are provide in Tables 2 and 5 respectively.

In some instances, due to sequence or structural similarities between the extracellular domains of IL12Rb1 receptors from various mammalian species, immunization with an antigen derived from a IL12Rb1 of a first mammalian species (e.g., the hIL12Rb1-ECD) may provide antibodies which specifically bind to IL12Rb1 receptors of one or more additional mammalian species. Such antibodies are termed "cross reactive." For example, immunization of a camelid with a human derived antigen (e.g., the hIL12Rb1-ECD) may generate antibodies that are cross-reactive the murine and human receptors. Evaluation of cross-reactivity of antibody with respect to the receptors derived from other mammalian species may be readily determined by the skilled artisan, for example using the methods relating to evaluation of binding affinity and/or specific binding described elsewhere herein such as flow cytometry or SPR. Consequently, the use of the term "human IL12Rb1 VHH" or "hIL12Rb1 VHH" merely denotes that the species of the IL12Rb1 antigen used for immunization of the camelid from which the VHH was derived was the human IL12Rb1 (e.g., the hIL12Rb1, ECD, SEQ ID NO:192 but should not be understood as limiting with respect to the specific binding affinity of the VHH for hIL12Rb1 molecules of other mammalian species. Similarly, the use of the term "mouse IL12Rb1 VHH" or "mIL12Rb1" merely denotes that the species of the IL12Rb1 antigen used for immunization of the camelid from which the VHH was derived was the murine IL12Rb1 (e.g., the mIL12Rb1 ECD, SEQ ID NO:194) but should not be understood as limiting with respect to the specific binding affinity of the VHH for IL12Rb1 molecules of other mammalian species.

Modified Forms of Single Domain Antibodies

CDR Grafted sdAbs

In some embodiments, the IL12RB1 binding sdAb of the present disclosure is a CDR grafted IL12RB1 binding sdAb. CDRs obtained from antibodies, heavy chain antibodies, and sdAbs derived therefrom may be grafted onto alternative frameworks as described in Saerens, et al. (2005) J. Mol Biol 352:597-607 to generate CDR-grafted sdAbs. In some embodiments, the present disclosure provides a IL12RB1 binding molecule comprising a CDR grafted IL binding sdAb, said CDR-grafted IL binding sdAb comprising a set of CDRs1, 2, and 3 as shown in a row of the Table 1A above. In some embodiments, the present disclosure provides a IL12RB1 binding molecule comprising a CDR grafted IL12RB1 binding sdAb, said CDR-grafted IL binding sdAb comprising a set of CDRs1, 2, and 3 as shown in a row of the Table 1A above.

Elimination of N-Linked Glycosylation Sites

In some embodiments, it is possible that an amino acid sequence (particularly a CDR sequence) of the IL binding sdAb may contain a glycosylation motif, particularly an N-linked glycosylation motif of the sequence Asn-X-Ser (N-X-S) or Asn-X-Thr (N-X-T), wherein X is any amino acid except for proline. In such instances, it is desirable to eliminate such N-linked glycosylation motifs by modifying the sequence of the N-linked glycosylation motif to prevent glycosylation. In some embodiments, the elimination of the Asn-X-Ser (N-X-S) N-linked glycosylation motif may be achieved by the incorporation of conservative amino acid substitution of the Asn (N) residue and/or Ser (S) residue of the Asn-X-Ser (N-X-S) N-linked glycosylation motif. In some embodiments, the elimination of the Asn-X-Thr (N-X-T) N-linked glycosylation motif may be achieved by the incorporation of conservative amino acid substitution of the Asn (N) residue and/or Thr (T) residue of the Asn-X-Thr (N-X-T) N-linked glycosylation motif. In some embodiments, elimination of the As procaryotic host cells do not provide the mechanism for glycosylation of recombinant proteins, when employing a procaryotic expression system to produce a recombinant recombinant IL12RB1 binding sdAb the modification of the sequence to eliminate the N-linked glycosylation sites may be obviated.

Chimeric and Humanized sdAbs

Any framework region can be used with the CDRs as described herein. In some embodiments, the IL12RB1 binding sdAb is a chimeric sdAb, in which the CDRs are derived from one species (e.g., camel) and the framework and/or constant regions are derived from another species (e.g., human or mouse). In specific embodiments, the framework regions are human or humanized sequences. Thus, humanized IL12RB1 binding sdAbs derived from hIL12RB1 binding VHHs are considered within the scope of the present disclosure. The techniques for humanization of camelid single domain antibodies are well known in the art. See, e.g., Vincke, et al. (2009) *General Strategy to Humanize a Camelid Single-domain Antibody and Identification of a Universal Humanized Nanobody Scaffold* J. Biol. Chem. 284(5)3273-3284.

In some embodiments, a VHH described herein can be humanized to contain human framework regions. Examples of human germlines that could be used to create humanized VHHs include, but are not limited to, VH3-23 (e.g., UniProt ID: P01764), VH3-74 (e.g., UniProt ID: A0A0B4J1X5), VH3-66 (e.g., UniProt ID: A0A0C4DH42), VH3-30 (e.g., UniProt ID: P01768), VH3-11 (e.g., UniProt ID: P01762), and VH3-9 (e.g., UniProt ID: P01782).

IL12Rb1 Binding Molecules Comprising Additional Agents

In some embodiments, a IL12Rb1 binding molecule of the present disclosure comprises a IL12Rb1 single domain antibody (sdAb) is operably linked to to one or more additional biologically active agents including but not limited to, therapeutic agents, chemically, optically or radioactively active agents, including combinations thereof. The conjugation of at least one such biologically, chemically, optically or radioactively active agent confer additional biological or chemical properties to IL binding sdAb, the combination providing a IL12Rb1 binding molecule possessing additional or alternative utilities.

For example, the additional agent may be a molecule selected from one or more of: immunomodulatory agents (e.g., immunogens); molecules that improve aqueous solubility (e.g., water soluble polymers and hydrophilic molecules such as sugars); carrier molecules that extend in vivo half-life (e.g., PEGylation, Fc fusions or acylation); generation of antibodies for use in detection assays (e.g., epitope tags), enhance ease of purification (e.g., chelating peptides such as poly-His tags); targeting domains that provide selective targeting IL12Rb1 binding molecule to a particular cell or tissue type; therapeutic agents (e.g., therapeutic agents including small molecule or polypeptide agents); agents that visibility to optical or electromagnetic sensors (e.g., radionucleotides or fluorescent agents). In some embodiments, the linker is a cleavable linker or a non-cleavable linker. The use of a cleavable linker in a IL12Rb1 binding molecule as contemplated herein facilitates the release of a therapeutic agent into the intracellular cytoplasm upon internalization of the IL12Rb1 binding molecule. A non-cleavable linker would allow release upon digestion of the IL12Rb1 binding molecule of or it could be used with an agent that does not require release from the antibody (e.g., an imaging agent).

In some embodiments, where the IL12Rb1 binding molecule comprises a IL binding sdAb in stable association with an additional agent joined via a linker. A linker is a covalent linkage between two elements of a IL12Rb1 binding molecule (e.g., a hIL12Rb1 binding VHH and PEG polymer). A linker can be a covalent bond, chemical linker or a peptide linker. Suitable linkers include "flexible linkers" which are generally of sufficient length to permit some movement between the IL binding sdAb and the linked agent(s). Examples of chemical linkers include aryl acetylene, ethylene glycol oligomers containing 2-10 monomer units, diamines, diacids, amino acids, or combinations thereof. In some embodiments, the linker is a peptide linker. Suitable peptide linkers can be readily selected and can be of any suitable length, such as 1 amino acid (e.g., Gly), 2, 3, 4, 5, 6, 7, 8, 9, 10, 10-20, 20-30, 30-50 or more than 50 amino acids. Suitable peptide linkers are known in the art, and include, for example, peptide linkers containing flexible amino acid residues such as glycine and serine. Examples of flexible linkers include glycine polymers $(G)_n$, glycine-serine polymers, glycine-alanine polymers, alanine-serine polymers, and other flexible linkers. Glycine and glycine-serine polymers are relatively unstructured, and therefore can serve as a neutral tether between components. Further examples of flexible linkers include glycine polymers $(G)_n$, glycine-alanine polymers, alanine-serine polymers, glycine-serine polymers. Glycine and glycine-serine polymers are relatively unstructured, and therefore may serve as a neutral tether between components. A multimer (e.g., 1, 2, 3, 4, 5, 6, 7, 8, 9, 10, 10-20, 20-30, or 30-50) of such linker sequences may be linked together to provide flexible linkers that may be used to conjugate a heterologous amino acid sequence to IL12RB1 binding sdAbs disclosed herein. In some embodiments the linkers have the formula (GGGS)n (SEQ ID NO: 232), (GGGSG)n (SEQ ID NO: 233), or (GGSG)n (SEQ ID NO: 234), wherein n is an integer selected from 1, 2, 3, 4, 5, 6, 7, 8, 9 and 10.

Immunomodulatory Agents

In some embodiments, the IL binding molecule is operably linked to n immunomodulatory agent (immunoconjugates). Examples of immunomodulatory agents that may operably linked to the hIL12RB1 binding sdAb of the present disclosure include, but are not limited to, inactivated virus particles, inactivated bacterial toxins such as toxoid from diphtheria, tetanus, cholera, or leukotoxin molecules, inactivated bacteria and dendritic cells. Such immunoconjugates are useful in facilitating an immune response against the IL12RB1 or cells expressing the IL12RB1.

Flag Tags

In one embodiment, the present disclosure provides a IL12Rb1 binding molecule operably linked to an antigenic tag, such as a FLAG sequence. FLAG sequences are recognized by biotinylated, highly specific, anti-FLAG antibodies, as described herein (see e.g., Blanar et al. (1992) Science 256:1014 and LeClair, et al. (1992) PNAS-USA 89:8145). In some embodiments, the IL12RB1 binding sdAb polypeptide further comprises a C-terminal c-myc epitope tag.

Chelating Peptides

In one embodiment, the present disclosure provides a IL12RB1 binding molecule is operably linked to one or more transition metal chelating polypeptide sequences. The incorporation of such a transition metal chelating domain facilitates purification immobilized metal affinity chromatography (IMAC) as described in Smith, et al. U.S. Pat. No. 4,569,794 issued Feb. 11, 1986. Examples of transition metal chelating polypeptides useful in the practice of the present IL12RB1 binding molecule are described in Smith, et al. supra and Dobeli, et al. U.S. Pat. No. 5,320,663 issued May 10, 1995, the entire teachings of which are hereby incorporated by reference. Particular transition metal chelating polypeptides useful in the practice of the present IL12RB1 binding molecule are polypeptides comprising 3-6 contiguous histidine residues (SEQ ID NO: 235) such as a six-histidine $(His)_6$ (SEQ ID NO: 230) peptide and are frequently referred to in the art as "His-tags." In addition to providing a purification "handle" for the recombinant proteins or to facilitate immobilization on SPR sensor chips, such the conjugation of the hIL12RB1 binding molecule to a chelating peptide facilitates the targeted delivery to IL12RB1 expressing cells of transition metal ions as kinetically inert or kinetically labile complexes in substantial accordance with the teaching of Anderson, et al., (U.S. Pat. No. 5,439,829 issued Aug. 8, 1995 and Hale, J. E (1996) Analytical Biochemistry 231(1):46-49. The transition metal ion is a reporter molecule such as a fluorescent compound or radioactive agent, including as radiological imaging or therapeutic agents.

Carrier Molecules

In some embodiments the IL12RB1 binding sdAbs of the present disclosure is operably linked to one or more carrier molecules. Carrier molecules are typically large, slowly metabolized macromolecules which provide for stabilization and/or extended duration of action in vivo. Examples of in vivo carriers that may be incorporated into IL12Rb1 binding molecules, but are not limited to: proteins (including but not limited to human serum albumin); fatty acids (acylation); polysaccharides (including but not limited to (N- and O-linked) sugars, sepharose, agarose, cellulose, or cellulose); polypeptdies amino acid copolymers, acylation, or polysialylation, an polyethylene glycol (PEG) polymers.

Water Soluble Polymers

In some embodiments, the IL12RB1 binding sdAb is conjugated to one or more water-soluble polymers. Examples of water soluble polymers useful in the practice of the present IL12Rb1 binding molecule include polyethylene glycol (PEG), poly-propylene glycol (PPG), polysaccharides (polyvinylpyrrolidone, copolymers of ethylene glycol and propylene glycol, poly(oxyethylated polyol), polyolefinic alcohol, polysaccharides, poly-alpha-hydroxy acid, polyvinyl alcohol (PVA), polyphosphazene, polyoxazolines (POZ), poly(N-acryloylmorpholine), or a combination thereof.

Polyethylene Glycol

In one embodiment, the carrier molecule is a polyethylene glycol ("PEG") polymer. Conjugation of PEG polymers to proteins (PEGylation) is a well-established method for the extension of serum half-life of biological agents. The PEGylated polypeptide may be further referred to as monopegylated, dipegylated, tripegylated (and so forth) to denote a polypeptide comprising one, two, three (or more) PEG moieties attached to the polypeptide, respectively. In some embodiments, the PEG may be covalently attached directly to the sdAb (e.g., through a lysine side chain, sulfhydryl group of a cysteine or N-terminal amine) or optionally employ a linker between the PEG and the sdAb. In some embodiments, a IL12Rb1 binding molecule comprises more than one PEG molecules each of which is attached to a different amino acid residue. In some embodiments, the sdAb may be modified by the incorporation of non-natural amino acids with non-naturally occurring amino acid side chains to facilitate site specific PEGylation. In other embodiments, cysteine residues may be substituted at one or more positions within the sdAb to facilitate site-specific PEGylation via the cysteine sulfhydryl side chain.

In some instances, the IL12RB1 binding molecules of the present disclosure possess an N-terminal glutamine ("1Q") residue. N-terminal glutamine residues have been observed to spontaneously cyclyize to form pyroglutamate (pE) at or near physiological conditions. (See e.g., Liu, et al (2011) J. Biol. Chem. 286(13): 11211-11217). In some embodiments, the formation of pyroglutamate complicates N-terminal PEG conjugation particularly when aldehyde chemistry is used for N-terminal PEGylation. Consequently, when PEGylating the IL12RB1 binding molecules of the present disclosure, particularly when aldehyde chemistry is to be employed, the IL12RB1 binding molecules possessing an amino acid at position 1 (e.g., 1Q) are substituted at position 1 with an alternative amino acid or are deleted at position 1 (e.g., des-1Q). In some embodiments, the IL12RB1 binding molecules of the present disclosure comprise an amino acid substitution selected from the group Q1E and Q1D.

PEGs suitable for conjugation to a polypeptide sequence are generally soluble in water at room temperature, and have the general formula $$R(O—CH_2—CH_2)_nO—R,$$

where R is hydrogen or a protective group such as an alkyl or an alkanol group, and where n is an integer from 1 to 1000. When R is a protective group, it generally has from 1 to 8 carbons. The PEG can be linear or branched. Branched PEG derivatives, "star-PEGs" and multi-armed PEGs are contemplated by the present disclosure.

A molecular weight of the PEG used in a IL12Rb1 binding molecule is not restricted to any particular range. The PEG component of a IL12Rb1 binding molecule can have a molecular mass greater than about 5 kDa, greater than about 10 kDa, greater than about 15 kDa, greater than about 20 kDa, greater than about 30 kDa, greater than about 40 kDa, or greater than about 50 kDa. In some embodiments, the molecular mass is from about 5 kDa to about 10 kDa, from about 5 kDa to about 15 kDa, from about 5 kDa to about 20 kDa, from about 10 kDa to about 15 kDa, from about 10 kDa to about 20 kDa, from about 10 kDa to about 25 kDa or from about 10 kDa to about 30 kDa. Linear or branched PEG molecules having molecular weights from about 2,000 to about 80,000 daltons, alternatively about 2,000 to about 70,000 daltons, alternatively about 5,000 to about 50,000 daltons, alternatively about 10,000 to about 50,000 daltons, alternatively about 20,000 to about 50,000 daltons, alternatively about 30,000 to about 50,000 daltons, alternatively about 20,000 to about 40,000 daltons, alternatively about 30,000 to about 40,000 daltons. In one embodiment of the IL12Rb1 binding molecule, the PEG is a 40 kD branched PEG comprising two 20 kD arms.

The present disclosure also contemplates a IL12Rb1 binding molecule comprising more than one PEG moiety wherein the PEGs have different sizes values, and thus the various different PEGs are present in specific ratios. For example, in the preparation of a PEGylated IL12Rb1 binding molecule, some compositions comprise a mixture of mono-, di-, tri-, and quadra-PEGylated sdAb conjugates. In some compositions, the percentage of mono-PEGylated species is 18-25%, the percentage of di-PEGylated species is 50-66%, the percentage of tri-pegylated species is 12-16%, and the percentage of quadra-pegylated species up to 5%. Such complex compositions can be produced by reaction conditions and purification methods known in the art. Chromatography may be used to resolve conjugate fractions, and a fraction is then identified which contains the conjugate having, for example, the desired number of PEGs attached, purified free from unmodified protein sequences and from conjugates having other numbers of PEGs attached.

PEGylation most frequently occurs at the α-amino group at the N-terminus of the polypeptide, the epsilon amino group on the side chain of lysine residues, and the imidazole group on the side chain of histidine residues. Since most recombinant polypeptides possess a single alpha and a number of epsilon amino and imidazole groups, numerous positional isomers can be generated depending on the linker chemistry.

Two widely used first generation activated monomethoxy PEGs (mPEGs) are succinimdyl carbonate PEG (SC-PEG; see, e.g., Zalipsky, et al. (1992) Biotehnol. Appl. Biochem 15:100-114) and benzotriazole carbonate PEG (BTC-PEG; see, e.g., Dolence, et al. U.S. Pat. No. 5,650,234), which react preferentially with lysine residues to form a carbamate linkage but are also known to react with histidine and tyrosine residues. Use of a PEG-aldehyde linker targets a single site on the N-terminus of a polypeptide through reductive amination.

The PEG can be bound to a IL12Rb1 binding molecule of the present disclosure via a terminal reactive group (a "spacer") which mediates a bond between the free amino or carboxyl groups of one or more of the polypeptide sequences and polyethylene glycol. The PEG having the spacer which can be bound to the free amino group includes N-hydroxysuccinylimide polyethylene glycol, which can be prepared by activating succinic acid ester of polyethylene glycol with N-hydroxysuccinylimide.

In some embodiments, the PEGylation of the sdAb is facilitated by the incorporation of non-natural amino acids bearing unique side chains to facilitate site specific PEGylation. The incorporation of non-natural amino acids into polypeptides to provide functional moieties to achieve site specific PEGylation of such polypeptides is known in the art. See e.g., Ptacin, et al., PCT International Application No. PCT/US2018/045257 filed Aug. 3, 2018 and published Feb. 7, 2019 as International Publication Number WO 2019/028419A1.

The PEG moiety of the of a PEGylated IL12Rb1 binding molecule may be linear or branched. Branched PEG derivatives, "star-PEGs" and multi-armed PEGs are contemplated by the present disclosure. Specific embodiments PEGs useful in the practice of the present disclosure include a 10 kDa linear PEG-aldehyde (e.g., Sunbright® ME-100AL, NOF America Corporation, One North Broadway, White Plains, NY 10601 USA), 10 kDa linear PEG-NETS ester (e.g., Sunbright® ME-100CS, Sunbright® ME-100AS, Sunbright® ME-100GS, Sunbright® ME-100HS, NOF), a 20 kDa linear PEG-aldehyde (e.g., Sunbright® ME-200AL, NOF, a 20 kDa linear PEG-NHS ester (e.g., Sunbright® ME-200CS, Sunbright® ME-200AS, Sunbright® ME-200GS, Sunbright® ME-200HS, NOF), a 20 kDa 2-arm branched PEG-aldehyde the 20 kDA PEG-aldehyde comprising two 10 kDA linear PEG molecules (e.g., Sunbright® GL2-200AL3, NOF), a 20 kDa 2-arm branched PEG-NHS ester the 20 kDA PEG-NETS ester comprising two 10 kDA linear PEG molecules (e.g., Sunbright® GL2-200TS, Sunbright® GL200GS2, NOF), a 40 kDa 2-arm branched PEG-aldehyde the 40 kDA PEG-aldehyde comprising two 20 kDA linear PEG molecules (e.g., Sunbright® GL2-400AL3), a 40 kDa 2-arm branched PEG-NETS ester the 40 kDA PEG-NETS ester comprising two 20 kDA linear PEG molecules (e.g., Sunbright® GL2-400AL3, Sunbright® GL2-400GS2, NOF), a linear 30 kDa PEG-aldehyde (e.g., Sunbright® ME-300AL) and a linear 30 kDa PEG-NETS ester.

Fc Fusions

In some embodiments, the carrier molecule is a Fc molecule or a monomeric subunit thereof. In some embodiments, the dimeric Fc molecule may be engineered to possess a "knob-into-hole modification." The knob-into-hole modification is more fully described in Ridgway, et al. (1996) Protein Engineering 9(7):617-621 and U.S. Pat. No. 5,731,168, issued Mar. 24, 1998, U.S. Pat. No. 7,642,228, issued Jan. 5, 2010, U.S. Pat. No. 7,695,936, issued Apr. 13, 2010, and U.S. Pat. No. 8,216,805, issued Jul. 10, 2012. The knob-into-hole modification refers to a modification at the interface between two immunoglobulin heavy chains in the CH3 domain, wherein: i) in a CH3 domain of a first heavy chain, an amino acid residue is replaced with an amino acid residue having a larger side chain (e.g., tyrosine or tryptophan) creating a projection from the surface ("knob") and ii) in the CH3 domain of a second heavy chain, an amino acid residue is replaced with an amino acid residue having a smaller side chain (e.g., alanine or threonine), thereby generating a cavity ("hole") within at interface in the second CH3 domain within which the protruding side chain of the first CH3 domain ("knob") is received by the cavity in the second CH3 domain. In one embodiment, the "knob-into-hole modification" comprises the amino acid substitution T366W and optionally the amino acid substitution S354C in one of the antibody heavy chains, and the amino acid substitutions T366S, L368A, Y407V and optionally Y349C in the other one of the antibody heavy chains. Furthermore, the Fc domains may be modified by the introduction of cysteine residues at positions S354 and Y349 which results in a stabilizing disulfide bridge between the two antibody heavy chains in the Fe region (Carter, et al. (2001) Immunol Methods 248, 7-15). The knob-into-hole format is used to facilitate the expression of a first polypeptide (e.g., an IL12RB1 binding sdAb) on a first Fc monomer with a "knob" modification and a second polypeptide on the second Fc monomer possessing a "hole" modification to facilitate the expression of heterodimeric polypeptide conjugates.

Targeting Domains

In some embodiments, the IL12Rb1 binding molecule is provided as a component of a multivalent (e.g., bivalent) fusion protein with a polypeptide sequence ("targeting domain") to facilitate selective binding to particular cell type or tissue expressing a cell surface molecule that specifically binds to such targeting domain, optionally incorporating a linker between the IL12RB1 binding sdAb sequence and the sequence of the targeting domain of the fusion protein.

In some embodiments of the IL12Rb1 binding molecule is operably linked to a targeting domain As used herein, the term targeting domain refers to a moiety that specifically binds to a molecule expressed on the surface of a target cell. The targeting domain may be any moiety that specifically binds to one or more cell surface molecules (e.g., T cell receptor) expressed on the surface of a target cell. In some embodiments, the target cell is a T cell. In some embodiments, the target cell is a IL12Rb1+ T cell.

In some embodiments, the targeting domain is a ligand for a receptor. In some embodiments, the targeting domain is a ligand for a receptor expressed on the surface of a T cell. In some embodiments, the ligand is a cytokine. In some embodiments, the cytokine includes but is not limited to the group consisting interleukins, interferons, and functional derivatives thereof. In some embodiments, the cytokine includes but is not limited to the group consisting IL2, IL3, IL4, IL7, IL9, IL12, IL15, IL18, IL21, IL22, IL23, IL27, IL28, IL34, and modified versions or fragments thereof that bind to their cognate ligand expressed on the surface of a T-cell. In some embodiments, the cytokine includes but is not limited to the group consisting of interferon alpha, interferon a2b, interferon gamma, or interferon lambda and modified versions or fragments thereof that bind to their cognate ligand expressed on the surface of a T-cell.

In another aspect, the present disclosure provides a multivalent binding molecule, the multivalent binding molecule comprising: (a) a IL12RB1 binding molecule and (b) a second binding molecule that specifically binds to the extracellular domain of a second cell surface molecule, wherein the IL12RB1 binding molecule and second binding molecule are operably linked, optionally through a chemical or polypeptide linker. In some embodiments, the IL12RB1 binding molecules of the present disclosure are useful in the preparation of the multivalent binding molecules described in Gonzalez, et al. PCT/US2018/021301 published as WO 2018/182935 A1 on Oct. 4, 2018. In accordance with the teaching of Gonzalez, the second binding molecule specifically binds to the extracellular domain of: (i) a component of cytokine receptor other than a receptor of which IL12Rb1 forms a signaling complex in response to a natural ligand (e.g. IL12Rb2) that activates the JAK/STAT pathway in the cell; (ii) a receptor tyrosine kinase; or (iii) a TNFR superfamily member. In some embodiments, the second surface molecule is a tyrosine kinase selected from EGFR, ErbB2, ErbB3, ErbB4, InsR, IGF1R, InsRR, PDGFRα, PDGFRβ, CSF1R/Fms, cKit, Flt-3/Flk2, VEGFR1, VEGFR2, VEGFR3, FGFR1, FGFR2, FGFR3, FGFR4, PTK7/CCK4, TrkA, TrkB, TrkC, Ror1, Ror2, MuSK, Met, Ron, Axl, Mer, Tyro3, Tie1, Tie2, EphA1-8, EphA10, EphB1-4, EphB6, Ret, Ryk, DDR1, DDR2, Ros, LMR1, LMR2, LMR3, ALK, LTK, SuRTK106/STYK1. In some embodiments, the second surface molecule is a TNFR superfamily member is selected from TNFR1 (TNFRSF1A), TNFR2 (TNFRSF1B; TNFRSF2), 41-BB (TNFRSF9); AITR (TNFRSF18); BCMA (TNFRSF17), CD27 (TNFRSF7), CD30 (TNFRSF8), CD40 (TNFRSF5), Death Receptor 1 (TNFRSF10C), Death Receptor-3 (TNFRSF25), Death Receptor 4 (TNFRSF10A), Death Receptor 5 (TNFRSF10B), Death Receptor-6 (TNFRSF21), Decoy Receptor-3 (TNFRSF6B), Decoy Receptor 2 (TNFRSF10D), EDAR, Fas (TNFRSF6), HVEM (TNFRSF14), LTBR (TNFRSF3), OX40 (TNFRSF4), RANK (TNFRSF11A), TACI (TNFRSF13B), Troy (TNFRSF19), XEDAR (TNFRSF27), Osteoprotegerin (TNFRSF11B), TWEAK receptor (TNFRSF12A), BAFF Receptor (TNFRSF13C), NGF receptor (TNFRSF16).

In some embodiments, the targeting domain of the IL12Rb1 binding molecule is an antibody (as defined hereinabove to include molecules such as VHHs, scFvs, etc.) Examples of antibodies that may incorporated as a targeting domain of a IL12Rb1 binding molecule include but are not limited to the group consisting of: anti-GD2 antibodies, anti-BCMA antibodies, anti-CD19 antibodies, anti-CD33 antibodies, anti-CD38 antibodies, anti-CD70 antibodies, anti-GD2 antibodies and IL3Ra2 antibodies, anti-CD19 antibodies, anti-mesothelin antibodies, anti-Her2 antibodies, anti-EpCam antibodies, anti-Muc1 antibodies, anti-ROR1 antibodies, anti-CD133 antibodies, anti-CEA antibodies, anti-PSMA antibodies, anti-EGRFRVIII antibodies, anti-PSCA antibodies, anti-GPC3 antibodies, anti-Pan-ErbB antibodies, and anti-FAP antibodies.

The antibody or antigen-binding fragment thereof can also be linked to another antibody to form, e.g., a bispecific or a multispecific antibody Labels In some embodiments, the IL binding molecule is operably linked to label. In some embodiments, the label is incorporated to facilitate use as imaging agent, diagnostic agent, or for use in cell sorting procedures. The term labels includes but is not limited to fluorescent labels, a biologically active enzyme labels, a radioisotopes (e.g., a radioactive ions), a nuclear magnetic resonance active labels, a luminescent labels, or a magnetic compound. In one embodiment a IL binding sdAb (e.g., a IL binding VHH) molecule in stable association (e.g., covalent, coordinate covalent) with an imaging labels. The term imaging labels is used to describe any of a variety of compounds a signature that facilitates identification, tracing and/or localization of the IL12RB1 binding sdAb (or its metabolites) using diagnostic procedures. Examples of imaging labels include, but are not limited to, fluorescent compounds, radioactive compounds, and compounds opaque to imaging methods (e.g., X-ray, ultrasound). Examples of radioactive compounds useful as imaging label include but are not limited to Technetium-99m ($^{99m}$Tc), Indium-111 ($^{111}$In), Iodine-131 ($^{131}$I), Iodine-123 ($^{123}$I), Iodine-125 ($^{125}$I) Gallium-67 ($^{67}$Ga), and Lutetium-177 ($^{177}$Lu), phosphorus ($^{32}$P), carbon ($^{14}$C), tritium ($^{3}$H), yttrium ($^{90}$Y), actinium ($^{225}$Ac), astatine ($^{211}$At), rhenium ($^{186}$Re), bismuth ($^{212}$Bi or $^{213}$Bi), and rhodium ($^{188}$Rh).

Therapeutic Agents

In some embodiments, the IL12RB1 binding molecule is operably linked to a therapeutic agent. Examples of therapeutic agents include therapeutic small molecule (e.g., chemotherapeutic agents) or biologic therapeutic agents including antibodies, cytoxic or cytostatic compounds, a radioisotope, molecules of plant, fungal, or bacterial origin, or biological proteins (e.g., protein toxins) or particles (e.g., nano-particles or recombinant viral particles, e.g., via a viral coat protein), therapeutic antibodies, chemotherapeutic agents, as described more fully herein.

In some embodiments, the therapeutic agent which may be incorporated into the IL12Rb1 binding molecules of the present disclosure is short-range radiation emitters, including, for example, short-range, high-energy a-emitters. Examples of such radioisotope include an alpha-emitter, a beta-emitter, a gamma-emitter or a beta/gamma emitter. Radioisotopes useful as therapeutic agents include yttrium 90 ($^{90}$Y), lutetium-177 ($^{177}$Lu), actinium-225 ($^{225}$Ac), astatine-211 ($^{211}$At), rhenium-186 ($^{186}$Re), bismuth-212 ($^{212}$Bi), bismuth-213 ($^{213}$Bi), and rhodium-188 ($^{188}$Rh).

In some embodiments, the IL12Rb1 binding molecule is operably linked a cytotoxic agent (or derivative thereof), such maytansinol or the DM1 maytansinoid), a taxane, or a calicheamicin, pseudomonas exotoxin A, deBouganin, ricin toxin, diphtheria toxin, an amatoxin, such as a-amanitin, saporin, maytansine, a maytansinoid, an auristatin, an anthracycline, a calicheamicin, irinotecan, SN-38, a duocarmycin, a pyrrolobenzodiazepine, a pyrrolobenzodiazepine dimer, an indolinobenzodiazepine, and an indolinobenzodiazepine dimer, or a variant thereof).

Synthesis of IL12Rb1 Binding Molecules:

In some embodiments, the IL12Rb1 binding molecules of the present disclosure are polypeptides. However, in some embodiments, only a portion of the IL12Rb1 binding molecule is a polypeptide, for example where the IL12Rb1 binding molecule comprises a non-peptidyl domain (e.g., a PEG IL12RB1 binding sdAb conjugate, a radionucleotide IL12RB1 binding sdAb conjugate, or a small molecule IL12RB1 binding sdAb conjugate). The following provides guidance to enable the solid phase and recombinant synthesis of the polypeptide portions (domains) of IL12Rb1 binding molecules of the present disclosure. In those embodiments where only a portion of the IL12Rb1 binding molecule is a polypeptide, it will be understood that the peptidyl domain(s) of the IL12Rb1 binding molecule are an intermediate in the process which may undergo further processing to complete the synthesis of the desired IL12Rb1 binding molecules. The polypeptide domains of IL12Rb1 binding molecules may be produced by conventional methodology for the construction of polypeptides including recombinant or solid phase syntheses as described in more detail below.

Chemical Synthesis

In addition to generating mutant polypeptides via expression of nucleic acid molecules that have been altered by recombinant molecular biological techniques, polypeptide domains of IL12Rb1 binding molecules can be chemically synthesized. Chemically synthesized polypeptides are routinely generated by those of skill in the art. Chemical synthesis includes direct synthesis of a peptide by chemical means of the polypeptide domains of IL12Rb1 binding molecules exhibiting the properties described. This method can incorporate both natural and unnatural amino acids at desired positions that facilitate linkage of particular molecules (e.g., PEG).

In some embodiments, the polypeptide domains of IL12Rb1 binding molecules of the present disclosure may be prepared by chemical synthesis. The chemical synthesis of the polypeptide domains of IL12Rb1 binding molecules may proceed via liquid-phase or solid-phase. Solid-phase peptide synthesis (SPPS) allows the incorporation of unnatural amino acids and/or peptide/protein backbone modification. Various forms of SPPS are available for synthesizing the polypeptide domains of IL12Rb1 binding molecules of the present disclosure are known in the art (e.g., Ganesan A. (2006) Mini Rev. Med. Chem. 6:3-10; and Camarero J. A. et al., (2005) Protein Pept Lett. 12:723-8). In the course of chemical synthesis, the alpha functions and any reactive side chains may protected with acid-labile or base-labile groups that are stable under the conditions for linking amide bonds but can readily be cleaved without impairing the peptide chain that has formed.

In the solid phase synthesis, either the N-terminal or C-terminal amino acid may be coupled to a suitable support material. Suitable support materials are those which are inert towards the reagents and reaction conditions for the stepwise condensation and cleavage reactions of the synthesis process and which do not dissolve in the reaction media being used. Examples of commercially available support materials include styrene/divinylbenzene copolymers which have been modified with reactive groups and/or polyethylene glycol; chloromethylated styrene/divinylbenzene copolymers; hydroxymethylated or aminomethylated styrene/divinylbenzene copolymers; and the like. The successive coupling of the protected amino acids can be carried out according to conventional methods in peptide synthesis, typically in an automated peptide synthesizer.

At the end of the solid phase synthesis, the peptide is cleaved from the support material while simultaneously cleaving the side chain protecting groups. The peptide obtained can be purified by various chromatographic methods including but not limited to hydrophobic adsorption chromatography, ion exchange chromatography, distribution chromatography, high pressure liquid chromatography (HPLC) and reversed-phase HPLC.

Recombinant Production

Alternatively, polypeptide domains of IL12Rb1 binding molecules of the present disclosure may be produced by recombinant DNA technology. In the typical practice of recombinant production of polypeptides, a nucleic acid sequence encoding the desired polypeptide is incorporated into an expression vector suitable for the host cell in which expression will be accomplish, the nucleic acid sequence being operably linked to one or more expression control sequences encoding by the vector and functional in the target host cell. The recombinant protein may be recovered through disruption of the host cell or from the cell medium if a secretion leader sequence (signal peptide) is incorporated into the polypeptide. The recombinant protein may be purified and concentrated for further use including incorporation.

Synthesis of Nucleic Acid Sequences Encoding the IL12Rb1 Binding Molecule

In some embodiments, the polypeptide domains of IL12Rb1 binding molecule is produced by recombinant methods using a nucleic acid sequence encoding the polypeptide domains of IL12Rb1 binding molecule (or fusion protein comprising the polypeptide domains of IL12Rb1 binding molecule). The nucleic acid sequence encoding the desired polypeptide domains of IL12Rb1 binding molecule can be synthesized by chemical means using an oligonucleotide synthesizer.

The nucleic acid molecules are not limited to sequences that encode polypeptides; some or all of the non-coding sequences that lie upstream or downstream from a coding sequence (e.g., the coding sequence of the polypeptide domains of IL12Rb1 binding molecule) can also be included. Those of ordinary skill in the art of molecular biology are familiar with routine procedures for isolating nucleic acid molecules. They can, for example, be generated by treatment of genomic DNA with restriction endonucleases, or by performance of the polymerase chain reaction (PCR). In the event the nucleic acid molecule is a ribonucleic acid (RNA), molecules can be produced, for example, by in vitro transcription.

The nucleic acid molecules encoding the polypeptide domains of IL12Rb1 binding molecule (and fusions thereof) may contain naturally occurring sequences or sequences that differ from those that occur naturally, but, due to the degeneracy of the genetic code, encode the same polypeptide. These nucleic acid molecules can consist of RNA or DNA (for example, genomic DNA, cDNA, or synthetic DNA, such as that produced by phosphoramidite-based synthesis), or combinations or modifications of the nucleotides within these types of nucleic acids. In addition, the nucleic acid molecules can be double-stranded or single-stranded (i.e., either a sense or an antisense strand).

Nucleic acid sequences encoding the polypeptide domains of the IL12Rb1 binding molecule may be obtained from various commercial sources that provide custom synthesis of nucleic acid sequences. Amino acid sequence variants of the HUMAN IL12Rb1 binding molecules of the present disclosure are prepared by introducing appropriate nucleotide changes into the coding sequence based on the genetic code which is well known in the art. Such variants represent insertions, substitutions, and/or specified deletions of, residues as noted. Any combination of insertion, substitution, and/or specified deletion can be made to arrive at the final construct, provided that the final construct possesses the desired biological activity as defined herein.

Methods for constructing a DNA sequence encoding the polypeptide domains of IL12Rb1 binding molecule and expressing those sequences in a suitably transformed host include, but are not limited to, using a PCR-assisted mutagenesis technique. Mutations that consist of deletions or additions of amino acid residues to polypeptide domains of IL12Rb1 binding molecule can also be made with standard recombinant techniques. In the event of a deletion or addition, the nucleic acid molecule encoding polypeptide domains of IL12Rb1 binding molecule is optionally digested with an appropriate restriction endonuclease. The resulting fragment can either be expressed directly or manipulated further by, for example, ligating it to a second fragment. The ligation may be facilitated if the two ends of the nucleic acid molecules contain complementary nucleotides that overlap one another, but blunt-ended fragments can also be ligated. PCR-generated nucleic acids can also be used to generate various mutant sequences.

A polypeptide domain of IL12Rb1 binding molecules of the present disclosure may be produced recombinantly not only directly, but also as a fusion polypeptide with a heterologous polypeptide, e.g., a signal sequence or other polypeptide having a specific cleavage site at the N-terminus or C-terminus of the mature IL12Rb1 binding molecule. In general, the signal sequence may be a component of the vector, or it may be a part of the coding sequence that is inserted into the vector. The heterologous signal sequence selected preferably is one that is recognized and processed (i.e., cleaved by a signal peptidase) by the host cell. In some embodiments, the signal sequence is the signal sequence that is natively associated with the IL12Rb1 binding molecule (i.e. the human IL12Rb1 signal sequence). The inclusion of a signal sequence depends on whether it is desired to secrete the IL12Rb1 binding molecule from the recombinant cells in which it is made. If the chosen cells are prokaryotic, it generally is preferred that the DNA sequence not encode a signal sequence. If the chosen cells are eukaryotic, it generally is preferred that a signal sequence be encoded and most preferably that the wild type IL-2 signal sequence be used. Alternatively, heterologous mammalian signal sequences may be suitable, such as signal sequences from secreted polypeptides of the same or related species, as well as viral secretory leaders, for example, the herpes simplex gD signal. When the recombinant host cell is a yeast cell such as *Saccharomyces cerevisiae*, the alpha mating factor secretion signal sequence may be employed to achieve extracellular secretion of the IL12Rb1 binding molecule into the culture medium as described in Singh, U.S. Pat. No. 7,198,919 B1.

In the event the polypeptide domain of IL12Rb1 binding molecules to be expressed is to be expressed as a chimera (e.g., a fusion protein comprising a IL12Rb1 binding molecule and a heterologous polypeptide sequence), the chimeric protein can be encoded by a hybrid nucleic acid molecule comprising a first sequence that encodes all or part of the polypeptide domains of IL12Rb1 binding molecule and a second sequence that encodes all or part of the heterologous polypeptide. For example, polypeptide domains of IL12Rb1 binding molecules described herein may be fused to a hexa-histidine tag (SEQ ID NO: 230) to facilitate purification of bacterially expressed protein, or to a hemagglutinin tag to facilitate purification of protein expressed in eukaryotic cells. By first and second, it should not be understood as limiting to the orientation of the elements of the fusion protein and a heterologous polypeptide can be linked at either the N-terminus and/or C-terminus of the polypeptide domains of IL12Rb1 binding molecule. For example, the N-terminus may be linked to a targeting domain and the C-terminus linked to a hexa-histidine tag (SEQ ID NO: 230) purification handle.

The complete amino acid sequence of the polypeptide domain of IL12Rb1 binding molecule (or fusion/chimera) to be expressed can be used to construct a back-translated gene. A DNA oligomer containing a nucleotide sequence coding for the polypeptide domain of IL12Rb1 binding molecules can be synthesized. For example, several small oligonucleotides coding for portions of the desired polypeptide can be synthesized and then ligated. The individual oligonucleotides typically contain 5' or 3' overhangs for complementary assembly.

In some embodiments, the nucleic acid sequence encoding the polypeptide domain of the IL12Rb1 binding molecule may be "codon optimized" to facilitate expression in a particular host cell type. Techniques for codon optimization in a wide variety of expression systems, including mammalian, yeast and bacterial host cells, are well known in the and there are online tools to provide for a codon optimized sequences for expression in a variety of host cell types. See e.g., Hawash, et al., (2017) 9:46-53 and Mauro and Chappell in *Recombinant Protein Expression in Mammalian Cells: Methods and Protocols*, edited by David Hacker (Human Press New York). Additionally, there are a variety of web based on-line software packages that are freely available to assist in the preparation of codon optimized nucleic acid sequences.

Expression Vectors

Once assembled (by synthesis, site-directed mutagenesis or another method), the nucleic acid sequence encoding polypeptide domains of IL12Rb1 binding molecule will be inserted into an expression vector. A variety of expression vectors for uses in various host cells are available and are typically selected based on the host cell for expression. An expression vector typically includes, but is not limited to, one or more of the following: an origin of replication, one or more marker genes, an enhancer element, a promoter, and a transcription termination sequence. Vectors include viral vectors, plasmid vectors, integrating vectors, and the like. Plasmids are examples of non-viral vectors. To facilitate efficient expression of the recombinant polypeptide, the nucleic acid sequence encoding the polypeptide sequence to be expressed is operably linked to transcriptional and translational regulatory control sequences that are functional in the chosen expression host.

Expression vectors typically contain a selection gene, also termed a selectable marker. This gene encodes a protein necessary for the survival or growth of transformed host cells grown in a selective culture medium. Host cells not transformed with the vector containing the selection gene will not survive in the culture medium. Typical selection genes encode proteins that (a) confer resistance to antibiotics or other toxins, e.g., ampicillin, neomycin, methotrexate, or tetracycline, (b) complement auxotrophic deficiencies, or (c) supply critical nutrients not available from complex media.

Expression vectors for polypeptide domain of IL12Rb1 binding molecules of the present disclosure contain a regulatory sequence that is recognized by the host organism and is operably linked to nucleic acid sequence encoding the polypeptide domains of IL12Rb1 binding molecule. The terms "regulatory control sequence," "regulatory sequence" or "expression control sequence" are used interchangeably herein to refer to promoters, enhancers, and other expression control elements (e.g., polyadenylation signals). See, for example, Goeddel (1990) in Gene Expression Technology: Methods in Enzymology 185 (Academic Press, San Diego CA USA Regulatory sequences include those that direct constitute expression of a nucleotide sequence in many types of host cells and those that direct expression of the nucleotide sequence only in certain host cells (e.g., tissue-specific regulatory sequences). It will be appreciated by those skilled in the art that the design of the expression vector can depend on such factors as the choice of the host cell to be transformed, the level of expression of protein desired, and the like. In selecting an expression control sequence, a variety of factors understood by one of skill in the art are to be considered. These include, for example, the relative strength of the sequence, its controllability, and its compatibility with the actual DNA sequence encoding the subject IL12Rb1 binding molecule, particularly as regards potential secondary structures.

In some embodiments, the regulatory sequence is a promoter, which is selected based on, for example, the cell type in which expression is sought. Promoters are untranslated sequences located upstream (5') to the start codon of a structural gene (generally within about 100 to 1000 bp) that control the transcription and translation of particular nucleic acid sequence to which they are operably linked. Such promoters typically fall into two classes, inducible and constitutive. Inducible promoters are promoters that initiate increased levels of transcription from DNA under their control in response to some change in culture conditions, e.g., the presence or absence of a nutrient or a change in temperature. A large number of promoters recognized by a variety of potential host cells are well known.

A T7 promoter can be used in bacteria, a polyhedrin promoter can be used in insect cells, and a cytomegalovirus or metallothionein promoter can be used in mammalian cells. Also, in the case of higher eukaryotes, tissue-specific and cell type-specific promoters are widely available. These promoters are so named for their ability to direct expression of a nucleic acid molecule in a given tissue or cell type within the body. Skilled artisans are well aware of numerous promoters and other regulatory elements which can be used to direct expression of nucleic acids.

Transcription from vectors in mammalian host cells may be controlled, for example, by promoters obtained from the genomes of viruses such as polyoma virus, fowlpox virus, adenovirus (such as human adenovirus serotype 5), bovine papilloma virus, avian sarcoma virus, cytomegalovirus, a retrovirus (such as murine stem cell virus), hepatitis-B virus and most preferably Simian Virus 40 (SV40), from heterologous mammalian promoters, e.g., the actin promoter, PGK (phosphoglycerate kinase), or an immunoglobulin promoter, from heat-shock promoters, provided such promoters are compatible with the host cell systems. The early and late promoters of the SV40 virus are conveniently obtained as an SV40 restriction fragment that also contains the SV40 viral origin of replication.

Transcription by higher eukaryotes is often increased by inserting an enhancer sequence into the vector. Enhancers are cis-acting elements of DNA, usually about from 10 to 300 bp, which act on a promoter to increase its transcription. Enhancers are relatively orientation and position independent, having been found 5' and 3' to the transcription unit, within an intron, as well as within the coding sequence itself. Many enhancer sequences are now known from mammalian genes (globin, elastase, albumin, alpha-fetoprotein, and insulin). Typically, however, one will use an enhancer from a eukaryotic cell virus. Examples include the SV40 enhancer on the late side of the replication origin, the cytomegalovirus early promoter enhancer, the polyoma enhancer on the late side of the replication origin, and adenovirus enhancers. The enhancer may be spliced into the expression vector at a position 5' or 3' to the coding sequence but is preferably located at a site 5' from the promoter. Expression vectors used in eukaryotic host cells will also contain sequences necessary for the termination of transcription and for stabilizing the mRNA. Such sequences are commonly available from the 5' and, occasionally 3', untranslated regions of eukaryotic or viral DNAs or cDNAs. Construction of suitable vectors containing one or more of the above-listed components employs standard techniques.

In addition to sequences that facilitate transcription of the inserted nucleic acid molecule, vectors can contain origins of replication, and other genes that encode a selectable marker. For example, the neomycin-resistance (neoR) gene imparts G418 resistance to cells in which it is expressed, and thus permits phenotypic selection of the transfected cells. Additional examples of marker or reporter genes include beta-lactamase, chloramphenicol acetyltransferase (CAT), adenosine deaminase (ADA), dihydrofolate reductase (DHFR), hygromycin-B-phosphotransferase (HPH), thymidine kinase (TK), lacZ (encoding beta-galactosidase), and xanthine guanine phosphoribosyltransferase (XGPRT). Those of skill in the art can readily determine whether a given regulatory element or selectable marker is suitable for use in a particular experimental context. Proper assembly of the expression vector can be confirmed by nucleotide sequencing, restriction mapping, and expression of a biologically active polypeptide in a suitable host.

Host Cells

The present disclosure further provides prokaryotic or eukaryotic cells that contain and express a nucleic acid molecule that encodes a polypeptide domains of IL12Rb1 binding molecule. A cell of the present disclosure is a transfected cell, i.e., a cell into which a nucleic acid molecule, for example a nucleic acid molecule encoding a polypeptide domains of IL12Rb1 binding molecule, has been introduced by means of recombinant DNA techniques. The progeny of such a cell are also considered within the scope of the present disclosure.

Host cells are typically selected in accordance with their compatibility with the chosen expression vector, the toxicity of the product coded for by the DNA sequences of this IL12Rb1 binding molecule, their secretion characteristics, their ability to fold the polypeptides correctly, their fermentation or culture requirements, and the ease of purification of the products coded for by the DNA sequences. Suitable host cells for cloning or expressing the DNA in the vectors herein are the prokaryote, yeast, or higher eukaryote cells.

In some embodiments the recombinant polypeptide domains of IL12Rb1 binding molecule or biologically active variants thereof can also be made in eukaryotes, such as yeast or human cells. Suitable eukaryotic host cells include insect cells (examples of Baculovirus vectors available for expression of proteins in cultured insect cells (e.g., 519 cells) include the pAc series (Smith et al. (1983) Mol. Cell Biol. 3:2156-2165) and the pVL series (Lucklow and Summers (1989) Virology 170:31-39)); yeast cells (examples of vectors for expression in yeast *S. cerevisiae* include pYepSecl (Baldari et al. (1987) EMBO J. 6:229-234), pMFa (Kurjan and Herskowitz (1982) Cell 30:933-943), pJRY88 (Schultz et al. (1987) Gene 54:113-123), pYES2 (Invitrogen Corporation, San Diego, Calif.), and pPicZ (Invitrogen Corporation, San Diego, Calif.)); or mammalian cells (mammalian expression vectors include pCDM8 (Seed (1987) Nature 329:840) and pMT2PC (Kaufman et al. (1987) EMBO J. 6:187:195)).

Examples of useful mammalian host cell lines are mouse L cells (L-M[TK-], ATCC #CRL-2648), monkey kidney CV1 line transformed by SV40 (COS-7, ATCC CRL 1651); human embryonic kidney line (HEK293 or HEK293 cells subcloned for growth in suspension culture; baby hamster kidney cells (BHK, ATCC CCL 10); Chinese hamster ovary cells/-DHFR (CHO); mouse sertoli cells (TM4); monkey kidney cells (CV1 ATCC CCL 70); African green monkey kidney cells (VERO-76, ATCC CRL-1 587); human cervical carcinoma cells (HELA, ATCC CCL 2); canine kidney cells (MDCK, ATCC CCL 34); buffalo rat liver cells (BRL 3A, ATCC CRL 1442); human lung cells (W138, ATCC CCL 75); human liver cells (Hep G2, HB 8065); mouse mammary tumor (MMT 060562, ATCC CCL51); TRI cells; MRC 5 cells; FS4 cells; and a human hepatoma line (Hep G2). In mammalian cells, the expression vector's control functions are often provided by viral regulatory elements. For example, commonly used promoters are derived from polyoma, Adenovirus 2, cytomegalovirus, and Simian Virus 40.

The polypeptide domains of IL12Rb1 binding molecule can be produced in a prokaryotic host, such as the bacterium *E. coli*, or in a eukaryotic host, such as an insect cell (e.g., an Sf21 cell), or mammalian cells (e.g., COS cells, NIH 3T3 cells, or HeLa cells). These cells are available from many sources, including the American Type Culture Collection (Manassas, Va.). Artisans or ordinary skill are able to make such a determination. Furthermore, if guidance is required in selecting an expression system, skilled artisans may consult Ausubel et al. (Current Protocols in Molecular Biology, John Wiley and Sons, New York, N.Y., 1993) and Pouwels et al. (Cloning Vectors: A Laboratory Manual, 1985 Suppl. 1987).

In some embodiments, the recombinant polypeptide domains of IL12Rb1 binding molecule may be glycosylated or unglycosylated depending on the host organism used to produce the IL12Rb1 binding molecule. If bacteria are chosen as the host then the polypeptide domains of IL12Rb1 binding molecule produced will be aglycosylated. Eukaryotic cells, on the other hand, will glycosylate the recombinant polypeptide domains of IL12Rb1 binding molecule.

For other additional expression systems for both prokaryotic and eukaryotic cells, see Chapters 16 and 17 of Sambrook et al. (1989) Molecular Cloning: A Laboratory Manual (2nd ed., Cold Spring Harbor Laboratory Press, Plainview, N.Y.). See, Goeddel (1990) in Gene Expression Technology: Methods in Enzymology 185 (Academic Press, San Diego, Calif.).

Transfection

The expression constructs of the can be introduced into host cells to thereby produce the recombinant polypeptide domains of IL12Rb1 binding molecule disclosed herein or to produce biologically active muteins thereof. Vector DNA can be introduced into prokaryotic or eukaryotic cells via conventional transformation or transfection techniques. Suitable methods for transforming or transfecting host cells can be found in Sambrook et al. (1989) Molecular Cloning: A Laboratory Manual (2d ed., Cold Spring Harbor Laboratory Press, Plainview, N.Y.) and other standard molecular biology laboratory manuals.

In order to facilitate transfection of the target cells, the target cell may be exposed directly with the non-viral vector may under conditions that facilitate uptake of the non-viral vector. Examples of conditions which facilitate uptake of foreign nucleic acid by mammalian cells are well known in the art and include but are not limited to chemical means (such as Lipofectamine®, Thermo-Fisher Scientific), high salt, and magnetic fields (electroporation).

Cell Culture

Cells may be cultured in conventional nutrient media modified as appropriate for inducing promoters, selecting transformants, or amplifying the genes encoding the desired sequences. Mammalian host cells may be cultured in a variety of media. Commercially available media such as Ham's F10 (Sigma), Minimal Essential Medium ((MEM), Sigma), RPMI 1640 (Sigma), and Dulbecco's Modified Eagle's Medium ((DMEM), Sigma) are suitable for culturing the host cells. Any of these media may be supplemented as necessary with hormones and/or other growth factors (such as insulin, transferrin, or epidermal growth factor), salts (such as sodium chloride, calcium, magnesium, and phosphate), buffers (such as HEPES), nucleosides (such as adenosine and thymidine), antibiotics, trace elements, and glucose or an equivalent energy source. Any other necessary supplements may also be included at appropriate concentrations that would be known to those skilled in the art. The culture conditions, such as temperature, pH and the like, are those previously used with the host cell selected for expression and will be apparent to the ordinarily skilled artisan.

Recovery of Recombinant Proteins

Recombinantly-produced IL12Rb1 binding polypeptides can be recovered from the culture medium as a secreted polypeptide if a secretion leader sequence is employed. Alternatively, the IL12Rb1 binding polypeptides can also be recovered from host cell lysates. A protease inhibitor, such as phenyl methyl sulfonyl fluoride (PMSF) may be employed during the recovery phase from cell lysates to inhibit proteolytic degradation during purification, and antibiotics may be included to prevent the growth of adventitious contaminants.

Purification

Various purification steps are known in the art and find use, e.g., affinity chromatography. Affinity chromatography makes use of the highly specific binding sites usually present in biological macromolecules, separating molecules on their ability to bind a particular ligand. Covalent bonds attach the ligand to an insoluble, porous support medium in a manner that overtly presents the ligand to the protein sample, thereby using natural specific binding of one molecular species to separate and purify a second species from a mixture. Antibodies are commonly used in affinity chromatography. Size selection steps may also be used, e.g., gel filtration chromatography (also known as size-exclusion chromatography or molecular sieve chromatography) is used to separate proteins according to their size. In gel filtration, a protein solution is passed through a column that is packed with semipermeable porous resin. The semipermeable resin has a range of pore sizes that determines the size of proteins that can be separated with the column. In some embodiments, the His-Tag modified protein is purified by immobilized metal affinity chromatography (IMAC), the His-Tag being optionally removed following purification.

The recombinant polypeptide domains of IL12Rb1 binding molecule produced by the transformed host can be purified according to any suitable method. IL12Rb1 binding molecules can be isolated from inclusion bodies generated in *E. coli*, or from conditioned medium from either mammalian or yeast cultures producing a given IL12Rb1 binding molecule sing cation exchange, gel filtration, and or reverse phase liquid chromatography.

The substantially purified forms of the recombinant polypeptides can be used, e.g., as therapeutic agents, as described herein.

The biological activity of the recombinant polypeptide domains of IL12Rb1 binding molecule produced in accordance with the foregoing can be confirmed by a IL12Rb1 binding using procedures well known in the art including but not limited to competition ELISA, radioactive ligand binding assays (e.g., saturation binding, Scatchard plot, nonlinear curve fitting programs and competition binding assays); non-radioactive ligand binding assays (e.g., fluorescence polarization (FP), fluorescence resonance energy transfer (FRET) and surface plasmon resonance assays (see, e.g., Drescher et al., Methods Mol Biol 493:323-343 (2009) with instrumentation commercially available from GE Healthcare Bio-Sciences such as the Biacore 8+, Biacore S200, Biacore T200 (GE Healthcare Bio-Sciences, 100 Results Way, Marlborough MA 01752)); liquid phase ligand binding assays (e.g., real-time polymerase chain reaction (RT-qPCR), and immunoprecipitation); and solid phase ligand binding assays (e.g., multiwell plate assays, on-bead ligand binding assays, on-column ligand binding assays, and filter assays).

Methods of Use

Inhibition of IL12Rb1 Receptor Activity

In one embodiment, the present disclosure provides a method of modulating the activity of cells expressing the IL12Rb1 by the administration of a IL12Rb1 binding molecule to a subject in an amount sufficient to interfere with the activity of receptors comprising the of IL12Rb1. The present disclosure further provides a method of modulating the activity of cells expressing the IL12Rb1 in a mixed population of cells comprising contacting said population of cells, in vivo and/or ex vivo, with a IL12Rb1 binding molecule or complex of the present disclosure to in an amount sufficient to interfere with the activity of receptors comprising the IL12Rb1.

Identification Isolation, Enrichment or Depletion of IL12Rb1+ Cells

In one embodiment, the present disclosure provides a method of use of the IL12Rb1 binding molecules of the present disclosure useful in a process for in the isolation, enrichment or depletion of IL12Rb1+ cells from a biological sample comprising IL12Rb1+ cells. The biological sample may comprise cells of blood origin such as PBMC, T cells, B cells of cell culture origin or of tissue origin such as brain or bone marrow. Processes suitable for the isolation, enrichment or depletion of IL12Rb1+ cells comprise centrifugation, filtration, magnetic cell sorting and fluorescent cell sorting by techniques well known in the art. The present disclosure further provides a method for the treatment of a subject suffering from a disease, disorder or condition by the administration of a therapeutically effective amount of a cell product enriched or depleted of IL12Rb1+ cells through the use of a IL12Rb1 binding molecule as described herein.

In one embodiment, the sorting procedure employs a IL12Rb1 binding molecule comprising a fluorescent label for use in FACS isolation or depletion of IL12Rb1+ cells from a sample. The fluorescent label may be attached to the sdAb of the IL12Rb1 binding molecule directly (e.g., by chemical conjugation optionally employing a linker) or indirectly (e.g., by biotinylation of the sdAb and binding of the biotinylated antibody to a streptavidin fluorochrome conjugate). Such fluorescently labelled IL12Rb1+ cells may be separated from a mixed cell population using conventional FACS technology.

In an alternative embodiment, the selection procedure employs IL12Rb1 binding molecules of the present disclosure (e.g., a IL12RB1 binding VHH) conjugated to magnetic particles which provide magnetic labeling of the IL12Rb1+ cells for use in magnetic cell separation procedures. In one embodiment the method comprises: (a) conjugation of one or more IL12Rb1 binding molecule of the present disclosure (e.g., a IL12RB1 binding VHH) to a magnetic particle; (b) creating a mixture by contacting the biological sample with a quantity of the magnetic particles conjugated to IL12Rb1 binding molecule; (c) subjecting to a magnetic field such that the magnetically labelled IL12Rb1+ cells are retained; (d) removing the non-magnetically labelled cells from the mixture; and (e) removal of the magnetic field enabling isolation of the IL12Rb1+ cells.

The cell selection procedure (e.g., FACS or magnetic separation) results in two products: (a) a population of cells depleted of IL12Rb1+ cells and (b) a population of cells enriched for IL12Rb1+ cells. Each of these populations may be further processed by convention procedures to identify particular IL12Rb1+ or IL12Rb1− cell subsets which may be useful in research, diagnostic or clinical applications. For example, isolation of specific IL12Rb1+ T cell subsets that also express one or more of CD4, CD8, CD19, CD25, and CD62L, further iterations of the using one or more antibodies that specifically bind to CD4, CD8, CD19, CD25, and CD62L antigens respectively by FACS or magnetic field separation by techniques well known in the art.

In one embodiment of the IL12Rb1 binding molecule a humanized antibody or fragment thereof as disclosed herein may be used for depletion of IL12Rb1-expressing cells from a biological sample comprising IL12Rb1-expressing cells such peripheral blood or lymphoid tissue which may optionally be further processed for further isolation of IL12Rb1+ naïve T cell subsets, isolation human IL12Rb1+ memory T cells from a population of CD4+ or CD8+ cells, or isolation of human IL12Rb1RA+naïve T cells from presorted CD4+ or CD8+ cells by depletion of IL12Rb1+ cells. In one embodiment, the IL12Rb1 binding molecule provides a method of generating a population of cells enriched for naïve Tregs from a biological sample, the method comprising depleting IL12Rb1+ cells using a IL12Rb1 binding molecule of the present disclosure as described above, optionally further comprising the steps of depleting CD8+ and/or CD19+ cells. The IL12Rb1+ depleted cell population may optionally be further expanded in vitro for particular cell types to in the preparation of a cell product comprising a therapeutically effective amount of the IL12Rb1+ depleted cell product which may be administered to a subject suffering from a disease, disorder or condition.

The IL12Rb1+ enriched cell population may optionally be further expanded in vitro to in the preparation of a cell product comprising a therapeutically effective amount of the IL12Rb1+ cells.

Kits

The present disclosure also contemplates kits comprising pharmaceutical compositions of IL12Rb1 binding molecules. The kits are generally in the form of a physical structure housing various components, as described below, and can be utilized, for example, in practicing the methods described above. When the IL12Rb1 binding molecule is in a form that requires reconstitution by a user, the kit may also comprise a sterile container providing a reconstitution medium comprising buffers, pharmaceutically acceptable excipients, and the like. A kit of the present disclosure can be designed for conditions necessary to properly maintain the components housed therein (e.g., refrigeration or freezing). A kit may further contain a label or packaging insert including identifying information for the components therein and instructions for their use. Each component of the kit can be enclosed within an individual container, and all of the various containers can be within a single package. Labels or inserts can include manufacturer information such as lot numbers and expiration dates. The label or packaging insert can be, e.g., integrated into the physical structure housing the components, contained separately within the physical structure, or affixed to a component of the kit (e.g., an ampule, syringe or vial). Labels or inserts may be provided in a physical form or a computer readable medium. In some embodiments, the actual instructions are not present in the kit, but rather the kit provides a means for obtaining the instructions from a remote source, e.g., via an internet site, including by secure access by providing a password (or scannable code such as a barcode or QR code on the container of the IL12Rb1 binding molecule or kit comprising) in compliance with governmental regulations (e.g., HIPAA) are provided.

EXAMPLES

The following examples are put forth so as to provide those of ordinary skill in the art with a complete disclosure and description of how to make and use the present IL12Rb1 binding molecule and are not intended to limit the scope of what the inventors regard as their IL12Rb1 binding molecule nor are they intended to represent that the experiments below were performed and are all of the experiments that can be performed. It is to be understood that exemplary descriptions written in the present tense were not necessarily performed, but rather that the descriptions can be performed to generate the data and the like described therein. Efforts have been made to ensure accuracy with respect to numbers used (e.g., amounts, temperature, etc.), but some experimental errors and deviations should be accounted for. Variations of the particularly described procedures employed may become apparent to individuals or skill in the art and it is expected that those skilled artisans may employ such variations as appropriate. Accordingly, it is intended that the IL12Rb1 binding molecule be practiced otherwise than as specifically described herein, and that the invention includes all modifications and equivalents of the subject matter recited in the claims appended hereto as permitted by applicable law.

Unless indicated otherwise, parts are parts by weight, molecular weight is weight average molecular weight, temperature is in degrees Celsius (° C.), and pressure is at or near atmospheric. Standard abbreviations are used, including the following: bp=base pair(s); kb=kilobase(s); pl=picoliter(s); s or sec=second(s); min=minute(s); h or hr=hour(s); aa=amino acid(s); kb=kilobase(s); nt=nucleotide(s); pg=picogram; ng=nanogram; μg=microgram; mg=milligram; g=gram; kg=kilogram; dl or dL=deciliter; μl or μL=microliter; ml or mL=milliliter; l or L=liter; μM=micromolar; mM=millimolar; M=molar; kDa=kilodalton; i.m.=intramuscular(ly); i.p.=intraperitoneal (ly); SC or SQ=subcutaneous(ly); QD=daily; BID=twice daily; QW=weekly; QM=monthly; HPLC=high performance liquid chromatography; BW=body weight; U=unit; ns=not statistically significant; PBS=phosphate-buffered saline; PCR=polymerase chain reaction; NHS=N-hydroxysuccinimide; HSA=human serum albumin; MSA=mouse serum albumin; DMEM=Dulbeco's Modification of Eagle's Medium; GC=genome copy; EDTA=ethylen- ediaminetetraacetic acid; PBMCs=primary peripheral blood mononuclear cells; FBS=fetal bovine serum; FCS=fetal calf serum; HEPES=4-(2-hydroxyethyl)-lpiperazineethanesulfonic acid; LPS=lipopolysaccharide; ATCC=American Type Culture Collection.

Example 1. Immunization Protocol

The process for isolation of the anti-hIL12Rb2 VHHs was initiated by immunization of a camel with a polypeptide corresponding to amino acids 24-622 of hIL12Rb2, (UNIPROT Reference No. Q99665). The process for isolation of the anti-m IL12Rb2 VHHs was the initiated by immunization of a camel with the with the 614 amino acid extracellular domain of the mIL12Rb2, amino acids 24-637 of the m IL12Rb2 precursor (UNIPROT Reference No. P97378).

With respect to each antigen, the following methodology was used to identify and isolate the VHHs.

The synthetic DNA sequence encoding the antigen was inserted into the pFUSE_hIgG1_Fc2 vector (Generay Biotechnology) and transfected into the HEK293F mammalian cell host cell for expression. The antigen is expressed as an Fc fusion protein which is purified using Protein A chromatography. The antigen was diluted with 1xPBS (antigen total about 1 mg). The quality was estimated by SDS-PAGE to ensure the purity was sufficient (>80%) for immunization. The camel was acclimated at the facility for at least 7 days before immunization. The immunization with the antigen was conducted using once weekly administration of the antigen over a period of 7 weeks. For the initial immunization, the immunogen was prepared as follows: 10 mL of complete Freund's Adjuvant (CFA) was added into mortar, then 10 mL antigen in 1xPBS was slowly added into the mortar with the pestle grinding and sample ground until the antigen was emulsified until milky white and hard to disperse. For the subsequent six immunizations (weeks 2-7) in the immunization protocol, immunogen was prepared as above except that Incomplete Freund's Adjuvant (IFA) was used in place of CFA. At least six sites on the camel were injected subcutaneously with approximately 2 ml of the emulsified antigen for a total of approximately 10 mL per camel. When injecting the antigen, the needle is maintained in the in the subcutaneous space for approximately 10 to 15 seconds after each injection to avoid leakage of the emulsion.

Example 2. Phage Library Construction

A blood sample was collected from the camel three days following the last injection in the immunization protocol. RNA was extracted from blood and transcribed to cDNA. The approximately 900 bp reverse transcribed sequences encoding the VH-CH1-hinge-CH2-CH3 constructs were isolated from the approximately desired 700 bp fragments encoding the VHH-hinge-CH2-CH3 species. The purified approximately 700 bp fragments were amplified by nested PCR. The amplified sequences were digested using Pst1 and Not1. The approximately 400 bp PST1/Not1 digested fragments were inserted into a Pst1/Not1 digested pMECS phagemid vector such that the sequence encoding the VHH was in frame with a DNA sequence encoding a HA/His sequence. The PCR generated sequences and the vector of pMECS phagemid were digested with PstI and NotI, subsequently, ligated to pMECS/Nb recombinant. After ligation, the products were transformed into *Escherichia coli* (*E. coli*) TG1 cells by electroporation. The transformants were enriched in growth medium, followed by transfer to 2YT+ 2% glucose agar plates.

Example 3: Isolation of Antigen Specific VHHs

Bio-panning of the phage library was conducted to identify VHHs that bind IL12Rb1. A 96-well plate was coated with IL12Rb1 and the phage library was incubated in each well to allow phage-expressing IL12Rb1 reactive VHH to bind to the IL12Rb1 on the plate. Non-specifically bound phage were washed off and the specifically bound phage isolated. After the selection, the enriched phage library expressing IL12Rb1 reactive VHH were amplified in TG1 cells. The aforementioned bio-panning process was repeated for 2-3 rounds to enrich the library for VHH selective for IL12Rb1.

Example 4: Identification of Antibodies Exhibiting Specific Binding to IL12Rb1

Upon completion of the biopanning of Example 3, three 96-well plates of individual phage clones were isolated in order to perform periplasmic extract ELISA (PE-ELISA) on IL12Rb1 coated plates to identify positive VHH binders that selectively bound IL12Rb1. A 96-well plate was coated with IL12Rb1 and PBS under the same conditions. Next, wells were blocked at 37° C. for 1 h. Then, 100 µl of extracted antibodies was added to each well and incubated for 1 h. Subsequently, 100 µl of anti-tag polyclonal antibody conjugated to HRP was added to each well and incubated at 37° C. for 1 h. Plates were developed with TMB substrate. The reaction was stopped by the addition of H2SO4. Absorbance at 450 nm was read on a microtiter plate reader. Antibodies with absorbance of the antigen-coated well at least threefold greater than PB S-coated control are VHHs that specifically bind to IL12Rb1. Positive clones were sequenced, and sequences analyzed to identify unique clonotypes.

The invention claimed is:

1. An IL12Rb1 binding molecule that specifically binds to the extracellular domain of IL12Rb1, wherein the IL12Rb1 binding molecule comprises a single domain antibody (sdAb), and wherein the sdAb comprises:
   (1) a complementary determining region 1 (CDR1) comprising the sequence of SEQ ID NO:24, a CDR2 comprising the sequence of SEQ ID NO:25, and a CDR3 comprising the sequence of SEQ ID NO:26;
   (2) a CDR1 comprising the sequence of SEQ ID NO:87, a CDR2 comprising the sequence of SEQ ID NO:88, and a CDR3 comprising the sequence of SEQ ID NO:89; or
   (3) a CDR1 comprising the sequence of SEQ ID NO:75, a CDR2 comprising the sequence of SEQ ID NO:76, and a CDR3 comprising the sequence of SEQ ID NO:77.

2. The IL12Rb1 binding molecule of claim 1, wherein the sdAb comprises: a CDR1 comprising the sequence of SEQ ID NO:24, a CDR2 comprising the sequence of SEQ ID NO:25, and a CDR3 comprising the sequence of SEQ ID NO:26.

3. The IL12Rb1 binding molecule of claim 2, wherein the sdAb comprises an amino acid sequence having at least 95% sequence identity to SEQ ID NO:2.

4. The IL12Rb1 binding molecule of claim 1, wherein the sdAb comprises: a CDR1 comprising the sequence of SEQ ID NO:87, a CDR2 comprising the sequence of SEQ ID NO:88, and a CDR3 comprising the sequence of SEQ ID NO:89.

5. The IL12Rb1 binding molecule of claim 4, wherein the sdAb comprises an amino acid sequence having at least 95% sequence identity to SEQ ID NO:23.

6. The IL12Rb1 binding molecule of claim 1, wherein the sdAb comprises: a CDR1 comprising the sequence of SEQ ID NO:75, a CDR2 comprising the sequence of SEQ ID NO:76, and a CDR3 comprising the sequence of SEQ ID NO:77.

7. The IL12Rb1 binding molecule of claim 6, wherein the sdAb comprises an amino acid sequence having at least 95% sequence identity to SEQ ID NO:19.

8. The IL12Rb1 binding molecule of claim 1, wherein the sdAb is humanized or comprises CDRs grafted onto a heterologous framework.

9. The IL12Rb1 binding molecule of claim 1, further comprising a labeling agent, an imaging agent, and/or a therapeutic agent.

10. A kit comprising the IL12Rb1 binding molecule of claim 1.

11. A nucleic acid encoding the IL12Rb1 binding molecule of claim 1.

12. A recombinant vector comprising the nucleic acid of claim 11.

13. A host cell comprising the nucleic acid of claim 11.

14. A method of isolating, depleting or enriching IL12Rb1$^+$ cells from a biological sample comprising: i) contacting the biological sample with the IL12Rb1 binding molecule of claim 1, allowing the binding of said molecule to IL12Rb1 on the IL12Rb1$^+$ cells; and ii) isolating, depleting or enriching the IL12Rb1$^+$ cells that bind the IL12Rb1 binding molecule from the biological sample.

* * * * *

SEQUENCE LISTING

```
<160> NUMBER OF SEQ ID NOS: 235

<210> SEQ ID NO 1
<211> LENGTH: 662
<212> TYPE: PRT
<213> ORGANISM: Homo sapiens

<400> SEQUENCE: 1

Met Glu Pro Leu Val Thr Trp Val Val Pro Leu Leu Phe Leu Phe Leu
1               5                   10                  15

Leu Ser Arg Gln Gly Ala Ala Cys Arg Thr Ser Glu Cys Cys Phe Gln
            20                  25                  30

Asp Pro Pro Tyr Pro Asp Ala Asp Ser Gly Ser Ala Ser Gly Pro Arg
        35                  40                  45

Asp Leu Arg Cys Tyr Arg Ile Ser Ser Asp Arg Tyr Glu Cys Ser Trp
    50                  55                  60

Gln Tyr Glu Gly Pro Thr Ala Gly Val Ser His Phe Leu Arg Cys Cys
65                  70                  75                  80
```

```
Leu Ser Ser Gly Arg Cys Cys Tyr Phe Ala Ala Gly Ser Ala Thr Arg
                85                  90                  95
Leu Gln Phe Ser Asp Gln Ala Gly Val Ser Val Leu Tyr Thr Val Thr
            100                 105                 110
Leu Trp Val Glu Ser Trp Ala Arg Asn Gln Thr Glu Lys Ser Pro Glu
        115                 120                 125
Val Thr Leu Gln Leu Tyr Asn Ser Val Lys Tyr Glu Pro Pro Leu Gly
    130                 135                 140
Asp Ile Lys Val Ser Lys Leu Ala Gly Gln Leu Arg Met Glu Trp Glu
145                 150                 155                 160
Thr Pro Asp Asn Gln Val Gly Ala Glu Val Gln Phe Arg His Arg Thr
                165                 170                 175
Pro Ser Ser Pro Trp Lys Leu Gly Asp Cys Gly Pro Gln Asp Asp Asp
            180                 185                 190
Thr Glu Ser Cys Leu Cys Pro Leu Glu Met Asn Val Ala Gln Glu Phe
        195                 200                 205
Gln Leu Arg Arg Arg Gln Leu Gly Ser Gln Gly Ser Ser Trp Ser Lys
    210                 215                 220
Trp Ser Ser Pro Val Cys Val Pro Pro Glu Asn Pro Pro Gln Pro Gln
225                 230                 235                 240
Val Arg Phe Ser Val Glu Gln Leu Gly Gln Asp Gly Arg Arg Arg Leu
                245                 250                 255
Thr Leu Lys Glu Gln Pro Thr Gln Leu Glu Leu Pro Glu Gly Cys Gln
            260                 265                 270
Gly Leu Ala Pro Gly Thr Glu Val Thr Tyr Arg Leu Gln Leu His Met
        275                 280                 285
Leu Ser Cys Pro Cys Lys Ala Lys Ala Thr Arg Thr Leu His Leu Gly
    290                 295                 300
Lys Met Pro Tyr Leu Ser Gly Ala Ala Tyr Asn Val Ala Val Ile Ser
305                 310                 315                 320
Ser Asn Gln Phe Gly Pro Gly Leu Asn Gln Thr Trp His Ile Pro Ala
                325                 330                 335
Asp Thr His Thr Glu Pro Val Ala Leu Asn Ile Ser Val Gly Thr Asn
            340                 345                 350
Gly Thr Thr Met Tyr Trp Pro Ala Arg Ala Gln Ser Met Thr Tyr Cys
        355                 360                 365
Ile Glu Trp Gln Pro Val Gly Gln Asp Gly Gly Leu Ala Thr Cys Ser
    370                 375                 380
Leu Thr Ala Pro Gln Asp Pro Asp Pro Ala Gly Met Ala Thr Tyr Ser
385                 390                 395                 400
Trp Ser Arg Glu Ser Gly Ala Met Gly Gln Glu Lys Cys Tyr Tyr Ile
                405                 410                 415
Thr Ile Phe Ala Ser Ala His Pro Glu Lys Leu Thr Leu Trp Ser Thr
            420                 425                 430
Val Leu Ser Thr Tyr His Phe Gly Gly Asn Ala Ser Ala Ala Gly Thr
        435                 440                 445
Pro His His Val Ser Val Lys Asn His Ser Leu Asp Ser Val Ser Val
    450                 455                 460
Asp Trp Ala Pro Ser Leu Leu Ser Thr Cys Pro Gly Val Leu Lys Glu
465                 470                 475                 480
Tyr Val Val Arg Cys Arg Asp Glu Asp Ser Lys Gln Val Ser Glu His
                485                 490                 495
```

```
Pro Val Gln Pro Thr Glu Thr Gln Val Thr Leu Ser Gly Leu Arg Ala
                500                 505                 510

Gly Val Ala Tyr Thr Val Gln Val Arg Ala Asp Thr Ala Trp Leu Arg
            515                 520                 525

Gly Val Trp Ser Gln Pro Gln Arg Phe Ser Ile Glu Val Gln Val Ser
        530                 535                 540

Asp Trp Leu Ile Phe Phe Ala Ser Leu Gly Ser Phe Leu Ser Ile Leu
545                 550                 555                 560

Leu Val Gly Val Leu Gly Tyr Leu Gly Leu Asn Arg Ala Ala Arg His
                565                 570                 575

Leu Cys Pro Pro Leu Pro Thr Pro Cys Ala Ser Ser Ala Ile Glu Phe
            580                 585                 590

Pro Gly Gly Lys Glu Thr Trp Gln Trp Ile Asn Pro Val Asp Phe Gln
        595                 600                 605

Glu Glu Ala Ser Leu Gln Glu Ala Leu Val Val Glu Met Ser Trp Asp
610                 615                 620

Lys Gly Glu Arg Thr Glu Pro Leu Glu Lys Thr Glu Leu Pro Glu Gly
625                 630                 635                 640

Ala Pro Glu Leu Ala Leu Asp Thr Glu Leu Ser Leu Glu Asp Gly Asp
            645                 650                 655

Arg Cys Lys Ala Lys Met
            660

<210> SEQ ID NO 2
<211> LENGTH: 126
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 2

Gln Val Gln Leu Gln Glu Ser Gly Gly Ser Val Gln Ala Gly Gly
1               5                   10                  15

Ser Leu Arg Leu Ser Cys Val Ala Ser Gly Tyr Gly Tyr Cys Gly Tyr
            20                  25                  30

Asp Met Ser Trp Tyr Arg Gln Ala Pro Gly Lys Glu Arg Glu Phe Val
        35                  40                  45

Ala Leu Ile Thr Ser Asp Arg Ser Ile Ser Tyr Glu Asp Ser Val Lys
    50                  55                  60

Ala Arg Phe Ile Ile Ser Arg Asp Asn Ala Ala Asn Thr Gly Tyr Leu
65                  70                  75                  80

Asp Met Thr Arg Leu Thr Pro Asp Asp Thr Ala Ile Tyr Tyr Cys Lys
                85                  90                  95

Thr Ser Ala Ala Ala Arg Glu Ser Ser Trp Cys Arg Ser Arg Tyr Arg
            100                 105                 110

Val Ala Ser Trp Gly Gln Gly Thr Gln Val Thr Val Ser Ser
        115                 120                 125

<210> SEQ ID NO 3
<211> LENGTH: 127
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 3
```

Gln Val Gln Leu Gln Glu Ser Gly Gly Gly Ser Val Gln Ala Gly Gly
1               5                   10                  15

Ser Leu Arg Leu Ser Cys Thr Ala Ser Gly Tyr Thr Tyr Ser Ser Ala
            20                  25                  30

Phe Met Ala Trp Phe Arg Gln Ala Pro Gly Lys Glu Arg Glu Gly Val
        35                  40                  45

Ala Ala Ile Tyr Thr Arg Asp Gly Thr Val Tyr Ala Asp Ser Val
    50                  55                  60

Lys Gly Arg Phe Thr Ile Ser Gln Asp Asn Ala Lys Asn Ile Leu Tyr
65                  70                  75                  80

Leu Gln Met Asn Ser Leu Lys Ala Glu Asp Thr Ala Met Tyr Tyr Cys
            85                  90                  95

Ala Ala Lys Ile Pro Gln Pro Gly Arg Ala Ser Leu Leu Asp Ser Gln
            100                 105                 110

Thr Tyr Asp Tyr Trp Gly Gln Gly Thr Gln Val Thr Val Ser Ser
            115                 120                 125

<210> SEQ ID NO 4
<211> LENGTH: 126
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 4

Gln Val Gln Leu Gln Glu Ser Gly Gly Gly Ser Val Gln Ala Gly Gly
1               5                   10                  15

Ser Leu Arg Leu Ser Cys Val Ala Ser Gly Tyr Ser Tyr Cys Gly Tyr
            20                  25                  30

Asp Met Met Trp Tyr Arg Gln Ala Pro Gly Lys Glu Arg Glu Phe Val
        35                  40                  45

Ala Leu Ile Thr Ser Asp Tyr Ser Ile Arg Tyr Glu Asp Ser Val Glu
    50                  55                  60

Gly Arg Phe Ser Ile Ser Arg Asp Asn Ala Lys Asn Thr Gly Tyr Leu
65                  70                  75                  80

Leu Met Ser Asn Leu Thr Pro Ala Asp Thr Ala Ile Tyr Tyr Cys Lys
            85                  90                  95

Thr Ser Thr Ala Ala Arg Glu Ser Ser Trp Cys Arg Ser Arg Tyr Arg
            100                 105                 110

Val Ala Ser Trp Gly Gln Gly Thr Gln Val Thr Val Ser Ser
            115                 120                 125

<210> SEQ ID NO 5
<211> LENGTH: 126
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 5

Gln Val Gln Leu Gln Glu Ser Gly Gly Gly Ser Val Gln Ala Gly Gly
1               5                   10                  15

Ser Leu Arg Leu Ser Cys Val Ala Ser Gly Tyr Gly Tyr Cys Gly Tyr
            20                  25                  30

Asp Met Ser Trp Tyr Arg Gln Thr Pro Gly Lys Glu Arg Glu Phe Val
        35                  40                  45

```
Ala Leu Ile Thr Ser Asp Arg Ile Ala Ser Tyr Glu Asp Ser Val Lys
        50                  55                  60

Gly Arg Phe Ile Ile Ser Arg Asp Asn Ala Lys Asn Thr Gly Tyr Leu
65                  70                  75                  80

Asp Met Thr Arg Val Thr Pro Asp Asp Thr Ala Ile Tyr Tyr Cys Lys
                    85                  90                  95

Thr Ser Ala Ala Ala Arg Glu Asn Ser Trp Cys Arg Ser Arg Tyr Arg
                100                 105                 110

Val Ala Ser Trp Gly Gln Gly Thr Gln Val Thr Val Ser Ser
            115                 120                 125
```

<210> SEQ ID NO 6
<211> LENGTH: 126
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 6

```
Gln Val Gln Leu Gln Glu Ser Gly Gly Gly Ser Val Gln Ala Gly Gly
1               5                   10                  15

Phe Leu Arg Leu Ser Cys Val Ala Ser Gly Tyr Gly Tyr Cys Gly Tyr
                20                  25                  30

Asp Met Ser Trp Tyr Arg Gln Val Pro Gly Lys Glu Arg Glu Phe Val
                35                  40                  45

Ala Leu Ile Thr Ser Asp Arg Ser Val Ser Tyr Glu Asp Ser Val Lys
        50                  55                  60

Gly Arg Phe Ser Ile Ser Arg Asp Asn Ala Lys Asn Thr Ala Tyr Leu
65                  70                  75                  80

Glu Met Asn Arg Leu Thr Pro Asp Asp Thr Ala Val Tyr Tyr Cys Lys
                    85                  90                  95

Thr Ser Thr Ala Ala Arg Glu Asn Asn Trp Cys Arg Ser Arg Tyr Arg
                100                 105                 110

Ile Ala Tyr Trp Gly Gln Gly Thr Gln Val Thr Val Ser Ser
            115                 120                 125
```

<210> SEQ ID NO 7
<211> LENGTH: 127
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 7

```
Gln Val Gln Leu Gln Glu Ser Gly Gly Gly Ser Val Gln Ala Gly Gly
1               5                   10                  15

Ser Leu Arg Leu Ser Cys Ala Ala Ser Arg Tyr Thr Tyr Thr Asn Asn
                20                  25                  30

Phe Met Ala Trp Phe Arg Gln Ala Pro Gly Lys Glu Arg Glu Gly Val
                35                  40                  45

Ala Ala Ile Tyr Thr Gly Asp Gly Tyr Ala Tyr Phe Tyr Ser Val
        50                  55                  60

Lys Gly Arg Phe Thr Ile Ser Gln Asp Asn Asp Glu Asn Met Leu Tyr
65                  70                  75                  80

Leu Gln Met Asn Ser Leu Lys Pro Glu Asp Thr Ala Met Tyr Tyr Cys
                    85                  90                  95
```

Ala Ala Met Glu Arg Arg Ile Gly Thr Arg Arg Met Thr Glu Asn Ala
            100                 105                 110

Glu Tyr Lys Tyr Trp Gly Gln Gly Thr Gln Val Thr Val Ser Ser
        115                 120                 125

<210> SEQ ID NO 8
<211> LENGTH: 126
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 8

Gln Val Gln Leu Gln Glu Ser Gly Gly Gly Ser Val Gln Ala Gly Gly
1               5                   10                  15

Ser Leu Arg Leu Ser Cys Ala Val Ser Gly Tyr Asp Tyr Cys Gly Tyr
            20                  25                  30

Asp Val Arg Trp Tyr Arg Arg Ala Pro Gly Lys Glu Arg Glu Phe Val
        35                  40                  45

Ser Gly Ile Asp Ser Asp Gly Ser Thr Ser Tyr Ala Asp Ser Val Lys
    50                  55                  60

Gly Arg Phe Thr Ile Ser Gln Asp Asn Ala Glu Asn Thr Ser Tyr Leu
65                  70                  75                  80

His Met Phe Ser Leu Lys Pro Glu Asp Thr Ala Met Tyr Tyr Cys Lys
                85                  90                  95

Thr Glu Ser Pro Ala Gly Glu Ser Ala Trp Cys Arg Asn Phe Arg Gly
            100                 105                 110

Met Asp Tyr Trp Gly Lys Gly Thr Gln Val Thr Val Ser Ser
        115                 120                 125

<210> SEQ ID NO 9
<211> LENGTH: 126
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 9

Gln Val Gln Leu Gln Glu Ser Gly Gly Gly Ser Val Gln Ala Gly Gly
1               5                   10                  15

Ser Leu Arg Leu Ser Cys Val Ala Ser Gly Tyr Ser Tyr Cys Gly Tyr
            20                  25                  30

Asp Met Met Trp Tyr Arg Gln Ala Pro Gly Lys Glu Arg Glu Phe Val
        35                  40                  45

Ala Leu Ile Thr Ser Asp Tyr Ser Ile Arg Tyr Glu Asp Ser Val Glu
    50                  55                  60

Gly Arg Phe Ser Ile Ser Arg Asp Asn Ala Lys Asn Thr Gly Tyr Leu
65                  70                  75                  80

Leu Met Ser Asn Leu Thr Pro Ala Asp Thr Ala Ile Tyr Tyr Cys Lys
                85                  90                  95

Thr Ser Thr Ala Ala Arg Glu Ser Ser Trp Cys Arg Ser Arg Tyr Arg
            100                 105                 110

Val Ala Ser Trp Gly Gln Gly Thr Gln Val Thr Val Ser Ser
        115                 120                 125

<210> SEQ ID NO 10
<211> LENGTH: 126

```
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 10

Gln Val Gln Leu Gln Glu Ser Gly Gly Gly Ser Val Gln Ala Gly Gly
1               5                   10                  15

Ser Leu Arg Leu Ser Cys Val Ala Ser Gly Tyr Ser Tyr Cys Gly Tyr
            20                  25                  30

Asp Met Met Trp Tyr Arg Gln Ala Pro Gly Lys Glu Arg Glu Phe Val
        35                  40                  45

Ala Leu Ile Thr Ser Asp Tyr Ser Ile Arg Tyr Glu Asp Ser Val Glu
    50                  55                  60

Gly Arg Phe Ser Ile Ser Arg Asp Asn Ala Lys Asn Thr Gly Tyr Leu
65                  70                  75                  80

Leu Met Ser Asn Leu Thr Pro Ala Asp Thr Ala Ile Tyr Tyr Cys Lys
                85                  90                  95

Thr Ser Thr Ala Ala Arg Glu Ser Gly Trp Cys Arg Ser Arg Tyr Arg
            100                 105                 110

Val Ala Ser Trp Gly Gln Gly Thr Gln Val Thr Val Ser Ser
        115                 120                 125

<210> SEQ ID NO 11
<211> LENGTH: 126
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 11

Gln Val Gln Leu Gln Glu Ser Gly Gly Gly Ser Val Gln Ala Gly Gly
1               5                   10                  15

Ser Leu Arg Leu Ser Cys Ala Val Ser Gly Tyr Asp Tyr Cys Gly Tyr
            20                  25                  30

Asp Val Arg Trp Tyr Arg Gln Ala Pro Gly Lys Glu Arg Glu Phe Val
        35                  40                  45

Ser Gly Ile Asp Ser Asp Gly Ser Thr Ser Tyr Ala Asp Ser Val Lys
    50                  55                  60

Gly Arg Phe Thr Ile Ser Gln Asp Asn Ala Glu Asn Thr Ser Tyr Leu
65                  70                  75                  80

His Met Phe Ser Leu Lys Pro Glu Asp Thr Ala Met Tyr Tyr Cys Lys
                85                  90                  95

Thr Glu Ser Pro Ala Gly Glu Ser Ala Trp Cys Arg Asn Phe Arg Gly
            100                 105                 110

Met Asp Tyr Trp Gly Lys Gly Thr Gln Val Thr Val Ser Ser
        115                 120                 125

<210> SEQ ID NO 12
<211> LENGTH: 126
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 12

Gln Val Gln Leu Gln Glu Ser Gly Gly Gly Ser Val Gln Ala Gly Gly
```

```
1               5                   10                  15
Ser Leu Arg Leu Ser Cys Ala Val Ser Gly Tyr Asp Tyr Cys Gly Tyr
            20                  25                  30

Asp Val Arg Trp Tyr Arg Gln Ala Pro Gly Lys Glu Arg Glu Phe Val
            35                  40                  45

Ser Gly Ile Asp Ser Asp Gly Ser Thr Ser Tyr Ala Asp Ser Val Lys
            50                  55                  60

Gly Arg Phe Thr Ile Ser Gln Asp Asn Ala Glu Asn Thr Ser Tyr Leu
65                  70                  75                  80

His Met Phe Ser Leu Lys Pro Glu Asp Thr Ala Met Tyr Tyr Cys Lys
            85                  90                  95

Thr Glu Ser Pro Ala Gly Glu Ser Ala Trp Cys Arg Asn Phe Arg Gly
            100                 105                 110

Met Asp Tyr Trp Gly Lys Gly Thr Gln Val Thr Val Ser Ser
            115                 120                 125
```

<210> SEQ ID NO 13
<211> LENGTH: 127
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 13

```
Gln Val Gln Leu Gln Glu Ser Gly Gly Gly Ser Val Gln Ala Gly Gly
1               5                   10                  15

Ser Leu Arg Leu Ser Cys Thr Ala Ser Gly Tyr Thr Tyr Ser Ser Ala
            20                  25                  30

Phe Met Ala Trp Phe Arg Gln Ala Pro Gly Lys Glu Arg Glu Gly Val
            35                  40                  45

Ala Ala Ile Tyr Thr Arg Asp Gly Gly Thr Val Tyr Ala Asp Ser Val
            50                  55                  60

Lys Gly Arg Phe Thr Ile Ser Gln Asp Asn Ala Lys Asn Thr Leu Tyr
65                  70                  75                  80

Leu Gln Met Asn Ser Leu Lys Pro Glu Asp Thr Ala Met Tyr Tyr Cys
            85                  90                  95

Ala Ala Lys Met Pro Gln Pro Gly Arg Ala Ser Leu Leu Asp Ser Gln
            100                 105                 110

Thr Tyr Asp Tyr Trp Gly Gln Gly Thr Gln Val Thr Val Ser Ser
            115                 120                 125
```

<210> SEQ ID NO 14
<211> LENGTH: 126
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 14

```
Gln Val Gln Leu Gln Glu Ser Gly Gly Gly Ser Val Gln Ala Gly Gly
1               5                   10                  15

Phe Leu Arg Leu Ser Cys Val Ala Ser Gly Tyr Gly Tyr Cys Gly Tyr
            20                  25                  30

Asp Met Ser Trp Tyr Arg Gln Ala Pro Gly Lys Glu Arg Glu Phe Val
            35                  40                  45

Ala Leu Ile Thr Ser Glu Arg Val Ile Ser Tyr Glu Asp Ser Val Lys
```

```
                 50                  55                  60

Gly Arg Phe Ser Ile Ser Arg Asp Asn Ala Glu Asn Thr Gly Tyr Leu
 65                  70                  75                  80

Glu Met Asn Arg Leu Thr Pro Asp Asp Thr Ala Ile Tyr Tyr Cys Lys
                 85                  90                  95

Thr Ser Ala Ala Arg Glu Ser Trp Cys Arg Ser Arg Tyr Arg
            100                 105                 110

Val Ala Ser Trp Gly Gln Gly Thr Gln Val Thr Val Ser Ser
            115                 120                 125

<210> SEQ ID NO 15
<211> LENGTH: 126
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 15

Gln Val Gln Leu Gln Glu Ser Gly Gly Gly Ser Val Gln Ala Gly Gly
 1                5                  10                  15

Ser Leu Arg Leu Ser Cys Ala Val Ser Gly Tyr Asp Tyr Cys Gly Tyr
                 20                  25                  30

Asp Val Arg Trp Tyr Arg Arg Ala Pro Gly Lys Glu Arg Glu Phe Val
            35                  40                  45

Ser Gly Ile Asp Ser Asp Gly Ser Thr Ser Tyr Ala Asp Ser Val Lys
     50                  55                  60

Gly Arg Phe Thr Ile Ser Gln Asp Asn Ala Glu Asn Thr Ser Tyr Leu
 65                  70                  75                  80

His Met Phe Ser Leu Lys Pro Glu Asp Thr Ala Met Tyr Tyr Cys Lys
                 85                  90                  95

Thr Glu Ser Pro Ala Gly Glu Ser Ala Trp Cys Arg Asn Phe Arg Gly
            100                 105                 110

Met Asp Tyr Trp Gly Lys Gly Thr Gln Val Thr Val Ser Ser
            115                 120                 125

<210> SEQ ID NO 16
<211> LENGTH: 126
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 16

Gln Val Gln Leu Gln Glu Ser Gly Gly Gly Ser Val Gln Ala Gly Gly
 1                5                  10                  15

Ser Leu Arg Leu Ser Cys Ala Val Ser Gly Tyr Asp Tyr Cys Gly Tyr
                 20                  25                  30

Asp Val Arg Trp Tyr Arg Gln Ala Pro Gly Lys Glu Arg Glu Phe Val
            35                  40                  45

Ser Gly Ile Asn Ser Asp Gly Ser Thr Ser Tyr Ala Asp Ser Val Lys
     50                  55                  60

Gly Arg Phe Thr Ile Ser Gln Asp Asn Ala Glu Asn Thr Ser Tyr Leu
 65                  70                  75                  80

His Met Phe Ser Leu Lys Pro Glu Asp Thr Ala Met Tyr Tyr Cys Lys
                 85                  90                  95

Thr Glu Ser Pro Ala Gly Glu Ser Ala Trp Cys Arg Asn Phe Arg Gly
```

```
            100                 105                 110

Met Asp Tyr Trp Gly Lys Gly Thr Gln Val Thr Val Ser Ser
        115                 120                 125

<210> SEQ ID NO 17
<211> LENGTH: 127
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 17

Gln Val Gln Leu Gln Glu Ser Gly Gly Gly Ser Val Gln Ala Gly Gly
1               5                   10                  15

Ser Leu Arg Leu Ser Cys Thr Ala Ser Gly Tyr Thr Tyr Ser Ser Ala
            20                  25                  30

Phe Met Ala Trp Phe Arg Gln Ala Pro Gly Lys Glu Arg Glu Gly Val
        35                  40                  45

Ala Ala Met Tyr Thr Arg Asp Gly Gly Thr Val Tyr Ala Asp Ser Val
    50                  55                  60

Lys Gly Arg Phe Thr Ile Ser Gln Asp Asn Ala Lys Asn Thr Leu Tyr
65                  70                  75                  80

Leu Gln Ile His Thr Leu Lys Ala Glu Asp Thr Ala Met Tyr Tyr Cys
                85                  90                  95

Ala Ala Lys Ile Pro Gln Pro Gly Arg Ala Ser Leu Leu Asp Ser Gln
            100                 105                 110

Thr Tyr Asp Tyr Trp Gly Gln Gly Thr Gln Val Thr Val Ser Ser
        115                 120                 125

<210> SEQ ID NO 18
<211> LENGTH: 126
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 18

Gln Val Gln Leu Gln Glu Ser Gly Gly Gly Ser Val Gln Ala Gly Gly
1               5                   10                  15

Phe Leu Arg Leu Ser Cys Val Ala Ser Gly Tyr Gly Tyr Cys Gly Tyr
            20                  25                  30

Asp Met Ser Trp Tyr Arg Gln Val Pro Gly Lys Glu Arg Glu Phe Val
        35                  40                  45

Ala Leu Ile Thr Ser Asp Arg Ser Val Ser Tyr Glu Asp Ser Val Lys
    50                  55                  60

Gly Arg Phe Ser Ile Ser Arg Asp Asn Ala Lys Asn Thr Ala Tyr Leu
65                  70                  75                  80

Glu Met Asn Arg Leu Thr Pro Asp Asp Thr Ala Ile Tyr Tyr Cys Lys
                85                  90                  95

Thr Ser Thr Ala Ala Arg Glu Asn Asn Trp Cys Arg Ser Arg Tyr Arg
            100                 105                 110

Ile Ala Ser Trp Gly Gln Gly Thr Gln Val Thr Val Ser Ser
        115                 120                 125

<210> SEQ ID NO 19
<211> LENGTH: 127
<212> TYPE: PRT
```

<213> ORGANISM: Artificial Sequence
<220> FEATURE:
<223> OTHER INFORMATION: Description of Artificial Sequence: Synthetic
      polypeptide

<400> SEQUENCE: 19

```
Gln Val Gln Leu Gln Glu Ser Gly Gly Gly Ser Val Gln Ala Gly Gly
1               5                   10                  15

Ser Leu Arg Leu Ser Cys Ala Ala Ser Arg Tyr Thr Tyr Thr Asn Asn
            20                  25                  30

Phe Met Ala Trp Phe Arg Gln Ala Pro Gly Lys Glu Arg Glu Gly Val
        35                  40                  45

Ala Ala Ile Tyr Thr Gly Asp Gly Tyr Ala Tyr Tyr Phe Asp Ser Val
    50                  55                  60

Lys Gly Arg Phe Thr Ile Ser Gln Asp Asn Asp Lys Asn Met Leu Tyr
65                  70                  75                  80

Leu Gln Met Asn Ser Leu Lys Pro Glu Asp Thr Ala Met Tyr Tyr Cys
                85                  90                  95

Ala Ala Met Glu Arg Arg Ser Gly Arg Arg Met Thr Glu Asn Ala
            100                 105                 110

Glu Tyr Lys Tyr Trp Gly Gln Gly Thr Gln Val Thr Val Ser Ser
            115                 120                 125
```

<210> SEQ ID NO 20
<211> LENGTH: 126
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 20

```
Gln Val Gln Leu Gln Glu Ser Gly Gly Gly Ser Val Gln Ala Gly Gly
1               5                   10                  15

Ser Leu Arg Leu Ser Cys Ala Val Ser Gly Tyr Asp Tyr Cys Gly Tyr
            20                  25                  30

Asp Val Arg Trp Tyr Arg Gln Ala Pro Gly Lys Glu Arg Glu Phe Val
        35                  40                  45

Ser Gly Ile Asn Ser Asp Gly Ser Thr Ser Tyr Ala Asp Ser Val Lys
    50                  55                  60

Gly Arg Phe Thr Ile Ser Gln Asp Asn Ala Glu Asn Thr Ser Tyr Leu
65                  70                  75                  80

His Met Phe Ser Leu Lys Pro Glu Asp Thr Ala Met Tyr Tyr Cys Lys
                85                  90                  95

Thr Glu Gly Pro Ala Gly Glu Ser Ala Trp Cys Arg Asn Phe Arg Gly
            100                 105                 110

Met Asp Tyr Trp Gly Lys Gly Thr Gln Val Thr Val Ser Ser
            115                 120                 125
```

<210> SEQ ID NO 21
<211> LENGTH: 127
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 21

```
Gln Val Gln Leu Gln Glu Ser Gly Gly Gly Ser Val Gln Ala Gly Gly
1               5                   10                  15
```

```
Ser Leu Arg Leu Ser Cys Thr Ala Ser Gly Tyr Thr Tyr Ser Ser Ala
            20                  25                  30

Phe Met Ala Trp Phe Arg Gln Ala Pro Gly Lys Glu Arg Glu Gly Val
        35                  40                  45

Ala Ala Ile Tyr Thr Arg Asp Gly Ser Pro Val Tyr Ala Asp Ser Leu
    50                  55                  60

Lys Gly Arg Phe Thr Ile Ser Gln Asp Asn Ala Lys Asn Thr Leu His
65                  70                  75                  80

Leu Gln Met Asn Ser Leu Lys Pro Glu Asp Thr Ala Met Tyr Tyr Cys
                85                  90                  95

Ala Ala Lys Ile Pro Glu Pro Gly Arg Ile Ser Leu Leu Asp Ser Gln
            100                 105                 110

Thr Tyr Asp Tyr Trp Gly His Gly Thr Gln Val Thr Val Ser Ser
            115                 120                 125

<210> SEQ ID NO 22
<211> LENGTH: 127
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 22

Gln Val Gln Leu Gln Glu Ser Gly Gly Gly Ser Val Gln Ala Gly Gly
1               5                   10                  15

Ser Leu Arg Leu Ser Cys Thr Ala Ser Gly Tyr Thr Tyr Ser Ser Ala
            20                  25                  30

Phe Met Ala Trp Phe Arg Gln Ala Pro Gly Lys Glu Arg Glu Gly Val
        35                  40                  45

Ala Ala Met Tyr Thr Arg Asp Gly Gly Thr Val Tyr Ala Asp Ser Val
    50                  55                  60

Lys Gly Arg Phe Thr Ile Ser Gln Asp Asn Ala Lys Asn Thr Leu Tyr
65                  70                  75                  80

Leu Gln Met Asn Ser Leu Lys Thr Glu Asp Thr Ala Met Tyr Tyr Cys
                85                  90                  95

Ala Ala Lys Ile Pro Gln Pro Gly Arg Ala Ser Leu Leu Asp Ser Gln
            100                 105                 110

Thr Tyr Asp Tyr Trp Gly Gln Gly Thr Gln Val Thr Val Ser Ser
            115                 120                 125

<210> SEQ ID NO 23
<211> LENGTH: 127
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 23

Gln Val Gln Leu Gln Glu Ser Gly Gly Gly Ser Val Gln Ala Gly Gly
1               5                   10                  15

Ser Leu Arg Leu Ser Cys Thr Ala Ser Gly Tyr Thr Tyr Ser Ser Ala
            20                  25                  30

Phe Met Ala Trp Phe Arg Gln Ala Pro Gly Lys Glu Arg Glu Gly Val
        35                  40                  45

Ala Ala Ile Tyr Thr Arg Asp Gly Gly Thr Val Tyr Ala Asp Ser Val
    50                  55                  60
```

```
Lys Gly Arg Phe Thr Ile Ser Gln Asp Asn Ala Lys Asn Thr Leu Tyr
 65                  70                  75                  80

Leu Gln Met Asn Ser Leu Lys Ala Glu Asp Thr Ala Met Tyr Tyr Cys
                 85                  90                  95

Ala Ala Lys Ile Pro Gln Pro Gly Arg Ala Ser Leu Leu Asp Ser Gln
            100                 105                 110

Thr Tyr Asp Tyr Trp Gly Gln Gly Thr Gln Val Thr Val Ser Ser
        115                 120                 125

<210> SEQ ID NO 24
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 24

Tyr Gly Tyr Cys Gly Tyr Asp Met Ser
1               5

<210> SEQ ID NO 25
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 25

Leu Ile Thr Ser Asp Arg Ser Ile Ser Tyr Glu Asp Ser Val Lys Ala
1               5                   10                  15

<210> SEQ ID NO 26
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 26

Ser Ala Ala Ala Arg Glu Ser Ser Trp Cys Arg Ser Arg Tyr Arg Val
1               5                   10                  15

Ala Ser

<210> SEQ ID NO 27
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 27

Tyr Thr Tyr Ser Ser Ala Phe Met Ala
1               5

<210> SEQ ID NO 28
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
```

<400> SEQUENCE: 28

Ala Ile Tyr Thr Arg Asp Gly Gly Thr Val Tyr Ala Asp Ser Val Lys
1               5                   10                  15

Gly

<210> SEQ ID NO 29
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 29

Lys Ile Pro Gln Pro Gly Arg Ala Ser Leu Leu Asp Ser Gln Thr Tyr
1               5                   10                  15

Asp Tyr

<210> SEQ ID NO 30
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 30

Tyr Ser Tyr Cys Gly Tyr Asp Met Met
1               5

<210> SEQ ID NO 31
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 31

Leu Ile Thr Ser Asp Tyr Ser Ile Arg Tyr Glu Asp Ser Val Glu Gly
1               5                   10                  15

<210> SEQ ID NO 32
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 32

Ser Thr Ala Ala Arg Glu Ser Ser Trp Cys Arg Ser Arg Tyr Arg Val
1               5                   10                  15

Ala Ser

<210> SEQ ID NO 33
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 33

```
Tyr Gly Tyr Cys Gly Tyr Asp Met Ser
1               5
```

<210> SEQ ID NO 34
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 34

```
Leu Ile Thr Ser Asp Arg Ile Ala Ser Tyr Glu Asp Ser Val Lys Gly
1               5                   10                  15
```

<210> SEQ ID NO 35
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 35

```
Ser Ala Ala Ala Arg Glu Asn Ser Trp Cys Arg Ser Arg Tyr Arg Val
1               5                   10                  15

Ala Ser
```

<210> SEQ ID NO 36
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 36

```
Tyr Gly Tyr Cys Gly Tyr Asp Met Ser
1               5
```

<210> SEQ ID NO 37
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 37

```
Leu Ile Thr Ser Asp Arg Ser Val Ser Tyr Glu Asp Ser Val Lys Gly
1               5                   10                  15
```

<210> SEQ ID NO 38
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 38

```
Ser Thr Ala Ala Arg Glu Asn Asn Trp Cys Arg Ser Arg Tyr Arg Ile
1               5                   10                  15

Ala Tyr
```

<210> SEQ ID NO 39

```
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 39

Tyr Thr Tyr Thr Asn Asn Phe Met Ala
1               5

<210> SEQ ID NO 40
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 40

Ala Ile Tyr Thr Gly Asp Gly Tyr Ala Tyr Tyr Phe Tyr Ser Val Lys
1               5                   10                  15

Gly

<210> SEQ ID NO 41
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 41

Met Glu Arg Arg Ile Gly Thr Arg Arg Met Thr Glu Asn Ala Glu Tyr
1               5                   10                  15

Lys Tyr

<210> SEQ ID NO 42
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 42

Tyr Asp Tyr Cys Gly Tyr Asp Val Arg
1               5

<210> SEQ ID NO 43
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 43

Gly Ile Asp Ser Asp Gly Ser Thr Ser Tyr Ala Asp Ser Val Lys Gly
1               5                   10                  15

<210> SEQ ID NO 44
<211> LENGTH: 18
<212> TYPE: PRT
<213> ORGANISM: Artificial Sequence
<220> FEATURE:
<223> OTHER INFORMATION: Description of Artificial Sequence: Synthetic
``` peptide

<400> SEQUENCE: 44

Glu Ser Pro Ala Gly Glu Ser Ala Trp Cys Arg Asn Phe Arg Gly Met
1               5                   10                  15

Asp Tyr

<210> SEQ ID NO 45
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 45

Tyr Ser Tyr Cys Gly Tyr Asp Met Met
1               5

<210> SEQ ID NO 46
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 46

Leu Ile Thr Ser Asp Tyr Ser Ile Arg Tyr Glu Asp Ser Val Glu Gly
1               5                   10                  15

<210> SEQ ID NO 47
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 47

Ser Thr Ala Ala Arg Glu Ser Ser Trp Cys Arg Ser Arg Tyr Arg Val
1               5                   10                  15

Ala Ser

<210> SEQ ID NO 48
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 48

Tyr Ser Tyr Cys Gly Tyr Asp Met Met
1               5

<210> SEQ ID NO 49
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 49

Leu Ile Thr Ser Asp Tyr Ser Ile Arg Tyr Glu Asp Ser Val Glu Gly

<210> SEQ ID NO 50
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 50

Ser Thr Ala Ala Arg Glu Ser Gly Trp Cys Arg Ser Arg Tyr Arg Val
1               5                   10                  15

Ala Ser

<210> SEQ ID NO 51
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 51

Tyr Asp Tyr Cys Gly Tyr Asp Val Arg
1               5

<210> SEQ ID NO 52
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 52

Gly Ile Asp Ser Asp Gly Ser Thr Ser Tyr Ala Asp Ser Val Lys Gly
1               5                   10                  15

<210> SEQ ID NO 53
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 53

Glu Ser Pro Ala Gly Glu Ser Ala Trp Cys Arg Asn Phe Arg Gly Met
1               5                   10                  15

Asp Tyr

<210> SEQ ID NO 54
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 54

Tyr Asp Tyr Cys Gly Tyr Asp Val Arg
1               5

<210> SEQ ID NO 55
<211> LENGTH: 16

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 55

Gly Ile Asp Ser Asp Gly Ser Thr Ser Tyr Ala Asp Ser Val Lys Gly
1               5                   10                  15

<210> SEQ ID NO 56
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 56

Glu Ser Pro Ala Gly Glu Ser Ala Trp Cys Arg Asn Phe Arg Gly Met
1               5                   10                  15

Asp Tyr

<210> SEQ ID NO 57
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 57

Tyr Thr Tyr Ser Ser Ala Phe Met Ala
1               5

<210> SEQ ID NO 58
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 58

Ala Ile Tyr Thr Arg Asp Gly Gly Thr Val Tyr Ala Asp Ser Val Lys
1               5                   10                  15

Gly

<210> SEQ ID NO 59
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 59

Lys Met Pro Gln Pro Gly Arg Ala Ser Leu Leu Asp Ser Gln Thr Tyr
1               5                   10                  15

Asp Tyr

<210> SEQ ID NO 60
<211> LENGTH: 9
<212> TYPE: PRT
<213> ORGANISM: Artificial Sequence
<220> FEATURE:
```

```
<223> OTHER INFORMATION: Description of Artificial Sequence: Synthetic
      peptide

<400> SEQUENCE: 60

Tyr Gly Tyr Cys Gly Tyr Asp Met Ser
1               5

<210> SEQ ID NO 61
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 61

Leu Ile Thr Ser Glu Arg Val Ile Ser Tyr Glu Asp Ser Val Lys Gly
1               5                   10                  15

<210> SEQ ID NO 62
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 62

Ser Ala Ala Ala Arg Glu Ser Ser Trp Cys Arg Ser Arg Tyr Arg Val
1               5                   10                  15

Ala Ser

<210> SEQ ID NO 63
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 63

Tyr Asp Tyr Cys Gly Tyr Asp Val Arg
1               5

<210> SEQ ID NO 64
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 64

Gly Ile Asp Ser Asp Gly Ser Thr Ser Tyr Ala Asp Ser Val Lys Gly
1               5                   10                  15

<210> SEQ ID NO 65
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 65

Glu Ser Pro Ala Gly Glu Ser Ala Trp Cys Arg Asn Phe Arg Gly Met
1               5                   10                  15
```

Asp Tyr

<210> SEQ ID NO 66
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 66

Tyr Asp Tyr Cys Gly Tyr Asp Val Arg
1               5

<210> SEQ ID NO 67
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 67

Gly Ile Asn Ser Asp Gly Ser Thr Ser Tyr Ala Asp Ser Val Lys Gly
1               5                   10                  15

<210> SEQ ID NO 68
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 68

Glu Ser Pro Ala Gly Glu Ser Ala Trp Cys Arg Asn Phe Arg Gly Met
1               5                   10                  15
Asp Tyr

<210> SEQ ID NO 69
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 69

Tyr Thr Tyr Ser Ser Ala Phe Met Ala
1               5

<210> SEQ ID NO 70
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 70

Ala Met Tyr Thr Arg Asp Gly Gly Thr Val Tyr Ala Asp Ser Val Lys
1               5                   10                  15
Gly

<210> SEQ ID NO 71

<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 71

Lys Ile Pro Gln Pro Gly Arg Ala Ser Leu Leu Asp Ser Gln Thr Tyr
1               5                   10                  15

Asp Tyr

<210> SEQ ID NO 72
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 72

Tyr Gly Tyr Cys Gly Tyr Asp Met Ser
1               5

<210> SEQ ID NO 73
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 73

Leu Ile Thr Ser Asp Arg Ser Val Ser Tyr Glu Asp Ser Val Lys Gly
1               5                   10                  15

<210> SEQ ID NO 74
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 74

Ser Thr Ala Ala Arg Glu Asn Asn Trp Cys Arg Ser Arg Tyr Arg Ile
1               5                   10                  15

Ala Ser

<210> SEQ ID NO 75
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 75

Tyr Thr Tyr Thr Asn Asn Phe Met Ala
1               5

<210> SEQ ID NO 76
<211> LENGTH: 17
<212> TYPE: PRT
<213> ORGANISM: Artificial Sequence
<220> FEATURE:
<223> OTHER INFORMATION: Description of Artificial Sequence: Synthetic peptide

<400> SEQUENCE: 76

Ala Ile Tyr Thr Gly Asp Gly Tyr Ala Tyr Tyr Phe Asp Ser Val Lys
1               5                   10                  15
Gly

<210> SEQ ID NO 77
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 77

Met Glu Arg Arg Ser Gly Arg Arg Met Thr Glu Asn Ala Glu Tyr
1               5                   10                  15
Lys Tyr

<210> SEQ ID NO 78
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 78

Tyr Asp Tyr Cys Gly Tyr Asp Val Arg
1               5

<210> SEQ ID NO 79
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 79

Gly Ile Asn Ser Asp Gly Ser Thr Ser Tyr Ala Asp Ser Val Lys Gly
1               5                   10                  15

<210> SEQ ID NO 80
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 80

Glu Gly Pro Ala Gly Glu Ser Ala Trp Cys Arg Asn Phe Arg Gly Met
1               5                   10                  15
Asp Tyr

<210> SEQ ID NO 81
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 81

```
Tyr Thr Tyr Ser Ser Ala Phe Met Ala
1               5

<210> SEQ ID NO 82
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 82

Ala Ile Tyr Thr Arg Asp Gly Ser Pro Val Tyr Ala Asp Ser Leu Lys
1               5                   10                  15

Gly

<210> SEQ ID NO 83
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 83

Lys Ile Pro Glu Pro Gly Arg Ile Ser Leu Leu Asp Ser Gln Thr Tyr
1               5                   10                  15

Asp Tyr

<210> SEQ ID NO 84
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 84

Tyr Thr Tyr Ser Ser Ala Phe Met Ala
1               5

<210> SEQ ID NO 85
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 85

Ala Met Tyr Thr Arg Asp Gly Gly Thr Val Tyr Ala Asp Ser Val Lys
1               5                   10                  15

Gly

<210> SEQ ID NO 86
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 86

Lys Ile Pro Gln Pro Gly Arg Ala Ser Leu Leu Asp Ser Gln Thr Tyr
1               5                   10                  15
```

Asp Tyr

<210> SEQ ID NO 87
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 87

Tyr Thr Tyr Ser Ser Ala Phe Met Ala
1               5

<210> SEQ ID NO 88
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 88

Ala Ile Tyr Thr Arg Asp Gly Gly Thr Val Tyr Ala Asp Ser Val Lys
1               5                   10                  15

Gly

<210> SEQ ID NO 89
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 89

Lys Ile Pro Gln Pro Gly Arg Ala Ser Leu Leu Asp Ser Gln Thr Tyr
1               5                   10                  15

Asp Tyr

<210> SEQ ID NO 90
<211> LENGTH: 378
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 90
caggtccagc tccaggagtc tggcggtggc tcagtacaag ctgggggctc tctgcgtttg     60
tcctgtgtgg cgagcgggta cggatactgt gggtacgaca tgagttggta cagacaggcc    120
cctggcaagg aacgtgaatt tgtggccctc atcacttctg atcgctccat tagctacgag    180
gattctgtca agctcgctt tatcatttcc cgcgacaacg ccgctaacac tggttatctg    240
gacatgacta gactgacccc cgatgacacg gccatttact attgcaagac cagtgcagcg    300
gcccgcgaat cttcctggtg tcgctctcgc taccgcgtgg catcatgggg ccagggtact    360
caggtcaccg tgtctagc                                                  378

<210> SEQ ID NO 91
<211> LENGTH: 381
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 91

```
caagtccaac tccaggagtc tggtgggggc tctgttcaag ctggcgggtc cctgcgcctt    60
tcctgtaccg ccagcggcta cacgtactct agcgccttca tggcttggtt tcggcaggcc   120
cctggaaaag agagagaggg agtggcagct atctacactc gtgacggcgg aaccgtgtac   180
gctgatagtg tcaagggccg cttcaccatt tcccaggata atgccaagaa tatcctgtat   240
ctccagatga actcccttaa agccgaagac actgcgatgt actattgcgc agccaaaatc   300
ccgcagccag gccgggcttc tttgctggat agccaaacct acgactattg gggtcaaggc   360
actcaggtta ccgtgtcttc c                                              381
```

<210> SEQ ID NO 92
<211> LENGTH: 378
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 92

```
caggtccagc ttcaggagag cggcggaggc tccgtgcagg ctgggggatc tttgagactc    60
agctgcgtgg ccagtggcta ctcttactgt gggtacgaca tgatgtggta tcgccaagcg   120
ccgggcaagg aacgtgagtt cgtggcgctc atcacttccg actactcaat tcgttacgag   180
gattccgttg agggccgctt cagcatttct cgtgacaacg cgaagaacac aggatacttg   240
ctgatgagta acctcacccc cgccgatacc gctatttatt actgcaagac aagtacagct   300
gccagggaga gcagttggtg tcggtctcgc tatcgtgtgg cctcctgggg acagggcacc   360
caagtaaccg tgtcatca                                                  378
```

<210> SEQ ID NO 93
<211> LENGTH: 378
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 93

```
caggtgcagc tccaggaatc tggtgggggc agtgttcagg ctggtggcag cctgagactt    60
agctgcgtgg cttctggcta tggttactgt gggtacgaca tgagctggta tcggcagacc   120
cccggaaagg agcgggagtt cgtagcgctc atcacaagtg accgcatcgc ctcctatgaa   180
gactccgtta agggtcgctt tatcattagc cgggacaatg ccaagaacac aggttacctc   240
gatatgactc gggtcacacc tgacgatacc gctatctatt actgcaagac ttctgcggct   300
gcccgtgaaa acagctggtg ccgctcaaga taccgggtgg cctcctgggg acagggaact   360
caggtcaccg tctctagc                                                  378
```

<210> SEQ ID NO 94
<211> LENGTH: 378
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 94

```
caggtgcagt tgcaggagag cggaggcgga tctgtgcagg ccggtggatt tctgcggctg      60
tcttgcgtgg cgagcggcta tggctattgc ggatacgaca tgagctggta tcgccaggtt     120
ccgggtaagg agcgtgagtt cgtcgctctg attacctctg atcgctctgt gtcctatgag     180
gactccgtta agggtagatt ctctatctct cgcgataatg ctaagaacac agcctacctg     240
gagatgaaca gactgacccc cgacgatacc gctgtctatt actgtaagac ctccacagcc     300
gctcgcgaga ataactggtg ccgctctcgc tatagaatcg cctattgggg tcagggtaca     360
caagttaccg tatcctcc                                                   378
```

<210> SEQ ID NO 95
<211> LENGTH: 381
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 95

```
caggtgcagt tgcaggagag tggcgggggc tctgttcagg ctggtggatc attgcgtctg      60
agctgtgctg cctcccgcta cacctacact aataacttca tggcttggtt tagacaagct    120
cctggcaagg aacgcgaagg cgttgccgcg atttataccg gagacggtta cgcatattac    180
ttctattccg tgaagggccg cttcacaatc tcccaggata cgacgaaaa tatgctctac     240
ttgcagatga actccctcaa acctgaggac acggcaatgt actattgtgc ggctatggag    300
cgccgtatcg gaactcgccg tatgaccgaa aacgctgagt ataagtattg gggacaagga    360
acccaggtga ccgtatcctc c                                               381
```

<210> SEQ ID NO 96
<211> LENGTH: 378
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 96

```
caggtccagt tgcaggagtc tggtggcgga agcgtgcagg ctgggggcag cctcaggctg      60
tcctgtgctg tgtccgggta cgactactgc ggctacgacg tgcgctggta tcgccgtgcc    120
cccggcaagg agagggagtt cgtctccggg attgattccg atggctctac cagttacgca    180
gattccgtca agggtcgttt taccattagt caggataacg ctgagaacac aagctatctg    240
cacatgttct cactgaagcc tgaggatacg gccatgtact attgcaagac tgagtccccc    300
gcaggtgaat ccgcctggtg tcgtaacttt cgcggcatgg actactgggg aaagggcacc    360
caggtcactg tgtcttct                                                   378
```

<210> SEQ ID NO 97
<211> LENGTH: 378
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 97

```
caggtgcagc tccaggaatc aggcggtggg tccgtgcagg caggagggag tctgcgcctg      60
```

-continued

```
tcctgtgtgg cctccggtta cagctactgc ggctacgata tgatgtggta taggcaagct    120
ccagggaagg agcgtgagtt cgtggccctt atcacatctg actattccat ccgctacgag    180
gactccgtgg agggaagatt ttcaatctcc agagacaacg caaagaacac cggatacctc    240
ctgatgtcta acctgacccc agccgacacg gcaatctatt actgtaaaac ctccacagca    300
gcgagggagt ccagctggtg caggtccaga taccgtgttg cctcctgggg acagggcact    360
caggtgacgg tgagttct                                                  378
```

<210> SEQ ID NO 98
<211> LENGTH: 378
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 98

```
caggtgcagc tccaggagtc cggtggcggg agcgtgcagg ctggcggatc tctgcggctc     60
agttgcgtcg cctcagggta ttcctattgt ggctacgata tgatgtggta tcgtcaggcc    120
cccggcaagg agcgcgagtt cgtcgccctg attacaagcg attattcaat ccgttatgaa    180
gattccgtgg aggggcgctt ctccatcagt cgcgacaacg ccaaaaacac tggctacctt    240
ctgatgtcaa acctgactcc cgctgacacc gcgatctact attgtaaaac ctcaacggct    300
gcccgcgagt ccggctggtg ccggtctagg tatcgtgtgg ccagctgggg gcagggcact    360
caggtcaccg tgtcatcc                                                  378
```

<210> SEQ ID NO 99
<211> LENGTH: 378
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 99

```
caggtccagc tgcaagaatc cggtggaggc tctgtgcagg cgggtgggtc cctgcgcctg     60
tcttgcgccg tgtctggcta tgattattgc ggatatgacg tgcgctggta tcgccaggct    120
cccggcaagg aacgcgagtt tgtctctggg attgactcag acggcagcac tagctatgcc    180
gactccgtga aggtcgcctt caccatttcc aagacaacg ccgagaatac cagctatctg    240
cacatgttca gcctcaaacc tgaagatact gccatgtatt actgtaagac ggagagtccc    300
gcaggcgaat ccgcttggtg tcggaatttc aggggaatgg actactgggg caagggtact    360
caagtgaccg taagctct                                                  378
```

<210> SEQ ID NO 100
<211> LENGTH: 378
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 100

```
caggtgcagc tccaggagag cggcggaggc tccgtgcagg cgggcgggag cctgcgtctg     60
tcttgtgccg tatctggcta tgactattgc ggttacgacg ttcgctggta caggcaggct    120
ccgggcaagg agcgtgagtt tgtcagcggg attgacagtg acggctccac ctcttatgcg    180
```

```
gattccgtga agggacgctt cacaatttcc caggataacg cagagaacac ctcctacctc    240
cacatgttca gcctcaaacc cgaagatact gctatgtatt actgtaaaac agagagccca    300
gccggggagt ctgcttggtg tcgtaacttt cgcggcatgg actactgggg caagggaacc    360
caggtgaccg tctcttcc                                                  378
```

<210> SEQ ID NO 101
<211> LENGTH: 381
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 101

```
caggtgcaac tccaagagag cggaggcggg agtgttcagg ccggggggctc tctgcggctg     60 tcctgcaccg cctctggtta cacctactcc agcgccttca tggcctggtt ccggcaggca    120
cctggcaagg aacgcgaagg cgtagccgct atctatacgc gcgatggggg tacagtttat    180
gctgatagcg ttaaaggacg cttcactatc tcccaggaca acgccaaaaa cacctgtac     240 ttgcagatga actccctcaa acctgaagat acgcgatgt actattgtgc ggcaaagatg    300
cctcagcccg gacgcgcaag tctgcttgac tctcaaactt atgattactg gggccaaggg    360
actcaggtga ccgttagctc c                                              381
```

<210> SEQ ID NO 102
<211> LENGTH: 378
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 102

```
caggtgcagt tgcaggaaag cggcggtggc tcagtccagg ccggggggctt cttgcgcttg     60 agttgcgtgg cgagcggata tggctactgt ggctacgata tgagctggta tcgtcaggct    120
ccgggcaagg aacgtgagtt cgtcgcgctc atcactagcg aaagagtcat ctcctacgaa    180
gactccgtta agggccgctt ttccatttct cgcgacaacg ccgagaacac gggctacctt    240
gaaatgaata gactgactcc cgacgatact gccatctact attgcaagac aagcgccgct    300
gcacgcgagt cctcttggtg caggtctcgc taccgcgtgg cttcttgggg gcaggggacc    360
caggtgaccg tatcatcc                                                  378
```

<210> SEQ ID NO 103
<211> LENGTH: 378
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 103

```
caggttcaac tccaggagtc cggggggcggt tccgtgcagg ctgggggctc ccttagactt     60
agctgtgccg tgtctggata cgattactgt gggtatgacg tgcggtggta cagacgcgct    120
ccgggaaagg aacgcgagtt cgtgagcgga attgattccg atggcagcac ctcctatgcg    180
gattctgtga agggccgctt cactatctct caagacaacg ccgagaacac tagctacctg    240
cacatgttca gtctgaaacc ggaggatacc gcgatgtatt actgtaagac cgagtctcct    300
```

```
gctggagaga gcgcgtggtg cagaaacttc cgtggaatgg actattgggg taaaggaact    360
caggtgactg tgtccagt                                                  378

<210> SEQ ID NO 104
<211> LENGTH: 378
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 104
caagtgcagc tccaggaatc tggaggcgga agcgtacagg ccggtggctc actccggctt    60
tcttgcgctg tgtcaggtta cgactattgt ggatatgatg tccggtggta taggcaagcg   120
ccgggaaagg agcgcgagtt cgtgagcggt atcaactctg acggctccac ctcctacgcc   180
gactctgtca agggccgctt tacaatttct caggacaacg cagagaacac ctcttacctg   240
cacatgttca gcttgaagcc ggaggacacc gcgatgtact attgtaagac tgagtccccc   300
gctggagagt ctgcatggtg ccgtaatttt cgcggcatgg actattgggg gaaaggtact   360
caggttaccg taagctca                                                  378

<210> SEQ ID NO 105
<211> LENGTH: 381
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 105
caggtacagc tccaggagag tggaggcggg tcagtgcagg ccgggggctc actgcgcttg    60
agctgcaccg cgagcggtta cacctacagc tccgcattca tggcttggtt caggcaagcc   120
ccaggcaagg agcgcgaggg cgtggctgcc atgtatatccc gcgacggggg caccgtgtat   180
gccgattccg tgaagggccg tttcaccatc tcccaggata cgctaagaa caccctctac    240 ctccagatcc acactctcaa agccgaagac acggctatgt actattgcgc cgcgaagatc   300
cctcaacctg gcagggcaag ccttctggac tcccagacgt atgactattg gggccagggg   360
actcaggtta cagtgtccag c                                              381

<210> SEQ ID NO 106
<211> LENGTH: 378
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 106
caggtgcagc tccaggaatc cggcggtggg tctgtgcagg caggggggttt tctccgcttg    60 agctgtgtgg ctagtggata cggttattgt ggatacgaca tgagctggta tcgccaagta   120
ccgggcaagg agcgtgagtt tgtggccctc atcacctctg atcgctccgt gtcttatgag   180
gacagcgtga agggccgctt cagcatcagt cgcgacaacg ccaagaacac cgcttatctg   240
gaaatgaaca gactcacccc ggatgacaca gctatctact attgcaagac ctccacagcg   300
gccagagaga ataactggtg ccggtcccgc taccgcatcg cgtcctgggg ccagggcacc   360
caggtgactg tctcctct                                                  378
```

<210> SEQ ID NO 107
<211> LENGTH: 381
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 107
caggtgcagt tgcaggagtc tggagggggc agcgtgcagg ccggaggctc cctccgcctc    60
agctgcgcgg cctcccggta cacctacacc aataacttca tggcatggtt caggcaggcc   120
ccaggaaagg agcgtgaggg ggtcgccgca atctataccg gagacggcta cgcctattac   180
tttgactccg ttaaagggcg tttcaccatc agtcaagaca cgacaaaaa catgctctac    240 ctccagatga atagcttgaa gccggaggat accgcaatgt actattgtgc cgcgatggag   300
agacgctccg gtcggcgtcg catgactgaa aatgccgagt acaagtactg ggggcagggg   360
actcaggtga ccgtgagcag c                                              381

<210> SEQ ID NO 108
<211> LENGTH: 378
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 108
caagttcagc tccaggagag tggaggcggt tccgtacagg ctggcggaag tctgcgcctc    60
tcctgcgccg tctccggtta cgactattgt gggtacgacg tgcgctggta tagacaggct   120
cctggaaagg agcgtgagtt tgtgagtggc atcaactccg acgtagcac ctcctatgct    180 gattctgtga agggtcgctt tacaatctca caggacaacg ccgaaaacac ttcctatctg   240
cacatgttca gcctcaagcc cgaagacacc gcaatgtact attgtaagac tgaaggtcca   300
gctggcgaga gtgcatggtg caggaatttt aggggcatgg actactgggg caagggcacc   360
caggtcaccg tgtcttca                                                   378

<210> SEQ ID NO 109
<211> LENGTH: 381
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 109
caggtgcagt tgcaggaatc aggaggcggt tctgtgcagg ccggaggcag cctgcgtctg    60
agctgcaccg cttctgggta cacctactca agtgccttca tggcctggtt tcggcaagcg   120
cccggcaagg aacgcgaggg agttgcggcc atctacacca gggacggcag tcccgtgtac   180
gctgactccc tgaagggccg tttcaccatc agccaggata acgcaaagaa cacctgcac    240 ctccagatga acagcctgaa acctgaggac acagctatgt attactgcgc ggccaaaatc   300
cctgagcctg gaagaatcag cctccttgac tcccagacct acgactactg gggtcacggc   360
actcaggtga ctgtgtcttc t                                              381

<210> SEQ ID NO 110
<211> LENGTH: 381
<212> TYPE: DNA

<213> ORGANISM: Artificial Sequence
<220> FEATURE:
<223> OTHER INFORMATION: Description of Artificial Sequence: Synthetic
    polynucleotide

<400> SEQUENCE: 110

```
caggttcaac tccaagagtc tggaggcggg tccgtgcagg ctgggggctc cctcagactg      60
tcctgtactg cgtcaggta  cacctacagc tccgctttca tggcttggtt ccggcaagct     120
ccgggcaagg agcgcgaggg cgtggccgcg atgtataccc gcgacggtgg caccgtgtac     180
gccgactctg ttaaaggccg cttcaccatc tcccaggata cgccaagaa  caccctgtac     240 ctccagatga actctttgaa gaccgaggat accgctatgt actattgcgc cgcaaaaatt     300
ccccagccgg ccgtgcttc  ccttctggac agccaaacct atgattactg ggccagggc      360 acacaggtga ccgtgtcctc c                                                381
```

<210> SEQ ID NO 111
<211> LENGTH: 381
<212> TYPE: DNA
<213> ORGANISM: Artificial Sequence
<220> FEATURE:
<223> OTHER INFORMATION: Description of Artificial Sequence: Synthetic
    polynucleotide

<400> SEQUENCE: 111

```
caggtgcaac ttcaggaatc tggcggtggc agcgtgcagg ctggtggctc cctgcgcctg      60
agctgtactg cttccggcta cacatactct agtgcgttca tggcctggtt caggcaagct     120
ccgggaaagg agcgcgaggg tgtggcggcc atttatacac gcgacggagg caccgtgtac     180
gctgactctg tcaagggccg cttcaccatc tcacaggaca atgcaaaaaa taccctctac     240
cttcagatga acagcctgaa ggcagaggac acagcaatgt attactgtgc agccaagatc     300
ccacaacccg gacgcgcgtc cctcctggat tcacagacct acgactactg ggccagggc      360 acgcaggtta ctgtatcaag c                                                381
```

<210> SEQ ID NO 112
<211> LENGTH: 127
<212> TYPE: PRT
<213> ORGANISM: Artificial Sequence
<220> FEATURE:
<223> OTHER INFORMATION: Description of Artificial Sequence: Synthetic
    polypeptide

<400> SEQUENCE: 112

```
Gln Val Gln Leu Gln Glu Ser Gly Gly Gly Ser Val Gln Ala Gly Gly
1               5                   10                  15

Ser Leu Arg Leu Ser Cys Thr Ala Ser Gly Tyr Thr Tyr Ser Ser Ala
            20                  25                  30

Phe Met Ala Trp Phe Arg Gln Ala Pro Gly Lys Glu Arg Glu Gly Val
        35                  40                  45

Ala Ala Ile Tyr Thr Arg Asp Gly Gly Thr Val Tyr Ala Asp Ser Val
    50                  55                  60

Lys Gly Arg Phe Thr Ile Ser Gln Asp Asn Ala Lys Asn Thr Leu Tyr
65                  70                  75                  80

Leu Gln Met Asn Ser Leu Lys Ala Glu Asp Thr Ala Met Tyr Tyr Cys
                85                  90                  95

Ala Ala Lys Ile Pro Gln Pro Gly Arg Ala Ser Leu Leu Asp Ser Gln
            100                 105                 110

Thr Tyr Asp Tyr Trp Gly Gln Gly Thr Gln Val Thr Val Ser Ser
```

-continued

```
                115                 120                 125

<210> SEQ ID NO 113
<211> LENGTH: 126
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 113

Gln Val Gln Leu Gln Glu Ser Gly Gly Gly Ser Val Gln Ala Gly Gly
1               5                   10                  15

Ser Leu Arg Leu Ser Cys Ala Val Ser Gly Tyr Asp Tyr Cys Gly Tyr
                20                  25                  30

Asp Val Arg Trp Tyr Arg Gln Ala Pro Gly Lys Glu Arg Glu Phe Val
            35                  40                  45

Ser Gly Ile Asp Ser Asp Gly Ser Thr Ser Tyr Ala Asp Ser Val Lys
        50                  55                  60

Gly Arg Phe Thr Ile Ser Gln Asp Asn Ala Glu Asn Thr Ser Tyr Leu
65                  70                  75                  80

His Met Phe Ser Leu Lys Pro Glu Asp Thr Ala Met Tyr Tyr Cys Lys
                85                  90                  95

Thr Glu Ser Pro Ala Gly Glu Ser Ala Trp Cys Arg Asn Phe Arg Gly
            100                 105                 110

Met Asp Tyr Trp Gly Lys Gly Thr Gln Val Thr Val Ser Ser
        115                 120                 125

<210> SEQ ID NO 114
<211> LENGTH: 126
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 114

Gln Val Gln Leu Gln Glu Ser Gly Gly Gly Ser Val Gln Ala Gly Gly
1               5                   10                  15

Ser Leu Arg Leu Ser Cys Val Ala Ser Gly Tyr Ser Tyr Cys Gly Tyr
                20                  25                  30

Asp Met Met Trp Tyr Arg Gln Ala Pro Gly Lys Glu Arg Glu Phe Val
            35                  40                  45

Ala Leu Ile Thr Ser Asp Tyr Ser Ile Arg Tyr Glu Asp Ser Val Glu
        50                  55                  60

Gly Arg Phe Ser Ile Ser Arg Asp Asn Ala Lys Asn Thr Gly Tyr Leu
65                  70                  75                  80

Leu Met Ser Asn Leu Thr Pro Ala Asp Thr Ala Ile Tyr Tyr Cys Lys
                85                  90                  95

Thr Ser Thr Ala Ala Arg Glu Ser Ser Trp Cys Arg Ser Arg Tyr Arg
            100                 105                 110

Val Ala Ser Trp Gly Gln Gly Thr Gln Val Thr Val Ser Ser
        115                 120                 125

<210> SEQ ID NO 115
<211> LENGTH: 127
<212> TYPE: PRT
<213> ORGANISM: Artificial Sequence
<220> FEATURE:
<223> OTHER INFORMATION: Description of Artificial Sequence: Synthetic
```

-continued

```
                polypeptide

<400> SEQUENCE: 115

Gln Val Gln Leu Gln Glu Ser Gly Gly Gly Ser Val Gln Ala Gly Gly
1               5                   10                  15

Ser Leu Arg Leu Ser Cys Ala Ala Ser Arg Tyr Thr Tyr Thr Asn Asn
            20                  25                  30

Phe Met Ala Trp Phe Arg Gln Ala Pro Gly Lys Glu Arg Glu Gly Val
        35                  40                  45

Ala Ala Ile Tyr Thr Gly Asp Gly Tyr Ala Tyr Tyr Phe Asp Ser Val
    50                  55                  60

Lys Gly Arg Phe Thr Ile Ser Gln Asp Asn Asp Lys Asn Met Leu Tyr
65                  70                  75                  80

Leu Gln Met Asn Ser Leu Lys Pro Glu Asp Thr Ala Met Tyr Tyr Cys
                85                  90                  95

Ala Ala Met Glu Arg Arg Ser Gly Arg Arg Arg Met Thr Glu Asn Ala
            100                 105                 110

Glu Tyr Lys Tyr Trp Gly Gln Gly Thr Gln Val Thr Val Ser Ser
        115                 120                 125

<210> SEQ ID NO 116
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 116

Gln Val Gln Leu Gln Glu Ser Gly Gly Gly Ser Val Gln Ala Gly Glu
1               5                   10                  15

Thr Leu Arg Leu Ser Cys Thr Val Ser Gly Phe Thr Ile Asp Asp Ser
            20                  25                  30

Glu Met Gly Trp Tyr Arg Gln Ala Pro Gly His Glu Cys Glu Leu Val
        35                  40                  45

Ala Ser Gly Ser Ser Asp Asp Thr Tyr Tyr Val Asp Ser Val Lys
    50                  55                  60

Gly Arg Phe Thr Ile Ser Leu Asp Asn Ala Lys Asn Met Val Tyr Leu
65                  70                  75                  80

Gln Met Asn Ser Leu Lys Pro Glu Asp Thr Ala Val Tyr Tyr Cys Ala
                85                  90                  95

Thr Gly Pro Thr Tyr Pro Pro Lys Asp Gly Asp Cys Ala His Trp Gly
            100                 105                 110

Gln Gly Thr Gln Val Thr Val Ser Ser
        115                 120

<210> SEQ ID NO 117
<211> LENGTH: 127
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 117

Gln Val Gln Leu Gln Glu Ser Gly Gly Gly Ser Val Gln Ala Gly Gly
1               5                   10                  15

Ser Leu Arg Leu Ser Cys Thr Ala Ser Gly Tyr Thr Tyr Ser Ser Ala
            20                  25                  30
```

Phe Met Ala Trp Phe Arg Gln Ala Pro Gly Lys Glu Arg Glu Gly Val
            35                  40                  45

Ala Ala Ile Tyr Thr Arg Asp Gly Ser Pro Val Tyr Ala Asp Ser Leu
 50                  55                  60

Lys Gly Arg Phe Thr Ile Ser Gln Asp Asn Ala Lys Asn Thr Leu His
 65                  70                  75                  80

Leu Gln Met Asn Ser Leu Lys Pro Glu Asp Thr Ala Met Tyr Tyr Cys
                 85                  90                  95

Ala Ala Lys Ile Pro Glu Pro Gly Arg Ile Ser Leu Leu Asp Ser Gln
            100                 105                 110

Thr Tyr Asp Tyr Trp Gly His Gly Thr Gln Val Thr Val Ser Ser
            115                 120                 125

<210> SEQ ID NO 118
<211> LENGTH: 126
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 118

Gln Val Gln Leu Gln Glu Ser Gly Gly Gly Ser Val Gln Ala Gly Gly
 1               5                  10                  15

Ser Leu Arg Leu Ser Cys Ala Val Ser Gly Tyr Asp Tyr Cys Gly Tyr
             20                  25                  30

Asp Val Arg Trp Tyr Arg Arg Ala Pro Gly Lys Glu Arg Glu Phe Val
            35                  40                  45

Ser Gly Ile Asp Ser Asp Gly Ser Thr Ser Tyr Ala Asp Ser Val Lys
 50                  55                  60

Gly Arg Phe Thr Ile Ser Gln Asp Asn Ala Glu Asn Thr Ser Tyr Leu
 65                  70                  75                  80

His Met Phe Ser Leu Lys Pro Glu Asp Thr Ala Met Tyr Tyr Cys Lys
                 85                  90                  95

Thr Glu Ser Pro Ala Gly Glu Ser Ala Trp Cys Arg Asn Phe Arg Gly
            100                 105                 110

Met Asp Tyr Trp Gly Lys Gly Thr Gln Val Thr Val Ser Ser
            115                 120                 125

<210> SEQ ID NO 119
<211> LENGTH: 126
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 119

Gln Val Gln Leu Gln Glu Ser Gly Gly Gly Ser Val Gln Ala Gly Gly
 1               5                  10                  15

Phe Leu Arg Leu Ser Cys Val Ala Ser Gly Tyr Gly Tyr Cys Gly Tyr
             20                  25                  30

Asp Met Ser Trp Tyr Arg Gln Ala Pro Gly Lys Glu Arg Glu Phe Val
            35                  40                  45

Ala Leu Ile Thr Ser Glu Arg Val Ile Ser Tyr Glu Asp Ser Val Lys
 50                  55                  60

Gly Arg Phe Ser Ile Ser Arg Asp Asn Ala Glu Asn Thr Gly Tyr Leu
 65                  70                  75                  80

Glu Met Asn Arg Leu Thr Pro Asp Asp Thr Ala Ile Tyr Tyr Cys Lys
                85                  90                  95

Thr Ser Ala Ala Ala Arg Glu Ser Ser Trp Cys Arg Ser Arg Tyr Arg
            100                 105                 110

Val Ala Ser Trp Gly Gln Gly Thr Gln Val Thr Val Ser Ser
        115                 120                 125

<210> SEQ ID NO 120
<211> LENGTH: 126
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 120

Gln Val Gln Leu Gln Glu Ser Gly Gly Gly Ser Val Gln Ala Gly Gly
1               5                   10                  15

Ser Leu Arg Leu Ser Cys Val Ala Ser Gly Tyr Gly Tyr Cys Gly Tyr
            20                  25                  30

Asp Met Ser Trp Tyr Arg Gln Ala Pro Gly Lys Glu Arg Glu Phe Val
        35                  40                  45

Ala Leu Ile Thr Ser Asp Arg Ser Ile Ser Tyr Glu Asp Ser Val Lys
    50                  55                  60

Ala Arg Phe Ile Ile Ser Arg Asp Asn Ala Ala Asn Thr Gly Tyr Leu
65                  70                  75                  80

Asp Met Thr Arg Leu Thr Pro Asp Asp Thr Ala Ile Tyr Tyr Cys Lys
                85                  90                  95

Thr Ser Ala Ala Ala Arg Glu Ser Ser Trp Cys Arg Ser Arg Tyr Arg
            100                 105                 110

Val Ala Ser Trp Gly Gln Gly Thr Gln Val Thr Val Ser Ser
        115                 120                 125

<210> SEQ ID NO 121
<211> LENGTH: 126
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 121

Gln Val Gln Leu Gln Glu Ser Gly Gly Gly Ser Val Gln Ala Gly Gly
1               5                   10                  15

Ser Leu Arg Leu Ser Cys Ala Val Ser Gly Tyr Asp Tyr Cys Gly Tyr
            20                  25                  30

Asp Val Arg Trp Tyr Arg Gln Ala Pro Gly Lys Glu Arg Glu Phe Val
        35                  40                  45

Ser Gly Ile Asp Ser Asp Gly Ser Thr Ser Tyr Ala Asp Ser Val Lys
    50                  55                  60

Gly Arg Phe Thr Ile Ser Gln Asp Asn Ala Glu Asn Thr Ser Tyr Leu
65                  70                  75                  80

His Met Phe Ser Leu Lys Pro Glu Asp Thr Ala Met Tyr Tyr Cys Lys
                85                  90                  95

Thr Glu Ser Pro Ala Gly Glu Ser Ala Trp Cys Arg Asn Phe Arg Gly
            100                 105                 110

Met Asp Tyr Trp Gly Lys Gly Thr Gln Val Thr Val Ser Ser
        115                 120                 125

<210> SEQ ID NO 122
<211> LENGTH: 126
<212> TYPE: PRT
<213> ORGANISM: Artificial Sequence
<220> FEATURE:
<223> OTHER INFORMATION: Description of Artificial Sequence: Synthetic
    polypeptide

<400> SEQUENCE: 122

Gln Val Gln Leu Gln Glu Ser Gly Gly Gly Ser Val Gln Ala Gly Gly
1               5                   10                  15

Ser Leu Arg Leu Ser Cys Val Ala Ser Gly Tyr Ser Tyr Cys Gly Tyr
            20                  25                  30

Asp Met Met Trp Tyr Arg Gln Ala Pro Gly Lys Glu Arg Glu Phe Val
        35                  40                  45

Ala Leu Ile Thr Ser Asp Tyr Ser Ile Arg Tyr Glu Asp Ser Val Glu
    50                  55                  60

Gly Arg Phe Ser Ile Ser Arg Asp Asn Ala Lys Asn Thr Gly Tyr Leu
65                  70                  75                  80

Leu Met Ser Asn Leu Thr Pro Ala Asp Thr Ala Ile Tyr Tyr Cys Lys
                85                  90                  95

Thr Ser Thr Ala Ala Arg Glu Ser Ser Trp Cys Arg Ser Arg Tyr Arg
            100                 105                 110

Val Ala Ser Trp Gly Gln Gly Thr Gln Val Thr Val Ser Ser
        115                 120                 125

<210> SEQ ID NO 123
<211> LENGTH: 127
<212> TYPE: PRT
<213> ORGANISM: Artificial Sequence
<220> FEATURE:
<223> OTHER INFORMATION: Description of Artificial Sequence: Synthetic
    polypeptide

<400> SEQUENCE: 123

Gln Val Gln Leu Gln Glu Ser Gly Gly Gly Ser Val Gln Ala Gly Gly
1               5                   10                  15

Ser Leu Arg Leu Ser Cys Ala Ala Ser Arg Tyr Thr Tyr Thr Asn Asn
            20                  25                  30

Phe Met Ala Trp Phe Arg Gln Ala Pro Gly Lys Glu Arg Glu Gly Val
        35                  40                  45

Ala Ala Ile Tyr Thr Gly Asp Gly Tyr Ala Tyr Phe Tyr Ser Val
    50                  55                  60

Lys Gly Arg Phe Thr Ile Ser Gln Asp Asn Asp Glu Asn Met Leu Tyr
65                  70                  75                  80

Leu Gln Met Asn Ser Leu Lys Pro Glu Asp Thr Ala Met Tyr Tyr Cys
                85                  90                  95

Ala Ala Met Glu Arg Arg Ile Gly Thr Arg Arg Met Thr Glu Asn Ala
            100                 105                 110

Glu Tyr Lys Tyr Trp Gly Gln Gly Thr Gln Val Thr Val Ser Ser
        115                 120                 125

<210> SEQ ID NO 124
<211> LENGTH: 126
<212> TYPE: PRT
<213> ORGANISM: Artificial Sequence
<220> FEATURE:
<223> OTHER INFORMATION: Description of Artificial Sequence: Synthetic
    polypeptide

<400> SEQUENCE: 124

Gln Val Gln Leu Gln Glu Ser Gly Gly Gly Ser Val Gln Ala Gly Gly
1               5                   10                  15

Ser Leu Arg Leu Ser Cys Val Ala Ser Gly Tyr Ser Tyr Cys Gly Tyr
                20                  25                  30

Asp Met Met Trp Tyr Arg Gln Ala Pro Gly Lys Glu Arg Glu Phe Val
            35                  40                  45

Ala Leu Ile Thr Ser Asp Tyr Ser Ile Arg Tyr Glu Asp Ser Val Glu
    50                  55                  60

Gly Arg Phe Ser Ile Ser Arg Asp Asn Ala Lys Asn Thr Gly Tyr Leu
65                  70                  75                  80

Leu Met Ser Asn Leu Thr Pro Ala Asp Thr Ala Ile Tyr Tyr Cys Lys
                85                  90                  95

Thr Ser Thr Ala Ala Arg Glu Ser Gly Trp Cys Arg Ser Arg Tyr Arg
            100                 105                 110

Val Ala Ser Trp Gly Gln Gly Thr Gln Val Thr Val Ser Ser
        115                 120                 125

<210> SEQ ID NO 125
<211> LENGTH: 126
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 125

Gln Val Gln Leu Gln Glu Ser Gly Gly Gly Ser Val Gln Ala Gly Gly
1               5                   10                  15

Ser Leu Arg Leu Ser Cys Ala Val Ser Gly Tyr Asp Tyr Cys Gly Tyr
                20                  25                  30

Asp Val Arg Trp Tyr Arg Gln Ala Pro Gly Lys Glu Arg Glu Phe Val
            35                  40                  45

Ser Gly Ile Asn Ser Asp Gly Ser Thr Ser Tyr Ala Asp Ser Val Lys
    50                  55                  60

Gly Arg Phe Thr Ile Ser Gln Asp Asn Ala Glu Asn Thr Ser Tyr Leu
65                  70                  75                  80

His Met Phe Ser Leu Lys Pro Glu Asp Thr Ala Met Tyr Tyr Cys Lys
                85                  90                  95

Thr Glu Ser Pro Ala Gly Glu Ser Ala Trp Cys Arg Asn Phe Arg Gly
            100                 105                 110

Met Asp Tyr Trp Gly Lys Gly Thr Gln Val Thr Val Ser Ser
        115                 120                 125

<210> SEQ ID NO 126
<211> LENGTH: 126
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 126

Gln Val Gln Leu Gln Glu Ser Gly Gly Gly Ser Val Gln Ala Gly Gly
1               5                   10                  15

Phe Leu Arg Leu Ser Cys Val Ala Ser Gly Tyr Gly Tyr Cys Gly Tyr
                20                  25                  30

```
Asp Met Ser Trp Tyr Arg Gln Val Pro Gly Lys Glu Arg Glu Phe Val
            35                  40                  45

Ala Leu Ile Thr Ser Asp Arg Ser Val Ser Tyr Glu Asp Ser Val Lys
 50                  55                  60

Gly Arg Phe Ser Ile Ser Arg Asp Asn Ala Lys Asn Thr Ala Tyr Leu
 65                  70                  75                  80

Glu Met Asn Arg Leu Thr Pro Asp Asp Thr Ala Val Tyr Tyr Cys Lys
                 85                  90                  95

Thr Ser Thr Ala Ala Arg Glu Asn Asn Trp Cys Arg Ser Arg Tyr Arg
            100                 105                 110

Ile Ala Tyr Trp Gly Gln Gly Thr Gln Val Thr Val Ser Ser
            115                 120                 125

<210> SEQ ID NO 127
<211> LENGTH: 126
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 127

Gln Val Gln Leu Gln Glu Ser Gly Gly Gly Ser Val Gln Ala Gly Gly
 1               5                  10                  15

Ser Leu Arg Leu Ser Cys Ala Val Ser Gly Tyr Asp Tyr Cys Gly Tyr
            20                  25                  30

Asp Val Arg Trp Tyr Arg Gln Ala Pro Gly Lys Glu Arg Glu Phe Val
            35                  40                  45

Ser Gly Ile Asn Ser Asp Gly Ser Thr Ser Tyr Ala Asp Ser Val Lys
 50                  55                  60

Gly Arg Phe Thr Ile Ser Gln Asp Asn Ala Glu Asn Thr Ser Tyr Leu
 65                  70                  75                  80

His Met Phe Ser Leu Lys Pro Glu Asp Thr Ala Met Tyr Tyr Cys Lys
                 85                  90                  95

Thr Glu Gly Pro Ala Gly Glu Ser Ala Trp Cys Arg Asn Phe Arg Gly
            100                 105                 110

Met Asp Tyr Trp Gly Lys Gly Thr Gln Val Thr Val Ser Ser
            115                 120                 125

<210> SEQ ID NO 128
<211> LENGTH: 127
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 128

Gln Val Gln Leu Gln Glu Ser Gly Gly Gly Ser Val Gln Ala Gly Gly
 1               5                  10                  15

Ser Leu Arg Leu Ser Cys Thr Ala Ser Gly Tyr Thr Tyr Ser Ser Ala
            20                  25                  30

Phe Met Ala Trp Phe Arg Gln Ala Pro Gly Lys Glu Arg Glu Gly Val
            35                  40                  45

Ala Ala Met Tyr Thr Arg Asp Gly Gly Thr Val Tyr Ala Asp Ser Val
            50                  55                  60

Lys Gly Arg Phe Thr Ile Ser Gln Asp Asn Ala Lys Asn Thr Leu Tyr
 65                  70                  75                  80
```

Leu Gln Ile His Thr Leu Lys Ala Glu Asp Thr Ala Met Tyr Tyr Cys
            85                  90                  95

Ala Ala Lys Ile Pro Gln Pro Gly Arg Ala Ser Leu Leu Asp Ser Gln
        100                 105                 110

Thr Tyr Asp Tyr Trp Gly Gln Gly Thr Gln Val Thr Val Ser Ser
    115                 120                 125

<210> SEQ ID NO 129
<211> LENGTH: 127
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 129

Gln Val Gln Leu Gln Glu Ser Gly Gly Gly Ser Val Gln Ala Gly Gly
1               5                   10                  15

Ser Leu Arg Leu Ser Cys Thr Ala Ser Gly Tyr Thr Tyr Ser Ser Ala
            20                  25                  30

Phe Met Ala Trp Phe Arg Gln Ala Pro Gly Lys Glu Arg Glu Gly Val
        35                  40                  45

Ala Ala Met Tyr Thr Arg Asp Gly Gly Thr Val Tyr Ala Asp Ser Val
    50                  55                  60

Lys Gly Arg Phe Thr Ile Ser Gln Asp Asn Ala Lys Asn Thr Leu Tyr
65                  70                  75                  80

Leu Gln Met Asn Ser Leu Lys Thr Glu Asp Thr Ala Met Tyr Tyr Cys
            85                  90                  95

Ala Ala Lys Ile Pro Gln Pro Gly Arg Ala Ser Leu Leu Asp Ser Gln
        100                 105                 110

Thr Tyr Asp Tyr Trp Gly Gln Gly Thr Gln Val Thr Val Ser Ser
    115                 120                 125

<210> SEQ ID NO 130
<211> LENGTH: 126
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 130

Gln Val Gln Leu Gln Glu Ser Gly Gly Gly Ser Val Gln Ala Gly Gly
1               5                   10                  15

Phe Leu Arg Leu Ser Cys Val Ala Ser Gly Tyr Gly Tyr Cys Gly Tyr
            20                  25                  30

Asp Met Ser Trp Tyr Arg Gln Val Pro Gly Lys Glu Arg Glu Phe Val
        35                  40                  45

Ala Leu Ile Thr Ser Asp Arg Ser Val Ser Tyr Glu Asp Ser Val Lys
    50                  55                  60

Gly Arg Phe Ser Ile Ser Arg Asp Asn Ala Lys Asn Thr Ala Tyr Leu
65                  70                  75                  80

Glu Met Asn Arg Leu Thr Pro Asp Asp Thr Ala Ile Tyr Tyr Cys Lys
            85                  90                  95

Thr Ser Thr Ala Ala Arg Glu Asn Asn Trp Cys Arg Ser Arg Tyr Arg
        100                 105                 110

Ile Ala Ser Trp Gly Gln Gly Thr Gln Val Thr Val Ser Ser
    115                 120                 125

<210> SEQ ID NO 131
<211> LENGTH: 126
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 131

Gln Val Gln Leu Gln Glu Ser Gly Gly Gly Ser Val Gln Ala Gly Gly
1               5                   10                  15

Ser Leu Arg Leu Ser Cys Val Ala Ser Gly Tyr Gly Tyr Cys Gly Tyr
            20                  25                  30

Asp Met Ser Trp Tyr Arg Gln Thr Pro Gly Lys Glu Arg Glu Phe Val
        35                  40                  45

Ala Leu Ile Thr Ser Asp Arg Ile Ala Ser Tyr Glu Asp Ser Val Lys
    50                  55                  60

Gly Arg Phe Ile Ile Ser Arg Asp Asn Ala Lys Asn Thr Gly Tyr Leu
65                  70                  75                  80

Asp Met Thr Arg Val Thr Pro Asp Asp Thr Ala Ile Tyr Tyr Cys Lys
                85                  90                  95

Thr Ser Ala Ala Ala Arg Glu Asn Ser Trp Cys Arg Ser Arg Tyr Arg
            100                 105                 110

Val Ala Ser Trp Gly Gln Gly Thr Gln Val Thr Val Ser Ser
        115                 120                 125

<210> SEQ ID NO 132
<211> LENGTH: 126
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 132

Gln Val Gln Leu Gln Glu Ser Gly Gly Gly Ser Val Gln Ala Gly Gly
1               5                   10                  15

Ser Leu Arg Leu Ser Cys Ala Val Ser Gly Tyr Asp Tyr Cys Gly Tyr
            20                  25                  30

Asp Val Arg Trp Tyr Arg Arg Ala Pro Gly Lys Glu Arg Glu Phe Val
        35                  40                  45

Ser Gly Ile Asp Ser Asp Gly Ser Thr Ser Tyr Ala Asp Ser Val Lys
    50                  55                  60

Gly Arg Phe Thr Ile Ser Gln Asp Asn Ala Glu Asn Thr Ser Tyr Leu
65                  70                  75                  80

His Met Phe Ser Leu Lys Pro Glu Asp Thr Ala Met Tyr Tyr Cys Lys
                85                  90                  95

Thr Glu Ser Pro Ala Gly Glu Ser Ala Trp Cys Arg Asn Phe Arg Gly
            100                 105                 110

Met Asp Tyr Trp Gly Lys Gly Thr Gln Val Thr Val Ser Ser
        115                 120                 125

<210> SEQ ID NO 133
<211> LENGTH: 127
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 133

Gln Val Gln Leu Gln Glu Ser Gly Gly Gly Ser Val Gln Ala Gly Gly
1               5                   10                  15
Ser Leu Arg Leu Ser Cys Thr Ala Ser Gly Tyr Thr Tyr Ser Ser Ala
            20                  25                  30
Phe Met Ala Trp Phe Arg Gln Ala Pro Gly Lys Glu Arg Glu Gly Val
        35                  40                  45
Ala Ala Ile Tyr Thr Arg Asp Gly Gly Thr Val Tyr Ala Asp Ser Val
    50                  55                  60
Lys Gly Arg Phe Thr Ile Ser Gln Asp Asn Ala Lys Asn Ile Leu Tyr
65                  70                  75                  80
Leu Gln Met Asn Ser Leu Lys Ala Glu Asp Thr Ala Met Tyr Tyr Cys
                85                  90                  95
Ala Ala Lys Ile Pro Gln Pro Gly Arg Ala Ser Leu Leu Asp Ser Gln
            100                 105                 110
Thr Tyr Asp Tyr Trp Gly Gln Gly Thr Gln Val Thr Val Ser Ser
        115                 120                 125

<210> SEQ ID NO 134
<211> LENGTH: 127
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 134

Gln Val Gln Leu Gln Glu Ser Gly Gly Gly Ser Val Gln Ala Gly Gly
1               5                   10                  15
Ser Leu Arg Leu Ser Cys Thr Ala Ser Gly Tyr Thr Tyr Ser Ser Ala
            20                  25                  30
Phe Met Ala Trp Phe Arg Gln Ala Pro Gly Lys Glu Arg Glu Gly Val
        35                  40                  45
Ala Ala Ile Tyr Thr Arg Asp Gly Gly Thr Val Tyr Ala Asp Ser Val
    50                  55                  60
Lys Gly Arg Phe Thr Ile Ser Gln Asp Asn Ala Lys Asn Thr Leu Tyr
65                  70                  75                  80
Leu Gln Met Asn Ser Leu Lys Pro Glu Asp Thr Ala Met Tyr Tyr Cys
                85                  90                  95
Ala Ala Lys Met Pro Gln Pro Gly Arg Ala Ser Leu Leu Asp Ser Gln
            100                 105                 110
Thr Tyr Asp Tyr Trp Gly Gln Gly Thr Gln Val Thr Val Ser Ser
        115                 120                 125

<210> SEQ ID NO 135
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 135

Tyr Thr Tyr Ser Ser Ala Phe Met Ala
1               5

<210> SEQ ID NO 136
<211> LENGTH: 17
<212> TYPE: PRT

```
<213> ORGANISM: Artificial Sequence
<220> FEATURE:
<223> OTHER INFORMATION: Description of Artificial Sequence: Synthetic
      peptide

<400> SEQUENCE: 136

Ala Ile Tyr Thr Arg Asp Gly Gly Thr Val Tyr Ala Asp Ser Val Lys
1               5                   10                  15

Gly

<210> SEQ ID NO 137
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 137

Lys Ile Pro Gln Pro Gly Arg Ala Ser Leu Leu Asp Ser Gln Thr Tyr
1               5                   10                  15

Asp Tyr

<210> SEQ ID NO 138
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 138

Tyr Asp Tyr Cys Gly Tyr Asp Val Arg
1               5

<210> SEQ ID NO 139
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 139

Gly Ile Asp Ser Asp Gly Ser Thr Ser Tyr Ala Asp Ser Val Lys Gly
1               5                   10                  15

<210> SEQ ID NO 140
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 140

Glu Ser Pro Ala Gly Glu Ser Ala Trp Cys Arg Asn Phe Arg Gly Met
1               5                   10                  15

Asp Tyr

<210> SEQ ID NO 141
<211> LENGTH: 9
<212> TYPE: PRT
<213> ORGANISM: Artificial Sequence
<220> FEATURE:
<223> OTHER INFORMATION: Description of Artificial Sequence: Synthetic
```

```
peptide

<400> SEQUENCE: 141

Tyr Ser Tyr Cys Gly Tyr Asp Met Met
1               5

<210> SEQ ID NO 142
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 142

Leu Ile Thr Ser Asp Tyr Ser Ile Arg Tyr Glu Asp Ser Val Glu Gly
1               5                   10                  15

<210> SEQ ID NO 143
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 143

Ser Thr Ala Ala Arg Glu Ser Ser Trp Cys Arg Ser Arg Tyr Arg Val
1               5                   10                  15

Ala Ser

<210> SEQ ID NO 144
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 144

Tyr Thr Tyr Thr Asn Asn Phe Met Ala
1               5

<210> SEQ ID NO 145
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 145

Ala Ile Tyr Thr Gly Asp Gly Tyr Ala Tyr Tyr Phe Asp Ser Val Lys
1               5                   10                  15

Gly

<210> SEQ ID NO 146
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 146

Met Glu Arg Arg Ser Gly Arg Arg Arg Met Thr Glu Asn Ala Glu Tyr
```

```
1               5                   10                  15

Lys Tyr

<210> SEQ ID NO 147
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 147

Phe Thr Ile Asp Asp Ser Glu Met Gly
1               5

<210> SEQ ID NO 148
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 148

Ser Gly Ser Ser Asp Asp Asp Thr Tyr Tyr Val Asp Ser Val Lys Gly
1               5                   10                  15

<210> SEQ ID NO 149
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 149

Gly Pro Thr Tyr Pro Pro Lys Asp Gly Asp Cys Ala His
1               5                   10

<210> SEQ ID NO 150
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 150

Tyr Thr Tyr Ser Ser Ala Phe Met Ala
1               5

<210> SEQ ID NO 151
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 151

Ala Ile Tyr Thr Arg Asp Gly Ser Pro Val Tyr Ala Asp Ser Leu Lys
1               5                   10                  15

Gly

<210> SEQ ID NO 152
<211> LENGTH: 18
```

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 152

Lys Ile Pro Glu Pro Gly Arg Ile Ser Leu Leu Asp Ser Gln Thr Tyr
1               5                   10                  15

Asp Tyr

<210> SEQ ID NO 153
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 153

Tyr Asp Tyr Cys Gly Tyr Asp Val Arg
1               5

<210> SEQ ID NO 154
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 154

Gly Ile Asp Ser Asp Gly Ser Thr Ser Tyr Ala Asp Ser Val Lys Gly
1               5                   10                  15

<210> SEQ ID NO 155
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 155

Glu Ser Pro Ala Gly Glu Ser Ala Trp Cys Arg Asn Phe Arg Gly Met
1               5                   10                  15

Asp Tyr

<210> SEQ ID NO 156
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 156

Tyr Gly Tyr Cys Gly Tyr Asp Met Ser
1               5

<210> SEQ ID NO 157
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 157

Leu Ile Thr Ser Glu Arg Val Ile Ser Tyr Glu Asp Ser Val Lys Gly
1               5                   10                  15

<210> SEQ ID NO 158
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 158

Ser Ala Ala Ala Arg Glu Ser Ser Trp Cys Arg Ser Arg Tyr Arg Val
1               5                   10                  15

Ala Ser

<210> SEQ ID NO 159
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 159

Tyr Gly Tyr Cys Gly Tyr Asp Met Ser
1               5

<210> SEQ ID NO 160
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 160

Leu Ile Thr Ser Asp Arg Ser Ile Ser Tyr Glu Asp Ser Val Lys Ala
1               5                   10                  15

<210> SEQ ID NO 161
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 161

Ser Ala Ala Ala Arg Glu Ser Ser Trp Cys Arg Ser Arg Tyr Arg Val
1               5                   10                  15

Ala Ser

<210> SEQ ID NO 162
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 162

Tyr Asp Tyr Cys Gly Tyr Asp Val Arg
1               5
```

<210> SEQ ID NO 163
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 163

Gly Ile Asp Ser Asp Gly Ser Thr Ser Tyr Ala Asp Ser Val Lys Gly
1               5                   10                  15

<210> SEQ ID NO 164
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 164

Glu Ser Pro Ala Gly Glu Ser Ala Trp Cys Arg Asn Phe Arg Gly Met
1               5                   10                  15

Asp Tyr

<210> SEQ ID NO 165
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 165

Tyr Ser Tyr Cys Gly Tyr Asp Met Met
1               5

<210> SEQ ID NO 166
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 166

Leu Ile Thr Ser Asp Tyr Ser Ile Arg Tyr Glu Asp Ser Val Glu Gly
1               5                   10                  15

<210> SEQ ID NO 167
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 167

Ser Thr Ala Ala Arg Glu Ser Ser Trp Cys Arg Ser Arg Tyr Arg Val
1               5                   10                  15

Ala Ser

<210> SEQ ID NO 168
<211> LENGTH: 9
<212> TYPE: PRT

<213> ORGANISM: Artificial Sequence
<220> FEATURE:
<223> OTHER INFORMATION: Description of Artificial Sequence: Synthetic
      peptide

<400> SEQUENCE: 168

Tyr Thr Tyr Thr Asn Asn Phe Met Ala
1               5

<210> SEQ ID NO 169
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 169

Ala Ile Tyr Thr Gly Asp Gly Tyr Ala Tyr Tyr Phe Tyr Ser Val Lys
1               5                   10                  15

Gly

<210> SEQ ID NO 170
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 170

Met Glu Arg Arg Ile Gly Thr Arg Arg Met Thr Glu Asn Ala Glu Tyr
1               5                   10                  15

Lys Tyr

<210> SEQ ID NO 171
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 171

Tyr Ser Tyr Cys Gly Tyr Asp Met Met
1               5

<210> SEQ ID NO 172
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 172

Leu Ile Thr Ser Asp Tyr Ser Ile Arg Tyr Glu Asp Ser Val Glu Gly
1               5                   10                  15

<210> SEQ ID NO 173
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

```
<400> SEQUENCE: 173

Ser Thr Ala Ala Arg Glu Ser Gly Trp Cys Arg Ser Arg Tyr Arg Val
1               5                   10                  15

Ala Ser

<210> SEQ ID NO 174
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 174

Tyr Asp Tyr Cys Gly Tyr Asp Val Arg
1               5

<210> SEQ ID NO 175
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 175

Gly Ile Asn Ser Asp Gly Ser Thr Ser Tyr Ala Asp Ser Val Lys Gly
1               5                   10                  15

<210> SEQ ID NO 176
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 176

Glu Ser Pro Ala Gly Glu Ser Ala Trp Cys Arg Asn Phe Arg Gly Met
1               5                   10                  15

Asp Tyr

<210> SEQ ID NO 177
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 177

Tyr Gly Tyr Cys Gly Tyr Asp Met Ser
1               5

<210> SEQ ID NO 178
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 178

Leu Ile Thr Ser Asp Arg Ser Val Ser Tyr Glu Asp Ser Val Lys Gly
1               5                   10                  15
```

<210> SEQ ID NO 179
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 179

Ser Thr Ala Ala Arg Glu Asn Asn Trp Cys Arg Ser Arg Tyr Arg Ile
1               5                   10                  15

Ala Tyr

<210> SEQ ID NO 180
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 180

Tyr Asp Tyr Cys Gly Tyr Asp Val Arg
1               5

<210> SEQ ID NO 181
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 181

Gly Ile Asn Ser Asp Gly Ser Thr Ser Tyr Ala Asp Ser Val Lys Gly
1               5                   10                  15

<210> SEQ ID NO 182
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 182

Glu Gly Pro Ala Gly Glu Ser Ala Trp Cys Arg Asn Phe Arg Gly Met
1               5                   10                  15

Asp Tyr

<210> SEQ ID NO 183
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 183

Tyr Thr Tyr Ser Ser Ala Phe Met Ala
1               5

<210> SEQ ID NO 184
<211> LENGTH: 17
<212> TYPE: PRT
<213> ORGANISM: Artificial Sequence

```
<220> FEATURE:
<223> OTHER INFORMATION: Description of Artificial Sequence: Synthetic
      peptide

<400> SEQUENCE: 184

Ala Met Tyr Thr Arg Asp Gly Gly Thr Val Tyr Ala Asp Ser Val Lys
1               5                   10                  15

Gly

<210> SEQ ID NO 185
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 185

Lys Ile Pro Gln Pro Gly Arg Ala Ser Leu Leu Asp Ser Gln Thr Tyr
1               5                   10                  15

Asp Tyr

<210> SEQ ID NO 186
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 186

Tyr Thr Tyr Ser Ser Ala Phe Met Ala
1               5

<210> SEQ ID NO 187
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 187

Ala Met Tyr Thr Arg Asp Gly Gly Thr Val Tyr Ala Asp Ser Val Lys
1               5                   10                  15

Gly

<210> SEQ ID NO 188
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 188

Lys Ile Pro Gln Pro Gly Arg Ala Ser Leu Leu Asp Ser Gln Thr Tyr
1               5                   10                  15

Asp Tyr

<210> SEQ ID NO 189
<211> LENGTH: 9
<212> TYPE: PRT
<213> ORGANISM: Artificial Sequence
<220> FEATURE:
```

```
<223> OTHER INFORMATION: Description of Artificial Sequence: Synthetic
      peptide

<400> SEQUENCE: 189

Tyr Gly Tyr Cys Gly Tyr Asp Met Ser
1               5

<210> SEQ ID NO 190
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 190

Leu Ile Thr Ser Asp Arg Ser Val Ser Tyr Glu Asp Ser Val Lys Gly
1               5                   10                  15

<210> SEQ ID NO 191
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 191

Ser Thr Ala Ala Arg Glu Asn Asn Trp Cys Arg Ser Arg Tyr Arg Ile
1               5                   10                  15
Ala Ser

<210> SEQ ID NO 192
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 192

Tyr Gly Tyr Cys Gly Tyr Asp Met Ser
1               5

<210> SEQ ID NO 193
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 193

Leu Ile Thr Ser Asp Arg Ile Ala Ser Tyr Glu Asp Ser Val Lys Gly
1               5                   10                  15

<210> SEQ ID NO 194
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 194

Ser Ala Ala Ala Arg Glu Asn Ser Trp Cys Arg Ser Arg Tyr Arg Val
1               5                   10                  15
```

Ala Ser

<210> SEQ ID NO 195
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 195

Tyr Asp Tyr Cys Gly Tyr Asp Val Arg
1               5

<210> SEQ ID NO 196
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 196

Gly Ile Asp Ser Asp Gly Ser Thr Ser Tyr Ala Asp Ser Val Lys Gly
1               5                   10                  15

<210> SEQ ID NO 197
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 197

Glu Ser Pro Ala Gly Glu Ser Ala Trp Cys Arg Asn Phe Arg Gly Met
1               5                   10                  15

Asp Tyr

<210> SEQ ID NO 198
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 198

Tyr Thr Tyr Ser Ser Ala Phe Met Ala
1               5

<210> SEQ ID NO 199
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 199

Ala Ile Tyr Thr Arg Asp Gly Gly Thr Val Tyr Ala Asp Ser Val Lys
1               5                   10                  15

Gly

<210> SEQ ID NO 200

```
<210> SEQ ID NO 200
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 200

Lys Ile Pro Gln Pro Gly Arg Ala Ser Leu Leu Asp Ser Gln Thr Tyr
1               5                   10                  15

Asp Tyr

<210> SEQ ID NO 201
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 201

Tyr Thr Tyr Ser Ser Ala Phe Met Ala
1               5

<210> SEQ ID NO 202
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 202

Ala Ile Tyr Thr Arg Asp Gly Gly Thr Val Tyr Ala Asp Ser Val Lys
1               5                   10                  15

Gly

<210> SEQ ID NO 203
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 203

Lys Met Pro Gln Pro Gly Arg Ala Ser Leu Leu Asp Ser Gln Thr Tyr
1               5                   10                  15

Asp Tyr

<210> SEQ ID NO 204
<211> LENGTH: 381
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 204
caggtgcagc tccaggaaag cgggggaggt tccgtccagg ccggtggctc cctccgcctg      60
tcatgcacag cgagcggtta cacgtatagc tccgccttta tggcctggtt tagacaggcc    120
ccagggaaag aacgtgaggg agtggctgca atttacaccc gcgatggcgg gactgtttac    180
gccgatagcg tcaagggtcg ctttaccatc agccaggaca acgctaaaaa caccctctat    240
```

```
ctccagatga atagcctgaa ggccgaggac actgcgatgt attactgcgc cgctaagatc    300
cctcaacctg gccgcgccag cttgctggat agccagacat acgattactg gggtcaggga    360
acacaagtga cggtcagcag c                                              381

<210> SEQ ID NO 205
<211> LENGTH: 378
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 205
caggtgcagc tccaggagag cggcgggggc tccgtacagg ccggtggatc actccgcctg     60
agctgtgctg tgagcgggta cgactattgc ggatacgacg tgcgctggta tcgccaagct    120
ccagggaagg aaaggagtt cgtgagcgga attgattccg atggctccac cagttatgcc    180
gactccgtta aggaaggtt taccatctcc aagataacg ccgagaacac ctcctatctg     240
catatgtttt ccctgaaacc cgaggatacc gctatgtatt actgtaagac agagagccct    300
gccggagagt ccgcctggtg ccgcaacttt cggggcatgg actactgggg aaagggcacc    360
caggtgacag tgtctagc                                                  378

<210> SEQ ID NO 206
<211> LENGTH: 378
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 206
caggtgcagc tgcaagaatc aggaggtgga tctgtgcaag ctgggggctc tttgcgcctg     60
tcctgtgtcg cctccggcta tagctattgc ggctatgaca tgatgtggta caggcaagcc    120
ccaggtaagg agagggagtt tgtggctctc atcacctccg actacagcat cgctatgaa    180 gatagtgtcg agggacgctt ctccatttct cgcgacaacg cgaagaacac tggctatttg    240
ctgatgagta acctcacccc cgccgacacc gcgatctact attgcaaaac atctaccgcc    300
gctcgggaaa gtagctggtg taggtcacgt tatagggtcg cttcctgggg tcagggcacg    360
caggtgaccg tctcatcc                                                  378

<210> SEQ ID NO 207
<211> LENGTH: 381
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 207
caggtgcagt tgcaggagag cggaggcgga tctgtgcagg caggcggaag cctccgcctg     60
tcttgcgccg cttcccggta cacctacaca aataacttta tggcatggtt ccgccaagcg    120
cccggcaagg agcgcgaggg tgtcgcgcc atttacacag gtgatggcta cgcctattac    180
ttcgactccg tgaaaggcag gttcacgatc tcccaggata cgacaagaa tatgttgtat    240 cttcagatga actctctgaa acctgaggac ccgctatgt actattgtgc agctatggaa    300
cgcaggtcag gcaggcgcag gatgaccgag aacgccgagt acaagtactg ggccagggc    360
```

-continued

```
acccaggtga ccgtgtcttc a                                              381

<210> SEQ ID NO 208
<211> LENGTH: 363
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 208
caggtgcagc tccaggagtc tggaggcggt tccgtccagg ccggggaaac gctccggctt    60
agctgcaccg tctccggttt caccattgat gactccgaaa tgggttggta tcgccaagcg   120
cccggccatg agtgcgaact ggtggccagc ggaagttccg acgatgacac ctattacgtg   180
gactcagtga agggtcgctt tacgatctct ctggataacg ccaaaaacat ggtgtacctc   240
cagatgaact cactcaagcc agaggataca gcagtttatt actgtgccac tggacctaca   300
taccctccca aggatggtga ctgcgcacac tggggtcaag caccaggt cactgtctcc    360 tcc                                                                 363

<210> SEQ ID NO 209
<211> LENGTH: 381
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 209
caagtccagc tccaggagtc tgggggaggc tcagtgcaag ctggtggatc tcttcgcctg    60
tcttgcaccg cttctgggta cacctatagc tctgccttca tggcctggtt taggcaagcg   120
cctggcaagg agcgggaggg cgtcgccgct atctacaccc gcgacggcag tccggtttat   180
gccgactccc tgaagggtag atttactatc tctcaggata atgcaaagaa tacgctgcac   240
ttgcagatga actccctcaa acccgaggac acggccatgt attactgtgc tgcaaaaatc   300
ccagagcctg gtcggatctc cctcctggat tcacagacct acgactactg gggccacggc   360
acccaggtga cagtctcttc c                                             381

<210> SEQ ID NO 210
<211> LENGTH: 378
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 210
caggtgcagc tccaggagtc cggtggcgga agcgtgcagg ccggtggctc cctgcggttg    60
agttgcgcgg tctcaggtta cgattattgt ggctacgacg tgcgctggta tagacgcgct   120
cctggcaagg agcgtgagtt cgtgtctggc atcgactccg atggctctac ttcatacgct   180
gattccgtca aaggccgttt caccatctct caggataacg ccgagaacac ctcctacctt   240
cacatgttct ctctgaagcc cgaggatact gcaatgtatt actgtaagac tgagtctcct   300
gccggagaat ccgcctggtg tcgtaacttt cgtggcatgg actactgggg taagggaacc   360
caggtgactg tatcttcc                                                 378

<210> SEQ ID NO 211
```

-continued

<211> LENGTH: 378
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 211
caggtccagt tgcaggagtc tggtggaggc tccgtccaag ctgggggctt tcttaggctg      60
tcatgtgtgg catccggcta tgggtattgt ggctatgata tgtcctggta tagacaagcg     120
cccggcaagg agcgcgagtt cgtggcgctg attaccagcg agcgcgttat cagctacgag     180
gactccgtca aaggcagatt ctccatctca cgcgacaacg ccgagaacac aggctatctg     240
gaaatgaatc gtttgacacc tgatgacacc gctatctact attgcaagac ctctgcggct     300
gcgcgtgagt ctagctggtg ccgttcccgc tatagagtgg cttcttgggg tcagggaacc     360
caggtgacag tctccagc                                                   378

<210> SEQ ID NO 212
<211> LENGTH: 378
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 212
caggtacagc tccaggagtc tggaggcggg agcgtgcagg caggcggttc cctgcgtctg      60
tcctgcgtcg cctctgggta tgggtactgc ggctacgata tgtcctggta tcgtcaggct     120
cccggcaaag aaagagagtt cgtagccctc atcacatctg accggagcat ttcctacgaa     180
gactccgtca aggcccgctt cattatctca cgggataacg cagccaacac cggatacctg     240
gacatgactc gcctgacccc cgatgacact gctatctatt actgcaagac gagcgcggca     300
gctcgcgaga gttcttggtg ccggtcccgg tacagggtgg cgtcctgggg ccaggggact     360
caggtcaccg tctcctcc                                                   378

<210> SEQ ID NO 213
<211> LENGTH: 378
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 213
caggtgcaac tccaggagag tggaggtggc tcagtacagg ccgggggaag cctccgtctg      60
agctgtgccg tgtccggcta cgattactgt ggttacgacg tgcggtggta tcgccaggcc     120
cctggtaagg aaagagagtt cgtgtccggc atcgacagcg atggtagcac atcttacgcc     180
gactccgtga agggccgctt cacaatctcc caggacaacg ccgaaaacac gtcttacctc     240
catatgtttt ccctgaaacc tgaagacacc gctatgtatt actgcaagac cgagtctccc     300
gctggcgagt cagcatggtg taggaacttt cgcggcatgg actattgggg taagggcacc     360
caggtgacgg tgagttct                                                   378

<210> SEQ ID NO 214
<211> LENGTH: 378
<212> TYPE: DNA
<213> ORGANISM: Artificial Sequence
<220> FEATURE:

<223> OTHER INFORMATION: Description of Artificial Sequence: Synthetic
polynucleotide

<400> SEQUENCE: 214

| | |
|---|---|
| caggtgcagc tccaggaaag cggcggggga agcgtgcagg caggaggctc ccttcggttg | 60 |
| agctgcgtgg ccagcggcta cagctactgc ggctacgaca tgatgtggta tcgccaagct | 120 |
| ccggggaagg agcgcgagtt cgtcgccctc atcaccagtg attattctat ccgctacgaa | 180 |
| gactctgtgg aaggtaggtt ctccattagc agagacaacg caaagaacac tggatacctg | 240 |
| cttatgagca acctcacacc cgccgacact gccatctact attgtaagac ctctaccgcc | 300 |
| gctcgcgaaa gctcctggtg caggtcccgc tatcgcgtgg ccagttgggg tcagggaacc | 360 |
| caggtgacgg tatctagc | 378 |

<210> SEQ ID NO 215
<211> LENGTH: 381
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 215

| | |
|---|---|
| caggttcagt tgcaggagtc tggaggtggc agtgtgcaag ctggaggctc cctccgcctg | 60 |
| agttgcgctg ccagcagata tacctatacg aataacttta tggcttggtt tagacaggcc | 120 |
| cccggtaaag agcgggaagg tgtggccgcg atttacaccg gcgatggcta cgcctattac | 180 |
| ttttacagcg tgaagggacg tttcaccatt tctcaggata acgatgaaaa catgctgtat | 240 |
| ctccaaatga actctctgaa gcctgaagac accgctatgt attactgcgc ggctatggag | 300 |
| cgcaggatcg gaacaagacg catgactgag aacgctgagt ataaatattg gggacaaggc | 360 |
| acacaggtga cagttagctc c | 381 |

<210> SEQ ID NO 216
<211> LENGTH: 378
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 216

| | |
|---|---|
| caggtccaac tccaggagtc cgggggaggg tctgtgcagg cgggtggctc cctgcgcctg | 60 |
| agctgtgtcg cgtctggtta ctcctactgt ggatatgata tgatgtggta tagacaggcc | 120 |
| ccaggtaagg agcgcgagtt tgtggccctg attaccagcg actacagtat ccgctatgag | 180 |
| gattccgtgg agggccgctt ctctatctca cgcgacaacg ccaagaatac aggctacctc | 240 |
| ctgatgagca acctgacccc tgccgacaca gccatttatt actgcaagac ctccaccgcc | 300 |
| gcgcgtgaat ccggctggtg caggtcacgc tatcgtgtcg ccagctgggg tcagggaca | 360 |
| caggtgacgg tgtcatct | 378 |

<210> SEQ ID NO 217
<211> LENGTH: 378
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 217

```
caagtgcagt tgcaagaatc aggaggcggg tccgtgcagg cgggcggatc tctgcgtctg    60
tcttgtgctg tctccggtta tgactactgt ggttacgacg tgcgctggta tcgccaggcc   120
cctggtaagg aacgtgagtt cgtgagcggg atcaatagcg acggctccac ctcttatgcc   180
gacagtgtga agggtaggtt taccatcagt caagacaacg ccgagaacac atcctacctt   240
catatgttct ctctcaagcc tgaggatacc gcaatgtact attgcaagac ggagtcccca   300
gcaggtgagt ccgcttggtg cagaaacttt cgcggcatgg attattgggg aagggaacc    360 caggtcaccg tgtcttcc                                                 378
```

<210> SEQ ID NO 218
<211> LENGTH: 378
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 218

```
caggtgcaac ttcaggaatc cggtggcgga tctgttcagg ctggcggatt cctgcgcctg    60
tcttgcgtgg ccagtggcta cggctactgc ggctatgata tgtcatggta tcgccaagtg   120
cccggcaagg agcgcgagtt tgtagccctc atcacatctg atcgttctgt cagctacgaa   180
gacagtgtca agggccgctt ttccatcagc cgcgataatg cgaagaacac ggcctacctg   240
gagatgaaca gactgacacc ggatgacacc gctgtatatt actgtaagac ctcaacggct   300
gccagagaga ataattggtg ccgttctcgc taccgcatcg cttattgggg ccagggaaca   360
caggtcacag tctcctcc                                                 378
```

<210> SEQ ID NO 219
<211> LENGTH: 378
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 219

```
caggtgcaac tccaggagag cgggggaggt tccgttcagg ccgggggttc cctcagattg    60
tcttgtgccg tctccgggta cgattactgt ggctatgacg tgcgctggta tcggcaggct   120
cctgggaagg agcgggagtt cgtgagtggc attaactcag acgggtctac ctcctatgcc   180
gacagcgtta agggcaggtt tactatcagt caggacaatg cggagaatac cagttacctg   240
cacatgttca gcctcaagcc cgaggatacc gccatgtatt actgcaagac agagggtcca   300
gctggcgagt ccgcatggtg ccgcaacttc aggggtatgg actactgggg caagggtact   360
caggtgactg tgtcctct                                                 378
```

<210> SEQ ID NO 220
<211> LENGTH: 381
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 220

```
caggtgcagt tgcaggagtc aggcgggggc tctgtccagg ctgggggctc tctgagactg    60
tcttgtactg cgtctggtta cacgtacagt tctgccttta tggcctggtt tcggcaagcg   120
```

```
cccggaaagg agcgcgaggg tgttgctgcc atgtataccc gtgatggcgg aaccgtctac    180
gcagattctg ttaagggtcg tttcacaatc tcccaggaca atgcgaaaaa taccctctat    240
ctccagatcc acaccttgaa ggctgaggac accgcgatgt attactgtgc tgccaagatc    300
ccgcagcctg gccgcgcttc cctgctcgac agccagacat acgactactg gggtcagggc    360
acacaggtta ccgtgagtag t                                              381
```

<210> SEQ ID NO 221
<211> LENGTH: 381
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 221

```
caagtccaac tccaggaaag cggaggtggc agcgtccagg ccgggggctc tctgagactg     60
tcttgtaccg cttccggcta tacatattcc tctgccttta tggcatggtt ccgccaagcg    120
ccaggcaagg agcgcgaggg cgtcgccgct atgtatacca gagacggagg caccgtctac    180
gctgacagcg tcaagggacg cttcacaatc tcccaggaca cgccaagaa tactttgtat     240 ctccagatga atagcctcaa gacggaggac accgcaatgt attactgcgc tgcaaaaatc    300
cctcagccag tcgcgcctc cctcctggac agtcagacct atgattattg gggccagggg    360
acccaggtga ctgtctcctc c                                              381
```

<210> SEQ ID NO 222
<211> LENGTH: 378
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 222

```
caggtacagt tgcaggagtc cggcggaggc agcgttcagg ccgtggctt cctgaggctg      60 tcctgcgtcg ccagcggcta tggatattgc ggctacgata tgtcctggta cagacaggtc    120
cctgggaaag aacgcgagtt cgtggctctt atcacatccg acaggtccgt gtcctatgag    180
gactctgtca agggccgttt cagcatcagc cgtgacaacg caaaaaacac ggcttacttg    240
gagatgaacc ggcttacccc cgacgatacc gcgatttatt actgcaagac cagcacagca    300
gccagggaaa ataattggtg tcggagccgt tatcgtatcg cctcttgggg acagggaacc    360
caggtgactg tctcctca                                                  378
```

<210> SEQ ID NO 223
<211> LENGTH: 378
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 223

```
caggtgcagc tccaggagtc cggcggaggc tcagtacaag ctggcggttc actcaggttg     60
agttgtgtcg ccagtggcta cggctattgt ggctatgata tgtcttggta tcgccagacc    120
cccggcaagg agcgtgagtt cgtggcactc atcacgtccg accggatcgc ctcttacgaa    180
gactctgtca agggccgttt tattatcagc cgcgacaacg caaaaaacac tggttatctc    240
```

```
gacatgactc gggtgacccc cgatgacact gccatctact attgcaaaac ctctgctgcg    300
gcccgcgaga actcctggtg ccgtagtcgc taccgcgtcg cctcctgggg acagggtaca    360
caggtgaccg ttagctcc                                                  378
```

<210> SEQ ID NO 224
<211> LENGTH: 378
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 224

```
caggtccaac tgcaagagtc tggcggtggc tccgtgcagg ctggcggtag tctgcgcctg     60
tcttgtgcag tcagcgggta cgactactgc ggttatgatg tcagatggta tcgccgtgct   120
cccggcaagg aacgcgagtt cgtctctggc attgactccg acggctctac ctcctatgcc   180
gatagcgtaa agggaaggtt caccatcagc caggacaacg ctgagaacac cagctacttg   240
cacatgttct cccttaaacc tgaggacaca gctatgtatt actgtaaaac tgagagcccg   300
gctggcgaga gcgcctggtg tcgcaacttt cgtggcatgg actactgggg taagggcacc   360
caggttactg tctctagt                                                  378
```

<210> SEQ ID NO 225
<211> LENGTH: 381
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 225

```
caggtgcaac ttcaggagag cggtggcggt tcagtgcagg ctgggggaag cctgcgcctg     60
tcttgcaccg cttccggcta cacctattcc agtgccttca tggcctggtt ccgccaggcc   120
cctggaaagg aacgcgaagg cgtggctgcc atttatacac gggatggggg aaccgtctac   180
gcggactccg tcaagggaag attcaccatt agccaggata atgctaagaa catcctgtac   240
ctccagatga actccctcaa agccgaggat actgctatgt actattgtgc cgctaagatt   300
ccgcagccag gccgggcatc cctcctggac agccagacct atgactactg ggacagggg    360 acccaggtga ccgtgtcttc c                                              381
```

<210> SEQ ID NO 226
<211> LENGTH: 381
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 226

```
caggtgcagc tccaggagtc cggcggtggc agtgtccagg caggaggcag tctgcgtctg     60
tcttgcactg cctcaggcta cacatactca agcgcattca tggcctggtt caggcaggcc   120
cctgggaagg agcgcgaggg tgtggcagct atctacaccc gcgatggcgg tactgtgtac   180
gccgatagtg tcaagggggcg ctttaccatt tctcaggaca acgcgaagaa caccctgtac   240
ttgcagatga acagcctgaa gccggaggat actgctatgt attactgcgc cgcaaaaatg   300
ccccagccgg gccgcgcgtc tttgctggat tcccagacat acgactactg ggggcagggc   360
```
acccaggtta cggttagctc c                                            381

<210> SEQ ID NO 227
<211> LENGTH: 522
<212> TYPE: PRT
<213> ORGANISM: Homo sapiens

<400> SEQUENCE: 227

```
Cys Arg Thr Ser Glu Cys Cys Phe Gln Asp Pro Pro Tyr Pro Asp Ala
1               5                   10                  15

Asp Ser Gly Ser Ala Ser Gly Pro Arg Asp Leu Arg Cys Tyr Arg Ile
            20                  25                  30

Ser Ser Asp Arg Tyr Glu Cys Ser Trp Gln Tyr Glu Gly Pro Thr Ala
        35                  40                  45

Gly Val Ser His Phe Leu Arg Cys Cys Leu Ser Ser Gly Arg Cys Cys
    50                  55                  60

Tyr Phe Ala Ala Gly Ser Ala Thr Arg Leu Gln Phe Ser Asp Gln Ala
65                  70                  75                  80

Gly Val Ser Val Leu Tyr Thr Val Thr Leu Trp Val Glu Ser Trp Ala
                85                  90                  95

Arg Asn Gln Thr Glu Lys Ser Pro Glu Val Thr Leu Gln Leu Tyr Asn
            100                 105                 110

Ser Val Lys Tyr Glu Pro Pro Leu Gly Asp Ile Lys Val Ser Lys Leu
        115                 120                 125

Ala Gly Gln Leu Arg Met Glu Trp Glu Thr Pro Asp Asn Gln Val Gly
    130                 135                 140

Ala Glu Val Gln Phe Arg His Arg Thr Pro Ser Ser Pro Trp Lys Leu
145                 150                 155                 160

Gly Asp Cys Gly Pro Gln Asp Asp Thr Glu Ser Cys Leu Cys Pro
                165                 170                 175

Leu Glu Met Asn Val Ala Gln Glu Phe Gln Leu Arg Arg Arg Gln Leu
            180                 185                 190

Gly Ser Gln Gly Ser Ser Trp Ser Lys Trp Ser Ser Pro Val Cys Val
        195                 200                 205

Pro Pro Glu Asn Pro Pro Gln Pro Gln Val Arg Phe Ser Val Glu Gln
    210                 215                 220

Leu Gly Gln Asp Gly Arg Arg Arg Leu Thr Leu Lys Glu Gln Pro Thr
225                 230                 235                 240

Gln Leu Glu Leu Pro Glu Gly Cys Gln Gly Leu Ala Pro Gly Thr Glu
                245                 250                 255

Val Thr Tyr Arg Leu Gln Leu His Met Leu Ser Cys Pro Cys Lys Ala
            260                 265                 270

Lys Ala Thr Arg Thr Leu His Leu Gly Lys Met Pro Tyr Leu Ser Gly
        275                 280                 285

Ala Ala Tyr Asn Val Ala Val Ile Ser Ser Asn Gln Phe Gly Pro Gly
    290                 295                 300

Leu Asn Gln Thr Trp His Ile Pro Ala Asp Thr His Thr Glu Pro Val
305                 310                 315                 320

Ala Leu Asn Ile Ser Val Gly Thr Asn Gly Thr Thr Met Tyr Trp Pro
                325                 330                 335

Ala Arg Ala Gln Ser Met Thr Tyr Cys Ile Glu Trp Gln Pro Val Gly
            340                 345                 350

Gln Asp Gly Gly Leu Ala Thr Cys Ser Leu Thr Ala Pro Gln Asp Pro
        355                 360                 365
```

```
Asp Pro Ala Gly Met Ala Thr Tyr Ser Trp Ser Arg Glu Ser Gly Ala
    370                 375                 380

Met Gly Gln Glu Lys Cys Tyr Tyr Ile Thr Ile Phe Ala Ser Ala His
385                 390                 395                 400

Pro Glu Lys Leu Thr Leu Trp Ser Thr Val Leu Ser Thr Tyr His Phe
                405                 410                 415

Gly Gly Asn Ala Ser Ala Ala Gly Thr Pro His His Val Ser Val Lys
                420                 425                 430

Asn His Ser Leu Asp Ser Val Ser Val Asp Trp Ala Pro Ser Leu Leu
            435                 440                 445

Ser Thr Cys Pro Gly Val Leu Lys Glu Tyr Val Val Arg Cys Arg Asp
        450                 455                 460

Glu Asp Ser Lys Gln Val Ser Glu His Pro Val Gln Pro Thr Glu Thr
465                 470                 475                 480

Gln Val Thr Leu Ser Gly Leu Arg Ala Gly Val Ala Tyr Thr Val Gln
                485                 490                 495

Val Arg Ala Asp Thr Ala Trp Leu Arg Gly Val Trp Ser Gln Pro Gln
                500                 505                 510

Arg Phe Ser Ile Glu Val Gln Val Ser Asp
            515                 520

<210> SEQ ID NO 228
<211> LENGTH: 738
<212> TYPE: PRT
<213> ORGANISM: Mus musculus

<400> SEQUENCE: 228

Met Asp Met Met Gly Leu Ala Gly Thr Ser Lys His Ile Thr Phe Leu
1               5                   10                  15

Leu Leu Cys Gln Leu Gly Ala Ser Gly Pro Gly Asp Gly Cys Cys Val
                20                  25                  30

Glu Lys Thr Ser Phe Pro Glu Gly Ala Ser Gly Ser Pro Leu Gly Pro
                35                  40                  45

Arg Asn Leu Ser Cys Tyr Arg Val Ser Lys Thr Asp Tyr Glu Cys Ser
    50                  55                  60

Trp Gln Tyr Asp Gly Pro Glu Asp Asn Val Ser His Val Leu Trp Cys
65                  70                  75                  80

Cys Phe Val Pro Pro Asn His Thr His Thr Gly Gln Glu Arg Cys Arg
                85                  90                  95

Tyr Phe Ser Ser Gly Pro Asp Arg Thr Val Gln Phe Trp Glu Gln Asp
                100                 105                 110

Gly Ile Pro Val Leu Ser Lys Val Asn Phe Trp Val Glu Ser Arg Leu
            115                 120                 125

Gly Asn Arg Thr Met Lys Ser Gln Lys Ile Ser Gln Tyr Leu Tyr Asn
        130                 135                 140

Trp Thr Lys Thr Thr Pro Pro Leu Gly His Ile Lys Val Ser Gln Ser
145                 150                 155                 160

His Arg Gln Leu Arg Met Asp Trp Asn Val Ser Glu Glu Ala Gly Ala
                165                 170                 175

Glu Val Gln Phe Arg Arg Arg Met Pro Thr Thr Asn Trp Thr Leu Gly
                180                 185                 190

Asp Cys Gly Pro Gln Val Asn Ser Gly Ser Gly Val Leu Gly Asp Ile
            195                 200                 205

Arg Gly Ser Met Ser Glu Ser Cys Leu Cys Pro Ser Glu Asn Met Ala
```

```
            210                 215                 220
Gln Glu Ile Gln Ile Arg Arg Arg Arg Leu Ser Ser Gly Ala Pro
225                 230                 235                 240

Gly Gly Pro Trp Ser Asp Trp Ser Met Pro Val Cys Val Pro Pro Glu
                245                 250                 255

Val Leu Pro Gln Ala Lys Ile Lys Phe Leu Val Glu Pro Leu Asn Gln
            260                 265                 270

Gly Gly Arg Arg Arg Leu Thr Met Gln Gly Gln Ser Pro Gln Leu Ala
            275                 280                 285

Val Pro Glu Gly Cys Arg Gly Arg Pro Gly Ala Gln Val Lys Lys His
        290                 295                 300

Leu Val Leu Val Arg Met Leu Ser Cys Arg Cys Gln Ala Gln Thr Ser
305                 310                 315                 320

Lys Thr Val Pro Leu Gly Lys Lys Leu Asn Leu Ser Gly Ala Thr Tyr
                325                 330                 335

Asp Leu Asn Val Leu Ala Lys Thr Arg Phe Gly Arg Ser Thr Ile Gln
            340                 345                 350

Lys Trp His Leu Pro Ala Gln Glu Leu Thr Glu Thr Arg Ala Leu Asn
            355                 360                 365

Val Ser Val Gly Gly Asn Met Thr Ser Met Gln Trp Ala Ala Gln Ala
        370                 375                 380

Pro Gly Thr Thr Tyr Cys Leu Glu Trp Gln Pro Trp Phe Gln His Arg
385                 390                 395                 400

Asn His Thr His Cys Thr Leu Ile Val Pro Glu Glu Glu Asp Pro Ala
                405                 410                 415

Lys Met Val Thr His Ser Trp Ser Ser Lys Pro Thr Leu Glu Gln Glu
            420                 425                 430

Glu Cys Tyr Arg Ile Thr Val Phe Ala Ser Lys Asn Pro Lys Asn Pro
            435                 440                 445

Met Leu Trp Ala Thr Val Leu Ser Ser Tyr Tyr Phe Gly Gly Asn Ala
        450                 455                 460

Ser Arg Ala Gly Thr Pro Arg His Val Ser Val Arg Asn Gln Thr Gly
465                 470                 475                 480

Asp Ser Val Ser Val Glu Trp Thr Ala Ser Gln Leu Ser Thr Cys Pro
                485                 490                 495

Gly Val Leu Thr Gln Tyr Val Val Arg Cys Glu Ala Glu Asp Gly Ala
            500                 505                 510

Trp Glu Ser Glu Trp Leu Val Pro Pro Thr Lys Thr Gln Val Thr Leu
            515                 520                 525

Asp Gly Leu Arg Ser Arg Val Met Tyr Lys Val Gln Val Arg Ala Asp
        530                 535                 540

Thr Ala Arg Leu Pro Gly Ala Trp Ser His Pro Gln Arg Phe Ser Phe
545                 550                 555                 560

Glu Val Gln Ile Ser Arg Leu Ser Ile Ile Phe Ala Ser Leu Gly Ser
                565                 570                 575

Phe Ala Ser Val Leu Leu Val Gly Ser Leu Gly Tyr Ile Gly Leu Asn
            580                 585                 590

Arg Ala Ala Trp His Leu Cys Pro Pro Leu Pro Thr Pro Cys Gly Ser
            595                 600                 605

Thr Ala Val Glu Phe Pro Gly Ser Gln Gly Lys Gln Ala Trp Gln Trp
        610                 615                 620

Cys Asn Pro Glu Asp Phe Pro Glu Val Leu Tyr Pro Arg Asp Ala Leu
625                 630                 635                 640
```

```
Val Val Glu Met Pro Gly Asp Arg Gly Asp Gly Thr Glu Ser Pro Gln
                645                 650                 655

Ala Ala Pro Glu Cys Ala Leu Asp Thr Arg Arg Pro Leu Glu Thr Gln
                660                 665                 670

Arg Gln Arg Gln Val Gln Ala Leu Ser Glu Ala Arg Arg Leu Gly Leu
                675                 680                 685

Ala Arg Glu Asp Cys Pro Arg Gly Asp Leu Ala His Val Thr Leu Pro
                690                 695                 700

Leu Leu Leu Gly Gly Val Thr Gln Gly Ala Ser Val Leu Asp Asp Leu
705                 710                 715                 720

Trp Arg Thr His Lys Thr Ala Glu Pro Gly Pro Pro Thr Leu Gly Gln
                725                 730                 735

Glu Ala

<210> SEQ ID NO 229
<211> LENGTH: 546
<212> TYPE: PRT
<213> ORGANISM: Mus musculus

<400> SEQUENCE: 229

Gln Leu Gly Ala Ser Gly Pro Gly Asp Gly Cys Cys Val Glu Lys Thr
1               5                   10                  15

Ser Phe Pro Glu Gly Ala Ser Gly Ser Pro Leu Gly Pro Arg Asn Leu
                20                  25                  30

Ser Cys Tyr Arg Val Ser Lys Thr Asp Tyr Glu Cys Ser Trp Gln Tyr
                35                  40                  45

Asp Gly Pro Glu Asp Asn Val Ser His Val Leu Trp Cys Cys Phe Val
            50                  55                  60

Pro Pro Asn His Thr His Thr Gly Gln Glu Arg Cys Arg Tyr Phe Ser
65                  70                  75                  80

Ser Gly Pro Asp Arg Thr Val Gln Phe Trp Glu Gln Asp Gly Ile Pro
                85                  90                  95

Val Leu Ser Lys Val Asn Phe Trp Val Glu Ser Arg Leu Gly Asn Arg
                100                 105                 110

Thr Met Lys Ser Gln Lys Ile Ser Gln Tyr Leu Tyr Asn Trp Thr Lys
                115                 120                 125

Thr Thr Pro Pro Leu Gly His Ile Lys Val Ser Gln Ser His Arg Gln
            130                 135                 140

Leu Arg Met Asp Trp Asn Val Ser Glu Glu Ala Gly Ala Glu Val Gln
145                 150                 155                 160

Phe Arg Arg Arg Met Pro Thr Thr Asn Trp Thr Leu Gly Asp Cys Gly
                165                 170                 175

Pro Gln Val Asn Ser Gly Ser Gly Val Leu Gly Asp Ile Arg Gly Ser
                180                 185                 190

Met Ser Glu Ser Cys Leu Cys Pro Ser Glu Asn Met Ala Gln Glu Ile
                195                 200                 205

Gln Ile Arg Arg Arg Arg Leu Ser Ser Gly Ala Pro Gly Gly Pro
            210                 215                 220

Trp Ser Asp Trp Ser Met Pro Val Cys Val Pro Pro Glu Val Leu Pro
225                 230                 235                 240

Gln Ala Lys Ile Lys Phe Leu Val Glu Pro Leu Asn Gln Gly Gly Arg
                245                 250                 255

Arg Arg Leu Thr Met Gln Gly Gln Ser Pro Gln Leu Ala Val Pro Glu
                260                 265                 270
```

-continued

```
Gly Cys Arg Gly Arg Pro Gly Ala Gln Val Lys Lys His Leu Val Leu
            275                 280                 285
Val Arg Met Leu Ser Cys Arg Cys Gln Ala Gln Thr Ser Lys Thr Val
        290                 295                 300
Pro Leu Gly Lys Lys Leu Asn Leu Ser Gly Ala Thr Tyr Asp Leu Asn
305                 310                 315                 320
Val Leu Ala Lys Thr Arg Phe Gly Arg Ser Thr Ile Gln Lys Trp His
                325                 330                 335
Leu Pro Ala Gln Glu Leu Thr Glu Thr Arg Ala Leu Asn Val Ser Val
            340                 345                 350
Gly Gly Asn Met Thr Ser Met Gln Trp Ala Ala Gln Ala Pro Gly Thr
        355                 360                 365
Thr Tyr Cys Leu Glu Trp Gln Pro Trp Phe Gln His Arg Asn His Thr
    370                 375                 380
His Cys Thr Leu Ile Val Pro Glu Glu Glu Asp Pro Ala Lys Met Val
385                 390                 395                 400
Thr His Ser Trp Ser Ser Lys Pro Thr Leu Glu Gln Glu Glu Cys Tyr
                405                 410                 415
Arg Ile Thr Val Phe Ala Ser Lys Asn Pro Lys Asn Pro Met Leu Trp
            420                 425                 430
Ala Thr Val Leu Ser Ser Tyr Tyr Phe Gly Gly Asn Ala Ser Arg Ala
        435                 440                 445
Gly Thr Pro Arg His Val Ser Val Arg Asn Gln Thr Gly Asp Ser Val
    450                 455                 460
Ser Val Glu Trp Thr Ala Ser Gln Leu Ser Thr Cys Pro Gly Val Leu
465                 470                 475                 480
Thr Gln Tyr Val Val Arg Cys Glu Ala Glu Asp Gly Ala Trp Glu Ser
                485                 490                 495
Glu Trp Leu Val Pro Pro Thr Lys Thr Gln Val Thr Leu Asp Gly Leu
            500                 505                 510
Arg Ser Arg Val Met Tyr Lys Val Gln Val Arg Ala Asp Thr Ala Arg
        515                 520                 525
Leu Pro Gly Ala Trp Ser His Pro Gln Arg Phe Ser Phe Glu Val Gln
    530                 535                 540
Ile Ser
545

<210> SEQ ID NO 230
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 230

His His His His His His
1               5

<210> SEQ ID NO 231
<211> LENGTH: 8
<212> TYPE: PRT
<213> ORGANISM: Artificial Sequence
<220> FEATURE:
<223> OTHER INFORMATION: Description of Artificial Sequence: Synthetic
      8xHis tag

<400> SEQUENCE: 231
```

His His His His His His His His
1               5

<210> SEQ ID NO 232
<211> LENGTH: 40
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: SITE
<222> LOCATION: (1)..(40)
<223> OTHER INFORMATION: This sequence may encompass 1-10 "Gly Gly Gly
      Ser" repeating units

<400> SEQUENCE: 232

Gly Gly Gly Ser Gly Gly Gly Ser Gly Gly Gly Ser Gly Gly Gly Ser
1               5                   10                  15

Gly Gly Gly Ser Gly Gly Gly Ser Gly Gly Gly Ser Gly Gly Gly Ser
            20                  25                  30

Gly Gly Gly Ser Gly Gly Gly Ser
        35                  40

<210> SEQ ID NO 233
<211> LENGTH: 50
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: SITE
<222> LOCATION: (1)..(50)
<223> OTHER INFORMATION: This sequence may encompass 1-10 "Gly Gly Gly
      Ser Gly" repeating units

<400> SEQUENCE: 233

Gly Gly Gly Ser Gly Gly Gly Gly Ser Gly Gly Gly Ser Gly Gly
1               5                   10                  15

Gly Gly Ser Gly Gly Gly Ser Gly Gly Gly Gly Ser Gly Gly Gly
            20                  25                  30

Gly Ser Gly Gly Gly Gly Ser Gly Gly Gly Ser Gly Gly Gly Gly
        35                  40                  45

Ser Gly
    50

<210> SEQ ID NO 234
<211> LENGTH: 40
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: SITE
<222> LOCATION: (1)..(40)
<223> OTHER INFORMATION: This sequence may encompass 1-10 "Gly Gly Ser
      Gly" repeating units

<400> SEQUENCE: 234

Gly Gly Ser Gly Gly Gly Ser Gly Gly Gly Ser Gly Gly Gly Ser Gly
1               5                   10                  15

Gly Gly Ser Gly Gly Gly Ser Gly Gly Gly Ser Gly Gly Gly Ser Gly
            20                  25                  30

```
Gly Gly Ser Gly Gly Gly Ser Gly
        35                  40

<210> SEQ ID NO 235
<211> LENGTH: 6
<212> TYPE: PRT
<213> ORGANISM: Artificial Sequence
<220> FEATURE:
<223> OTHER INFORMATION: Description of Artificial Sequence: Synthetic
      His tag
<220> FEATURE:
<221> NAME/KEY: SITE
<222> LOCATION: (1)..(6)
<223> OTHER INFORMATION: This sequence may encompass 3-6 residues

<400> SEQUENCE: 235

His His His His His His
1               5
```